US010545148B2

(12) United States Patent
Iyer et al.

(10) Patent No.: US 10,545,148 B2
(45) Date of Patent: *Jan. 28, 2020

(54) MARKER SYSTEM, IN PARTICULAR FOR BACULOVIRUS-EXPRESSED SUBUNIT ANTIGENS

(71) Applicant: BOEHRINGER INGELHEIM ANIMAL HEALTH USA INC., Duluth, GA (US)

(72) Inventors: Arun V. Iyer, Ames, IA (US); Joseph Ralph Hermann, Waukee, IA (US); Michael B. Roof, Ames, IA (US); Eric Martin Vaughn, Ames, IA (US); Merrill Lynn Schaeffer, St. Joseph, MO (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/184,018

(22) Filed: Nov. 8, 2018

(65) Prior Publication Data

US 2019/0154688 A1  May 23, 2019

Related U.S. Application Data

(63) Continuation of application No. 15/061,690, filed on Mar. 4, 2016, now Pat. No. 10,168,330.

(60) Provisional application No. 62/128,744, filed on Mar. 5, 2015.

(51) Int. Cl.
| | |
|---|---|
| *G01N 33/569* | (2006.01) |
| *G01N 33/68* | (2006.01) |
| *G01N 33/50* | (2006.01) |
| *A61K 39/12* | (2006.01) |
| *C12Q 1/70* | (2006.01) |
| *C12P 21/00* | (2006.01) |
| *A61K 39/145* | (2006.01) |
| *C12N 7/00* | (2006.01) |
| *C07K 14/005* | (2006.01) |
| *A61K 39/00* | (2006.01) |

(52) U.S. Cl.
CPC ....... *G01N 33/56983* (2013.01); *A61K 39/12* (2013.01); *A61K 39/145* (2013.01); *C07K 14/005* (2013.01); *C12N 7/00* (2013.01); *C12P 21/00* (2013.01); *C12Q 1/701* (2013.01); *G01N 33/5091* (2013.01); *G01N 33/6854* (2013.01); *A61K 2039/5252* (2013.01); *C07K 2319/21* (2013.01); *C07K 2319/50* (2013.01); *C12N 2710/14021* (2013.01); *C12N 2710/14022* (2013.01); *C12N 2710/14043* (2013.01); *C12N 2710/14051* (2013.01); *C12N 2710/14143* (2013.01); *C12N 2750/10034* (2013.01); *C12N 2750/10051* (2013.01); *C12N 2760/16134* (2013.01); *C12N 2760/16151* (2013.01); *C12N 2760/20022* (2013.01); *C12N 2760/20034* (2013.01); *C12N 2760/20051* (2013.01); *G01N 2333/01* (2013.01)

(58) Field of Classification Search
None
See application file for complete search history.

(56) References Cited

U.S. PATENT DOCUMENTS

| | | | |
|---|---|---|---|
| 10,168,330 B2 * | 1/2019 | Iyer | A61K 39/12 |
| 2016/0258953 A1 | 9/2016 | Iyer et al. | |
| 2019/0154688 A1 * | 5/2019 | Iyer | A61K 39/12 |

FOREIGN PATENT DOCUMENTS

| | | |
|---|---|---|
| CN | 101884787 | 11/2010 |
| WO | 2009016433 | 2/2009 |
| WO | 2015051255 A1 | 4/2015 |

OTHER PUBLICATIONS

Ahmad et al., "Immunological Characterization of the VSV Nucleocapsid (N) Protein Expressed by Recombinant Baculovirus in Spodoptera exigua Larva: Use in Differential Diagnosis between Vaccinated and Infected Animals". Virology, vol. 192, 1993, pp. 207-216.
Anderson et al., "Purification, Stability, and Immunogenicity Analyses of Five Bluetongue Virus Proteins for Use in Development of a Subunit Vaccine That Allows Differentiation of Infected From Vaccinated Animals". Clinical and Vaccine Immunology, vol. 21, No. 3, Mar. 2014, pp. 443-452.
Faburay et al., "A Glycoprotein Subunit Vaccine Elicits a Strong Rift Valley Fever Virus Neutralizing Antibody Response in Sheep". Vector-Borne and Zoonotic Diseases, vol. 14, No. 10, 2014, pp. 746-756.
Geisler et al., "Rhabdovirus-like endogenous viral elements in the genome of Spodoptera frugiperda insect cells are actively transcribed: Implications for adventitious virus detection". Biologicals, vol. 44, No. 4, 2016, pp. 219-225.
Ma et al., "Identification of a Novel Rhabdovirus in spodoptera frugiperda Cell Lines". Journal of Virology, vol. 88, No. 12, Jun. 2014, pp. 6576-6585.
Maghodia et al., "Characterization of an Sf-rhabdovirus-negative Spodopter frugiperda cell line as an alternative host for recombinant protein production in the baculovirus-insect cell system". Protein Expression and Purification, vol. 122, 2016, pp. 45-55.
Stewart et al., "Validation of a novel approach for the rapid production of immunogenic virus-like particles for bluetongue virus". Vaccine, vol. 28, 2010, pp. 3047-3054.

(Continued)

*Primary Examiner* — Shanon A. Foley
(74) *Attorney, Agent, or Firm* — Judy Jarecki-Black

(57) ABSTRACT

The present invention belongs to the field of compliance markers and marker vaccines which allow for the differentiation between infected and vaccinated individuals. In particular, it relates to a method of determining whether an individual has received an immunogenic composition comprising a recombinant protein produced by a baculovirus expression system in cultured insect cells.

20 Claims, 8 Drawing Sheets

Figure 1:
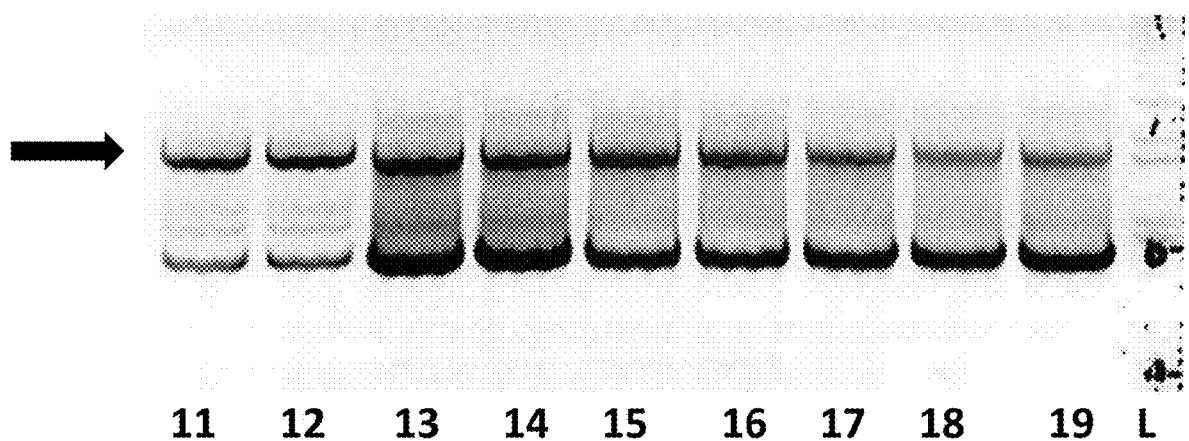

Specification includes a Sequence Listing.

(56) References Cited

OTHER PUBLICATIONS

Zhang et al., "Susceptibility of the Sf9 insect cell line to infection with adventitious viruses." Biologicals 22, No. 3 (1994): 205-213.
Anderson et al., "Evaluation of the immunogenicity of an experimental DIVA subunit vaccine against Bluetongue virus serotype 8 in cattle." Clinical and Vaccine Immunology. Aug. 2013; 20 (8): 1115-1122.
Saxena et al., "Pre-existing immunity against vaccine vectors—friend or foe?." Microbiology 159, No. 1 (2013): 1-11.
Pérez-Martín et al., "Immunity conferred by an experimental vaccine based on the recombinant PCV2 Cap protein expressed in Trichoplusia ni-larvae." Vaccine 28, No. 11 (2010): 2340-2349.

* cited by examiner

SEQUENCE LISTING

```
<160> NUMBER OF SEQ ID NOS: 30

<210> SEQ ID NO 1
<211> LENGTH: 610
<212> TYPE: PRT
<213> ORGANISM: Unknown
<220> FEATURE:
<223> OTHER INFORMATION: Sequence of a Spodoptera frugiperda rhabdovirus
      G protein

<400> SEQUENCE: 1

Met Val Phe Leu Ser Leu Ser Thr Ile Ile Phe Ile Leu Ser Leu Arg
1               5                   10                  15

Ala Val Thr Cys Ser Asn Pro Leu Ser Tyr Pro Asn Gly Ile Leu Thr
            20                  25                  30

Asn Asn Ser Thr His Asn His Pro Leu Ser Asp Phe Tyr Ile Phe Tyr
        35                  40                  45

Glu Asn Ser Ser Leu Thr Tyr Thr Gln Phe Pro Val Ala Pro Asp Cys
    50                  55                  60

Ser Ser Ile Leu Asp Thr Arg Asp Glu Gln Tyr Pro Thr Thr Val Thr
65                  70                  75                  80

Leu Trp Lys Val Asp Gln Glu Ser Gln Ala Glu Trp Gly Leu Leu Leu
                85                  90                  95

Trp Gln Glu Arg Ile Asp Thr Thr Cys Ser Trp Asn Phe Trp Gly Asn
            100                 105                 110
```

-continued

```
Tyr Lys Gly Ser Ile Val Ser Lys Ser Ser Val Pro Leu Lys Asp Ile
            115                 120                 125

Pro Ser Gly Ser Ala Arg Asn Gly Tyr Trp Ala Leu Ser Asn Asp Glu
130                 135                 140

Val Gln Glu Ile Asp His Val Pro Tyr Asn Leu Arg Tyr Tyr Cys Tyr
145                 150                 155                 160

Trp Cys Arg Asn Glu Tyr Pro Gly Ser Phe Tyr Met Arg Tyr Val Lys
                165                 170                 175

Lys Val Arg Ile Ile Arg Asn Pro Asp Gly Ser Ile Lys Thr Pro Arg
                180                 185                 190

Gly Ser Trp Val His Glu Leu Asp Asn Leu Trp Gly Asp Gln Met Arg
            195                 200                 205

Tyr Leu Val Ile Arg Arg Phe Gly Gly Glu Ser Ser Cys Pro Leu Lys
            210                 215                 220

Ile Tyr Asp Val Arg Ala Gly Val Leu Ser Lys Ser Arg Ser Asn Phe
225                 230                 235                 240

Ile Leu Val Ser Leu Pro Ser Leu Asn Leu Gln Phe Ser Val Ser Leu
                245                 250                 255

Glu Ser Thr Glu Thr Lys Cys Ser Phe Gly Asp Lys Thr Tyr Asp Ile
                260                 265                 270

Val Gln Ser Met Gly Gly Tyr Leu Leu Ser Ile Asp Ile Gly Asn Ala
            275                 280                 285

Asn Trp Arg Gly Pro Trp Asp Pro Thr Pro Gln His Pro Gly Arg Glu
            290                 295                 300

Arg Arg Ser Ile Met Glu Phe Pro Asp Gln Thr Ser Phe Arg Tyr Asn
305                 310                 315                 320

Gln Phe Ile Asn Tyr His Ser Ser Pro Arg His Lys Arg His Asp Gln
                325                 330                 335

Glu Phe Glu Phe Pro Leu Ser Leu Lys Ser Ser Tyr Asp Tyr Ala Gln
            340                 345                 350

Phe Arg Tyr Glu Gln Asn Phe Ile Ile Arg Gln Ile Asn Lys Asn Phe
            355                 360                 365

Gly Leu Leu Gln Lys Ser Ile Cys Asp Ile Gln Phe Ser Lys Trp Gln
            370                 375                 380

Asn Leu Ser Pro Pro Asn Leu Ala Met Lys Ile Ala His Tyr Val Thr
385                 390                 395                 400

Gly Ser Ile His Ser Ile Gly Gly Val His His Gly Ser Tyr Ser Ile
                405                 410                 415

Gln Arg Thr Glu Lys Ser Ile Thr Lys Val Asn Leu Val Phe Pro Ile
            420                 425                 430

Val Ile Val His Gly Met Tyr Lys Cys Gln Arg Glu Pro Ser Lys Glu
            435                 440                 445

Val Val Trp Ala Glu Pro Val Thr Gly Ile Leu Phe Lys Ser Pro Ile
450                 455                 460

Pro Thr His Phe Ser Leu Ser Ser Trp Leu Pro Gly Val Asn Gly
465                 470                 475                 480

Ser Ser Ile Val Pro Leu Thr Gly Gln Ile Leu Leu Pro Glu Ile Thr
                485                 490                 495

Met Asp His Leu Glu Val Val Gln Gln Val Glu Ala Lys Met Val Lys
            500                 505                 510

Ser Met Tyr Thr Asn Val Glu Leu Phe Gly Ser Thr Glu Glu Phe Gln
            515                 520                 525
```

Arg Tyr Gln Thr Gln Gly Ile Thr Ser Asp Glu Gln Ser Asn Thr Val
            530                 535                 540

Asn Pro Trp Ile Gly Leu Leu Ile His Gly Gly Val Ser Ile Ala Thr
545                 550                 555                 560

Gly Ile Leu Val Ala Leu Leu Ile Pro Ser Ile Leu Lys Leu Phe Arg
            565                 570                 575

His Ile Ile Glu Lys Gly Glu Ala Ser Leu Glu Glu Arg Leu His Leu
            580                 585                 590

Arg Glu Thr Ser Arg Lys Glu Phe Val Lys Val Arg Gly Lys Pro Trp
            595                 600                 605

Gly Val
    610

<210> SEQ ID NO 2
<211> LENGTH: 550
<212> TYPE: PRT
<213> ORGANISM: Artificial Sequence
<220> FEATURE:
<223> OTHER INFORMATION: Sequence of a truncated Spodoptera frugiperda
      rhabdovirus G protein

<400> SEQUENCE: 2

Met Val Phe Leu Ser Leu Ser Thr Ile Ile Phe Ile Leu Ser Leu Arg
1               5                   10                  15

Ala Val Thr Cys Ser Asn Pro Leu Ser Tyr Pro Asn Gly Ile Leu Thr
            20                  25                  30

Asn Asn Ser Thr His Asn His Pro Leu Ser Asp Phe Tyr Ile Phe Tyr
            35                  40                  45

Glu Asn Ser Ser Leu Thr Tyr Thr Gln Phe Pro Val Ala Pro Asp Cys
50                  55                  60

Ser Ser Ile Leu Asp Thr Arg Asp Glu Gln Tyr Pro Thr Thr Val Thr
65                  70                  75                  80

Leu Trp Lys Val Asp Gln Glu Ser Gln Ala Glu Trp Gly Leu Leu Leu
            85                  90                  95

Trp Gln Glu Arg Ile Asp Thr Thr Cys Ser Trp Asn Phe Trp Gly Asn
            100                 105                 110

Tyr Lys Gly Ser Ile Val Ser Lys Ser Val Pro Leu Lys Asp Ile
            115                 120                 125

Pro Ser Gly Ser Ala Arg Asn Gly Tyr Trp Ala Leu Ser Asn Asp Glu
            130                 135                 140

Val Gln Glu Ile Asp His Val Pro Tyr Asn Leu Arg Tyr Tyr Cys Tyr
145                 150                 155                 160

Trp Cys Arg Asn Glu Tyr Pro Gly Ser Phe Tyr Met Arg Tyr Val Lys
            165                 170                 175

Lys Val Arg Ile Ile Arg Asn Pro Asp Gly Ser Ile Lys Thr Pro Arg
            180                 185                 190

Gly Ser Trp Val His Glu Leu Asp Asn Leu Trp Gly Asp Gln Met Arg
            195                 200                 205

Tyr Leu Val Ile Arg Arg Phe Gly Gly Glu Ser Ser Cys Pro Leu Lys
            210                 215                 220

Ile Tyr Asp Val Arg Ala Gly Val Leu Ser Lys Ser Arg Ser Asn Phe
225                 230                 235                 240

Ile Leu Val Ser Leu Pro Ser Leu Asn Leu Gln Phe Ser Val Ser Leu
            245                 250                 255

Glu Ser Thr Glu Thr Lys Cys Ser Phe Gly Asp Lys Thr Tyr Asp Ile
            260                 265                 270

-continued

```
Val Gln Ser Met Gly Gly Tyr Leu Ser Ile Asp Ile Gly Asn Ala
            275                 280                 285
Asn Trp Arg Gly Pro Trp Asp Pro Thr Pro Gln His Pro Gly Arg Glu
290                 295                 300
Arg Arg Ser Ile Met Glu Phe Pro Asp Gln Thr Ser Phe Arg Tyr Asn
305                 310                 315                 320
Gln Phe Ile Asn Tyr His Ser Ser Pro Arg His Lys Arg His Asp Gln
                325                 330                 335
Glu Phe Glu Phe Pro Leu Ser Leu Lys Ser Ser Tyr Asp Tyr Ala Gln
            340                 345                 350
Phe Arg Tyr Glu Gln Asn Phe Ile Ile Arg Gln Ile Asn Lys Asn Phe
        355                 360                 365
Gly Leu Leu Gln Lys Ser Ile Cys Asp Ile Gln Phe Ser Lys Trp Gln
370                 375                 380
Asn Leu Ser Pro Pro Asn Leu Ala Met Lys Ile Ala His Tyr Val Thr
385                 390                 395                 400
Gly Ser Ile His Ser Ile Gly Gly Val His His Gly Ser Tyr Ser Ile
                405                 410                 415
Gln Arg Thr Glu Lys Ser Ile Thr Lys Val Asn Leu Val Phe Pro Ile
            420                 425                 430
Val Ile Val His Gly Met Tyr Lys Cys Gln Arg Glu Pro Ser Lys Glu
        435                 440                 445
Val Val Trp Ala Glu Pro Val Thr Gly Ile Leu Phe Lys Ser Pro Ile
450                 455                 460
Pro Thr His Phe Ser Leu Ser Ser Ser Trp Leu Pro Gly Val Asn Gly
465                 470                 475                 480
Ser Ser Ile Val Pro Leu Thr Gly Gln Ile Leu Leu Pro Glu Ile Thr
                485                 490                 495
Met Asp His Leu Glu Val Val Gln Gln Val Glu Ala Lys Met Val Lys
            500                 505                 510
Ser Met Tyr Thr Asn Val Glu Leu Phe Gly Ser Thr Glu Glu Phe Gln
        515                 520                 525
Arg Tyr Gln Thr Gln Gly Ile Thr Ser Asp Glu Gln Ser Asn Thr Val
530                 535                 540
Asn Pro Trp Ile Gly Leu
545                 550

<210> SEQ ID NO 3
<211> LENGTH: 618
<212> TYPE: PRT
<213> ORGANISM: Artificial Sequence
<220> FEATURE:
<223> OTHER INFORMATION: Sequence of a truncated Spodoptera frugiperda
      rhabdovirus G protein with an N-terminal melittin peptide

<400> SEQUENCE: 3

Met Lys Phe Leu Val Asn Val Ala Leu Val Phe Met Val Val Tyr Ile
1               5                   10                  15
Ser Tyr Ile Tyr Ala Asn Pro Leu Ser Tyr Pro Asn Gly Asn Pro Leu
            20                  25                  30
Ser Tyr Pro Asn Gly Ile Leu Thr Asn Ser Thr His Asn His Pro
        35                  40                  45
Leu Ser Asp Phe Tyr Ile Phe Tyr Glu Asn Ser Ser Leu Thr Tyr Thr
    50                  55                  60
Gln Phe Pro Val Ala Pro Asp Cys Ser Ser Ile Leu Asp Thr Arg Asp
65                  70                  75                  80
```

-continued

```
Glu Gln Tyr Pro Thr Thr Val Thr Leu Trp Lys Val Asp Gln Glu Ser
             85                  90                  95
Gln Ala Glu Trp Gly Leu Leu Leu Trp Gln Glu Arg Ile Asp Thr Thr
        100                 105                 110
Cys Ser Trp Asn Phe Trp Gly Asn Tyr Lys Gly Ser Ile Val Ser Lys
        115                 120                 125
Ser Ser Val Pro Leu Lys Asp Ile Pro Ser Gly Ser Ala Arg Asn Gly
        130                 135                 140
Tyr Trp Ala Leu Ser Asn Asp Glu Val Gln Glu Ile Asp His Val Pro
145                 150                 155                 160
Tyr Asn Leu Arg Tyr Tyr Cys Tyr Trp Cys Arg Asn Glu Tyr Pro Gly
                165                 170                 175
Ser Phe Tyr Met Arg Tyr Val Lys Lys Val Arg Ile Ile Arg Asn Pro
            180                 185                 190
Asp Gly Ser Ile Lys Thr Pro Arg Gly Ser Trp Val His Glu Leu Asp
            195                 200                 205
Asn Leu Trp Gly Asp Gln Met Arg Tyr Leu Val Ile Arg Arg Phe Gly
        210                 215                 220
Gly Glu Ser Ser Cys Pro Leu Lys Ile Tyr Asp Val Arg Ala Gly Val
225                 230                 235                 240
Leu Ser Lys Ser Arg Ser Asn Phe Ile Leu Val Ser Leu Pro Ser Leu
                245                 250                 255
Asn Leu Gln Phe Ser Val Ser Leu Glu Ser Thr Glu Thr Lys Cys Ser
            260                 265                 270
Phe Gly Asp Lys Thr Tyr Asp Ile Val Gln Ser Met Gly Gly Tyr Leu
            275                 280                 285
Leu Ser Ile Asp Ile Gly Asn Ala Asn Trp Arg Gly Pro Trp Asp Pro
        290                 295                 300
Thr Pro Gln His Pro Gly Arg Glu Arg Ser Ile Met Glu Phe Pro
305                 310                 315                 320
Asp Gln Thr Ser Phe Arg Tyr Asn Gln Phe Ile Asn Tyr His Ser Ser
                325                 330                 335
Pro Arg His Lys Arg His Asp Gln Glu Phe Glu Phe Pro Leu Ser Leu
            340                 345                 350
Lys Ser Ser Tyr Asp Tyr Ala Gln Phe Arg Tyr Glu Gln Asn Phe Ile
            355                 360                 365
Ile Arg Gln Ile Asn Lys Asn Phe Gly Leu Leu Gln Lys Ser Ile Cys
        370                 375                 380
Asp Ile Gln Phe Ser Lys Trp Gln Asn Leu Ser Pro Pro Asn Leu Ala
385                 390                 395                 400
Met Lys Ile Ala His Tyr Val Thr Gly Ser Ile His Ser Ile Gly Gly
                405                 410                 415
Val His His Gly Ser Tyr Ser Ile Gln Arg Thr Glu Lys Ser Ile Thr
            420                 425                 430
Lys Val Asn Leu Val Phe Pro Ile Val Ile His Gly Met Tyr Lys
            435                 440                 445
Cys Gln Arg Glu Pro Ser Lys Val Val Trp Ala Glu Pro Val Thr
        450                 455                 460
Gly Ile Leu Phe Lys Ser Pro Ile Pro Thr His Phe Ser Leu Ser Ser
465                 470                 475                 480
Ser Trp Leu Pro Gly Val Asn Gly Ser Ser Ile Val Pro Leu Thr Gly
                485                 490                 495
```

-continued

```
Gln Ile Leu Leu Pro Glu Ile Thr Met Asp His Leu Glu Val Val Gln
                500                 505                 510

Gln Val Glu Ala Lys Met Val Lys Ser Met Tyr Thr Asn Val Glu Leu
            515                 520                 525

Phe Gly Ser Thr Glu Glu Phe Gln Arg Tyr Gln Thr Gln Gly Ile Thr
        530                 535                 540

Ser Asp Glu Gln Ser Asn Thr Val Asn Pro Trp Ile Gly Leu Leu Ile
545                 550                 555                 560

His Gly Gly Val Ser Ile Ala Thr Gly Ile Leu Val Ala Leu Leu Ile
                565                 570                 575

Pro Ser Ile Leu Lys Leu Phe Arg His Ile Ile Glu Lys Gly Glu Ala
            580                 585                 590

Ser Leu Glu Glu Arg Leu His Leu Arg Glu Thr Ser Arg Lys Glu Phe
        595                 600                 605

Val Lys Val Arg Gly Lys Pro Trp Gly Val
    610                 615
```

<210> SEQ ID NO 4
<211> LENGTH: 623
<212> TYPE: PRT
<213> ORGANISM: Artificial Sequence
<220> FEATURE:
<223> OTHER INFORMATION: Sequence of a Spodoptera frugiperda rhabdovirus
      G protein modified to include a 6x His tag

<400> SEQUENCE: 4

```
Met Val Phe Leu Ser Leu Ser Thr Ile Ile Phe Ile Leu Ser Leu Arg
1               5                   10                  15

Ala Val Thr Cys Ser Asn Pro Leu Ser Tyr Pro Asn Gly Ile Leu Thr
            20                  25                  30

Asn Asn Ser Thr His Asn His Pro Leu Ser Asp Phe Tyr Ile Phe Tyr
        35                  40                  45

Glu Asn Ser Ser Leu Thr Tyr Thr Gln Phe Pro Val Ala Pro Asp Cys
    50                  55                  60

Ser Ser Ile Leu Asp Thr Arg Asp Glu Gln Tyr Pro Thr Thr Val Thr
65                  70                  75                  80

Leu Trp Lys Val Asp Gln Glu Ser Gln Ala Glu Trp Gly Leu Leu Leu
                85                  90                  95

Trp Gln Glu Arg Ile Asp Thr Thr Cys Ser Trp Asn Phe Trp Gly Asn
            100                 105                 110

Tyr Lys Gly Ser Ile Val Ser Lys Ser Ser Val Pro Leu Lys Asp Ile
        115                 120                 125

Pro Ser Gly Ser Ala Arg Asn Gly Tyr Trp Ala Leu Ser Asn Asp Glu
    130                 135                 140

Val Gln Glu Ile Asp His Val Pro Tyr Asn Leu Arg Tyr Tyr Cys Tyr
145                 150                 155                 160

Trp Cys Arg Asn Glu Tyr Pro Gly Ser Phe Tyr Met Arg Tyr Val Lys
                165                 170                 175

Lys Val Arg Ile Ile Arg Asn Pro Asp Gly Ser Ile Lys Thr Pro Arg
            180                 185                 190

Gly Ser Trp Val His Glu Leu Asp Asn Leu Trp Gly Asp Gln Met Arg
        195                 200                 205

Tyr Leu Val Ile Arg Arg Phe Gly Gly Glu Ser Ser Cys Pro Leu Lys
    210                 215                 220

Ile Tyr Asp Val Arg Ala Gly Val Leu Ser Lys Ser Arg Ser Asn Phe
225                 230                 235                 240
```

```
Ile Leu Val Ser Leu Pro Ser Leu Asn Leu Gln Phe Ser Val Ser Leu
                245                 250                 255

Glu Ser Thr Glu Thr Lys Cys Ser Phe Gly Asp Lys Thr Tyr Asp Ile
            260                 265                 270

Val Gln Ser Met Gly Gly Tyr Leu Leu Ser Ile Asp Ile Gly Asn Ala
        275                 280                 285

Asn Trp Arg Gly Pro Trp Asp Pro Thr Pro Gln His Pro Gly Arg Glu
    290                 295                 300

Arg Arg Ser Ile Met Glu Phe Pro Asp Gln Thr Ser Phe Arg Tyr Asn
305                 310                 315                 320

Gln Phe Ile Asn Tyr His Ser Ser Pro Arg His Lys Arg His Asp Gln
                325                 330                 335

Glu Phe Glu Phe Pro Leu Ser Leu Lys Ser Ser Tyr Asp Tyr Ala Gln
            340                 345                 350

Phe Arg Tyr Glu Gln Asn Phe Ile Ile Arg Gln Ile Asn Lys Asn Phe
        355                 360                 365

Gly Leu Leu Gln Lys Ser Ile Cys Asp Ile Gln Phe Ser Lys Trp Gln
    370                 375                 380

Asn Leu Ser Pro Pro Asn Leu Ala Met Lys Ile Ala His Tyr Val Thr
385                 390                 395                 400

Gly Ser Ile His Ser Ile Gly Gly Val His His Gly Ser Tyr Ser Ile
                405                 410                 415

Gln Arg Thr Glu Lys Ser Ile Thr Lys Val Asn Leu Val Phe Pro Ile
            420                 425                 430

Val Ile Val His Gly Met Tyr Lys Cys Gln Arg Glu Pro Ser Lys Glu
        435                 440                 445

Val Val Trp Ala Glu Pro Val Thr Gly Ile Leu Phe Lys Ser Pro Ile
    450                 455                 460

Pro Thr His Phe Ser Leu Ser Ser Ser Trp Leu Pro Gly Val Asn Gly
465                 470                 475                 480

Ser Ser Ile Val Pro Leu Thr Gly Gln Ile Leu Leu Pro Glu Ile Thr
                485                 490                 495

Met Asp His Leu Glu Val Val Gln Gln Val Glu Ala Lys Met Val Lys
            500                 505                 510

Ser Met Tyr Thr Asn Val Glu Leu Phe Gly Ser Thr Glu Glu Phe Gln
        515                 520                 525

Arg Tyr Gln Thr Gln Gly Ile Thr Ser Asp Glu Gln Ser Asn Thr Val
    530                 535                 540

Asn Pro Trp Ile Gly Leu Leu Ile His Gly Gly Val Ser Ile Ala Thr
545                 550                 555                 560

Gly Ile Leu Val Ala Leu Leu Ile Pro Ser Ile Leu Lys Leu Phe Arg
                565                 570                 575

His Ile Ile Glu Lys Gly Glu Ala Ser Leu Glu Glu Arg Leu His Leu
            580                 585                 590

Arg Glu Thr Ser Arg Lys Glu Phe Val Lys Val Arg Gly Lys Pro Trp
        595                 600                 605

Gly Val Glu Asn Leu Tyr Phe Gln Gly His His His His His His
    610                 615                 620

<210> SEQ ID NO 5
<211> LENGTH: 563
<212> TYPE: PRT
<213> ORGANISM: Artificial Sequence
```

<220> FEATURE:
<223> OTHER INFORMATION: Sequence of a truncated Spodoptera frugiperda
    rhabdovirus G protein modified to include a 6x His tag

<400> SEQUENCE: 5

```
Met Val Phe Leu Ser Leu Ser Thr Ile Ile Phe Ile Leu Ser Leu Arg
 1               5                  10                  15

Ala Val Thr Cys Ser Asn Pro Leu Ser Tyr Pro Asn Gly Ile Leu Thr
            20                  25                  30

Asn Asn Ser Thr His Asn His Pro Leu Ser Asp Phe Tyr Ile Phe Tyr
        35                  40                  45

Glu Asn Ser Ser Leu Thr Tyr Thr Gln Phe Pro Val Ala Pro Asp Cys
50                  55                  60

Ser Ser Ile Leu Asp Thr Arg Asp Glu Gln Tyr Pro Thr Thr Val Thr
65                  70                  75                  80

Leu Trp Lys Val Asp Gln Glu Ser Gln Ala Glu Trp Gly Leu Leu Leu
                85                  90                  95

Trp Gln Glu Arg Ile Asp Thr Thr Cys Ser Trp Asn Phe Trp Gly Asn
            100                 105                 110

Tyr Lys Gly Ser Ile Val Ser Lys Ser Ser Val Pro Leu Lys Asp Ile
        115                 120                 125

Pro Ser Gly Ser Ala Arg Asn Gly Tyr Trp Ala Leu Ser Asn Asp Glu
    130                 135                 140

Val Gln Glu Ile Asp His Val Pro Tyr Asn Leu Arg Tyr Tyr Cys Tyr
145                 150                 155                 160

Trp Cys Arg Asn Glu Tyr Pro Gly Ser Phe Tyr Met Arg Tyr Val Lys
                165                 170                 175

Lys Val Arg Ile Ile Arg Asn Pro Asp Gly Ser Ile Lys Thr Pro Arg
            180                 185                 190

Gly Ser Trp Val His Glu Leu Asp Asn Leu Trp Gly Asp Gln Met Arg
        195                 200                 205

Tyr Leu Val Ile Arg Arg Phe Gly Gly Glu Ser Ser Cys Pro Leu Lys
    210                 215                 220

Ile Tyr Asp Val Arg Ala Gly Val Leu Ser Lys Ser Arg Ser Asn Phe
225                 230                 235                 240

Ile Leu Val Ser Leu Pro Ser Leu Asn Leu Gln Phe Ser Val Ser Leu
                245                 250                 255

Glu Ser Thr Glu Thr Lys Cys Ser Phe Gly Asp Lys Tyr Asp Ile
            260                 265                 270

Val Gln Ser Met Gly Gly Tyr Leu Leu Ser Ile Asp Ile Gly Asn Ala
        275                 280                 285

Asn Trp Arg Gly Pro Trp Asp Pro Thr Pro Gln His Pro Gly Arg Glu
    290                 295                 300

Arg Arg Ser Ile Met Glu Phe Pro Asp Gln Thr Ser Phe Arg Tyr Asn
305                 310                 315                 320

Gln Phe Ile Asn Tyr His Ser Ser Pro Arg His Lys Arg His Asp Gln
                325                 330                 335

Glu Phe Glu Phe Pro Leu Ser Leu Lys Ser Ser Tyr Tyr Ala Gln
            340                 345                 350

Phe Arg Tyr Glu Gln Asn Phe Ile Ile Arg Gln Ile Asn Lys Asn Phe
    355                 360                 365

Gly Leu Leu Gln Lys Ser Ile Cys Asp Ile Gln Phe Ser Lys Trp Gln
370                 375                 380
```

-continued

```
Asn Leu Ser Pro Pro Asn Leu Ala Met Lys Ile Ala His Tyr Val Thr
385                 390                 395                 400

Gly Ser Ile His Ser Ile Gly Gly Val His His Gly Ser Tyr Ser Ile
            405                 410                 415

Gln Arg Thr Glu Lys Ser Ile Thr Lys Val Asn Leu Val Phe Pro Ile
        420                 425                 430

Val Ile Val His Gly Met Tyr Lys Cys Gln Arg Glu Pro Ser Lys Glu
            435                 440                 445

Val Val Trp Ala Glu Pro Val Thr Gly Ile Leu Phe Lys Ser Pro Ile
        450                 455                 460

Pro Thr His Phe Ser Leu Ser Ser Ser Trp Leu Pro Gly Val Asn Gly
465                 470                 475                 480

Ser Ser Ile Val Pro Leu Thr Gly Gln Ile Leu Leu Pro Glu Ile Thr
            485                 490                 495

Met Asp His Leu Glu Val Val Gln Gln Val Glu Ala Lys Met Val Lys
            500                 505                 510

Ser Met Tyr Thr Asn Val Glu Leu Phe Gly Ser Thr Glu Phe Gln
        515                 520                 525

Arg Tyr Gln Thr Gln Gly Ile Thr Ser Asp Glu Gln Ser Asn Thr Val
530                 535                 540

Asn Pro Trp Ile Gly Leu Glu Asn Leu Tyr Phe Gln Gly His His His
545                 550                 555                 560

His His His
```

<210> SEQ ID NO 6
<211> LENGTH: 631
<212> TYPE: PRT
<213> ORGANISM: Artificial Sequence
<220> FEATURE:
<223> OTHER INFORMATION: Sequence of a truncated Spodoptera frugiperda
      rhabdovirus G protein with an N-terminal melittin peptide and
      modified to include a 6x His tag

<400> SEQUENCE: 6

```
Met Lys Phe Leu Val Asn Val Ala Leu Val Phe Met Val Val Tyr Ile
1               5                   10                  15

Ser Tyr Ile Tyr Ala Asn Pro Leu Ser Tyr Pro Asn Gly Asn Pro Leu
            20                  25                  30

Ser Tyr Pro Asn Gly Ile Leu Thr Asn Asn Ser Thr His Asn His Pro
        35                  40                  45

Leu Ser Asp Phe Tyr Ile Phe Tyr Glu Asn Ser Ser Leu Thr Tyr Thr
50                  55                  60

Gln Phe Pro Val Ala Pro Asp Cys Ser Ser Ile Leu Asp Thr Arg Asp
65                  70                  75                  80

Glu Gln Tyr Pro Thr Thr Val Thr Leu Trp Lys Val Asp Gln Glu Ser
                85                  90                  95

Gln Ala Glu Trp Gly Leu Leu Leu Trp Gln Glu Arg Ile Asp Thr Thr
            100                 105                 110

Cys Ser Trp Asn Phe Trp Gly Asn Tyr Lys Gly Ser Ile Val Ser Lys
        115                 120                 125

Ser Ser Val Pro Leu Lys Asp Ile Pro Ser Gly Ser Ala Arg Asn Gly
130                 135                 140

Tyr Trp Ala Leu Ser Asn Asp Glu Val Gln Glu Ile Asp His Val Pro
145                 150                 155                 160

Tyr Asn Leu Arg Tyr Tyr Cys Tyr Trp Cys Arg Asn Glu Tyr Pro Gly
                165                 170                 175
```

```
Ser Phe Tyr Met Arg Tyr Val Lys Lys Val Arg Ile Ile Arg Asn Pro
            180                 185                 190

Asp Gly Ser Ile Lys Thr Pro Arg Gly Ser Trp Val His Glu Leu Asp
        195                 200                 205

Asn Leu Trp Gly Asp Gln Met Arg Tyr Leu Val Ile Arg Arg Phe Gly
    210                 215                 220

Gly Glu Ser Ser Cys Pro Leu Lys Ile Tyr Asp Val Arg Ala Gly Val
225                 230                 235                 240

Leu Ser Lys Ser Arg Ser Asn Phe Ile Leu Val Ser Leu Pro Ser Leu
                245                 250                 255

Asn Leu Gln Phe Ser Val Ser Leu Glu Ser Thr Glu Thr Lys Cys Ser
            260                 265                 270

Phe Gly Asp Lys Thr Tyr Asp Ile Val Gln Ser Met Gly Gly Tyr Leu
        275                 280                 285

Leu Ser Ile Asp Ile Gly Asn Ala Asn Trp Arg Gly Pro Trp Asp Pro
    290                 295                 300

Thr Pro Gln His Pro Gly Arg Glu Arg Ser Ile Met Glu Phe Pro
305                 310                 315                 320

Asp Gln Thr Ser Phe Arg Tyr Asn Gln Phe Ile Asn Tyr His Ser Ser
                325                 330                 335

Pro Arg His Lys Arg His Asp Gln Glu Phe Glu Phe Pro Leu Ser Leu
            340                 345                 350

Lys Ser Ser Tyr Asp Tyr Ala Gln Phe Arg Tyr Glu Gln Asn Phe Ile
        355                 360                 365

Ile Arg Gln Ile Asn Lys Asn Phe Gly Leu Leu Gln Lys Ser Ile Cys
    370                 375                 380

Asp Ile Gln Phe Ser Lys Trp Gln Asn Leu Ser Pro Pro Asn Leu Ala
385                 390                 395                 400

Met Lys Ile Ala His Tyr Val Thr Gly Ser Ile His Ser Ile Gly Gly
                405                 410                 415

Val His His Gly Ser Tyr Ser Ile Gln Arg Thr Glu Lys Ser Ile Thr
            420                 425                 430

Lys Val Asn Leu Val Phe Pro Ile Val Ile His Gly Met Tyr Lys
        435                 440                 445

Cys Gln Arg Glu Pro Ser Lys Glu Val Val Trp Ala Glu Pro Val Thr
    450                 455                 460

Gly Ile Leu Phe Lys Ser Pro Ile Pro Thr His Phe Ser Leu Ser Ser
465                 470                 475                 480

Ser Trp Leu Pro Gly Val Asn Gly Ser Ser Ile Val Pro Leu Thr Gly
                485                 490                 495

Gln Ile Leu Leu Pro Glu Ile Thr Met Asp His Leu Glu Val Val Gln
            500                 505                 510

Gln Val Glu Ala Lys Met Val Lys Ser Met Tyr Thr Asn Val Glu Leu
        515                 520                 525

Phe Gly Ser Thr Glu Glu Phe Gln Arg Tyr Gln Thr Gln Gly Ile Thr
    530                 535                 540

Ser Asp Glu Gln Ser Asn Thr Val Asn Pro Trp Ile Gly Leu Leu Ile
545                 550                 555                 560

His Gly Gly Val Ser Ile Ala Thr Gly Ile Leu Val Ala Leu Leu Ile
                565                 570                 575

Pro Ser Ile Leu Lys Leu Phe Arg His Ile Ile Glu Lys Gly Glu Ala
            580                 585                 590
```

-continued

```
Ser Leu Glu Glu Arg Leu His Leu Arg Glu Thr Ser Arg Lys Glu Phe
            595                 600                 605
Val Lys Val Arg Gly Lys Pro Trp Gly Val Glu Asn Leu Tyr Phe Gln
610                 615                 620
Gly His His His His His
625                 630

<210> SEQ ID NO 7
<211> LENGTH: 521
<212> TYPE: PRT
<213> ORGANISM: Unknown
<220> FEATURE:
<223> OTHER INFORMATION: Sequence of a Spodoptera frugiperda rhabdovirus
      N protein

<400> SEQUENCE: 7

Met Thr Gln Gly Thr Met Lys Pro Val Trp Glu Glu Leu Gly Thr Gly
1               5                   10                  15
Glu Thr Glu Phe Gln Gly Thr Val Asp Ile Pro Gly Arg Ser Leu Lys
            20                  25                  30
Pro Glu Lys Thr Asp Trp Ser Val Asp Thr Cys Arg Glu Ile Ser Leu
        35                  40                  45
Asn Leu Lys Leu Pro Gly Glu Ile Trp Gln Leu Ala His Gln Glu Thr
    50                  55                  60
Ile Phe Asn Arg Phe Leu Thr Phe Tyr Ala Thr Gly Tyr Val Pro Asn
65                  70                  75                  80
Thr His Thr Ala Thr Glu Ile Val Leu Ser Met Ala Ser Leu Ile Phe
                85                  90                  95
Lys Asp Lys Ala Lys Ala Pro Ile Asp Leu Ile Trp Asp Asp Ser Phe
            100                 105                 110
Gln Ala Ser Pro Ser Glu Glu Cys Gly Phe Ser Val Val Gly Glu Thr
        115                 120                 125
Pro Leu Val Ile Gly Gln His Pro Asp Asp Asp Tyr Thr Leu Arg
    130                 135                 140
Glu Asp Glu Glu Ser Ala Ala Met Asn Glu Glu Lys Ile Gln Ala
145                 150                 155                 160
Ala Leu Lys Thr Leu Gly Ile Gln Asp Thr Pro Val Asp Leu Lys Asp
                165                 170                 175
Ala Ser Gly Ile Val Phe Glu Thr Lys Glu Asp Arg Glu Gln Arg Ile
            180                 185                 190
Lys Asn Glu Lys Ala Leu His Val Glu Asp Asp Ile Asn Ala Leu Thr
        195                 200                 205
Gln Ile Thr Lys Gln Phe Leu Phe Glu Tyr Ser Thr Gly Ser Leu Gln
    210                 215                 220
Lys Phe Val Ala Lys Ala Thr Thr Ile Phe Ile Asp Asn Asn Ala Thr
225                 230                 235                 240
Asn Gly Phe Thr Arg Leu His Leu His Ala Ile Arg Val Met Asn Phe
                245                 250                 255
Ile Ala Leu Thr Met Leu Arg Lys Val Thr Lys Ser Asn Ala Gln Met
            260                 265                 270
Ile Asn Ala Phe Leu Lys Glu Gln Tyr Lys Arg Asn Ile Ala Ser Leu
        275                 280                 285
Ile Pro Gly Ala Leu Ser Ser Asp Phe Ala Pro Pro Ser Lys Ser Cys
    290                 295                 300
Ile Asp Lys Leu Thr Ala Ile Ser Lys Asn Asp Pro Ala Val Ser Ser
305                 310                 315                 320
```

-continued

```
Phe Phe Ala Lys Val Val Met Leu Asn Met Glu Glu Arg Arg Asn
                325                 330                 335

Pro Ser Leu Val Ala Cys Leu Gly Ala Ser Leu Leu Thr His Thr Thr
            340                 345                 350

Trp Asn Gly Met Gly Ile Leu His Val Ile Phe Glu Val Cys Leu Phe
            355                 360                 365

His Gln Ile Ser Trp Lys Arg Leu Val Thr Glu Ser Leu Thr Ser Leu
            370                 375                 380

Thr Lys Met Ser Trp Gly Glu Val Ser Gln Phe Leu Ile Lys Tyr Gln
385                 390                 395                 400

Ala Lys Gly Asn Pro Asp Pro Thr Val Ala Trp Ala Arg Ile Ile Asp
                405                 410                 415

Asp Ser Tyr Phe Met Arg Leu Thr Ile Val Asn His Pro Thr Leu Ala
            420                 425                 430

Ala Leu Leu Val Glu Ser Leu Ile Arg Ser Gln Lys Asp Asp Gly Ile
            435                 440                 445

Leu Asn Ala Asn Trp Ala Ile Gln His Arg Asp Thr Ile Asn Tyr Tyr
            450                 455                 460

Arg Asp Ala Ala L

```
Ala Leu Lys Thr Leu Gly Ile Gln Asp Thr Pro Val Asp Leu Lys Asp
            165                 170                 175

Ala Ser Gly Ile Val Phe Glu Thr Lys Glu Asp Arg Glu Gln Arg Ile
        180                 185                 190

Lys Asn Glu Lys Ala Leu His Val Glu Asp Ile Asn Ala Leu Thr
        195                 200                 205

Gln Ile Thr Lys Gln Phe Leu Phe Glu Tyr Ser Thr Gly Ser Leu Gln
    210                 215                 220

Lys Phe Val Ala Lys Ala Thr Thr Ile Phe Asp Asn Asn Ala Thr
225                 230                 235                 240

Asn Gly Phe Thr Arg Leu His Leu His Ala Ile Arg Val Met Asn Phe
                245                 250                 255

Ile Ala Leu Thr Met Leu Arg Lys Val Thr Lys Ser Asn Ala Gln Met
            260                 265                 270

Ile Asn Ala Phe Leu Lys Glu Gln Tyr Lys Arg Asn Ile Ala Ser Leu
        275                 280                 285

Ile Pro Gly Ala Leu Ser Ser Asp Phe Ala Pro Ser Lys Ser Cys
    290                 295                 300

Ile Asp Lys Leu Thr Ala Ile Ser Lys Asn Asp Pro Ala Val Ser Ser
305                 310                 315                 320

Phe Phe Ala Lys Val Val Met Leu Asn Met Glu Glu Arg Arg Asn
                325                 330                 335

Pro Ser Leu Val Ala Cys Leu Gly Ala Ser Leu Leu Thr His Thr Thr
            340                 345                 350

Trp Asn Gly Met Gly Ile Leu His Val Ile Phe Glu Val Cys Leu Phe
        355                 360                 365

His Gln Ile Ser Trp Lys Arg Leu Val Thr Glu Ser Leu Thr Ser Leu
    370                 375                 380

Thr Lys Met Ser Trp Gly Glu Val Ser Gln Phe Leu Ile Lys Tyr Gln
385                 390                 395                 400

Ala Lys Gly Asn Pro Asp Pro Thr Val Ala Trp Ala Arg Ile Ile Asp
                405                 410                 415

Asp Ser Tyr Phe Met Arg Leu Thr Ile Val Asn His Pro Thr Leu Ala
            420                 425                 430

Ala Leu Leu Val Glu Ser Leu Ile Arg Ser Gln Lys Asp Asp Gly Ile
        435                 440                 445

Leu Asn Ala Asn Trp Ala Ile Gln His Arg Asp Thr Ile Asn Tyr Tyr
    450                 455                 460

Arg Asp Ala Ala Lys Leu Leu Thr Asp Lys Leu Thr Gly Gln Thr Ala
465                 470                 475                 480

Thr Val Gln Ala Leu Thr Asn Glu Ala Ala Asp Leu Val Arg Thr Met
                485                 490                 495

Asn Ala Gly Pro Ser Arg Tyr His Pro Arg Pro Ser Thr Leu Ile Pro
            500                 505                 510

Met Val Asp Leu Asn Pro Glu Asp Leu Glu Asn Leu Tyr Phe Gln Gly
        515                 520                 525

His His His His His His
    530

<210> SEQ ID NO 9
<211> LENGTH: 1830
<212> TYPE: DNA
<213> ORGANISM: Unknown
```

<220> FEATURE:
<223> OTHER INFORMATION: Nucleic acid sequence encoding a Spodoptera
frugiperda rhabdovirus G protein

<400> SEQUENCE: 9

```
atggttttct taagtttatc aacgatcata tttatcctaa gcctccgggc tgtaacctgc      60
tccaatcctc tctcctatcc taatggcatt ttgactaaca actctactca caatcatccc     120
ctatcggact tttatatttt ttatgagaac agttcccttg cctatactca attccctgtg     180
gccccagact gctctagtat tctagatact agagatgagc agtatcccac cactgttact     240
ttgtggaagg ttgatcaaga atctcaagct gagtggggac tccttttatg gcaagagaga     300
attgacacca cttgctcctg gaacttctgg ggcaattaca aaggatccat gtatctaaaa     360
tcctcagtac ctctaaagga tatcccatcg gtagtgccc ggaatggata ttgggctttg      420
agcaatgatg aagttcaaga gattgatcat gtcccttaca acttgagata ttattgttac     480
tggtgcagaa atgaatatcc tgggagcttt tatatgagat atgtaaagaa agttcggatc     540
ataagaaatc ctgatgggtc tataaagact cctagaggat cctgggttca tgagttggac     600
aacttgtggg gagatcagat gaggtatcta gttattcgaa gatttggggg agaatctagc     660
tgccctctta agatatatga tgtgagagca ggggttctgt caaaatctcg gtcaaacttc     720
atcttagtgt cccttccctc cttgaatttg cagttctctg tatcacttga atccactgag     780
acgaaatgct catttggaga taagacatat gatattgtgc agagcatggg aggctatctc     840
ctctccatcg acataggtaa tgcgaactgg cgaggccctt gggatcctac ccctcagcat     900
ccgggtcgtg aaagaagatc aattatggag tttccggatc aaacatcttt cagatataac     960
caatttataa attatcactc atccccaaga cacaagagac atgatcaaga atttgagttc    1020
cctctcagtc taaaatccag ttatgattat gctcaattta gatatgagca gaatttcatc    1080
atccgacaga tcaataagaa ttttggatta ttacagaaga gcatttgtga tattcagttt    1140
tctaagtggc agaatctcag tccacccaat cttgctatga aaattgccca ttatgtcacc    1200
ggctctatcc actctatagg tggtgttcat catggatctt attcaattca agaacggaa     1260
aaatccatta ctaaggtcaa tctggtgttt cccattgtta ttgttcatgg aatgtataag    1320
tgccaaaggg aaccatccaa ggaggtggtt tgggcagaac ccgtcacagg gatcttattc    1380
aagtctccta ttccgactca tttctcacta agttcctctt ggctacctgg ggtaaatggt    1440
tcttctattg tccctctgac aggtcaaatt cttctccctg aaatcacaat ggatcacttg    1500
gaggttgtac aacaggttga agcaaagatg gtcaaaagta tgtacacgaa tgtagagttg    1560
tttggatcaa cagaggaatt tcaaagatac caaactcagg gaattacctc tgatgaacaa    1620
tcaaatacag taaatccttg gattgggctt ttgatacatg gtggagtgtc catagctact    1680
ggaatattag tagcactttt gatcccctca atcttaaaat tgttcagaca tataattgag    1740
aaaggggagg catcgttaga ggagaggttg catctgaggg aaacctcaag aaaagaattt    1800
gtcaaggtta ggggggaaacc atggggtgtc                                    1830
```

<210> SEQ ID NO 10
<211> LENGTH: 1650
<212> TYPE: DNA
<213> ORGANISM: Artificial Sequence
<220> FEATURE:
<223> OTHER INFORMATION: Nucleic acid sequence encoding a truncated
Spodoptera frugiperda rhabdovirus G protein

<400> SEQUENCE: 10

```
atggttttct taagtttatc aacgatcata tttatcctaa gcctccgggc tgtaacctgc      60
tccaatcctc tctcctatcc taatggcatt ttgactaaca actctactca caatcatccc     120
ctatcggact tttatatttt ttatgagaac agttcccta cctatactca attccctgtg      180
gccccagact gctctagtat tctagatact agagatgagc agtatcccac cactgttact     240
ttgtggaagg ttgatcaaga atctcaagct gagtggggac tccttttatg caagagaga     300
attgacacca cttgctcctg gaacttctgg ggcaattaca aaggatccat tgtatctaaa     360
tcctcagtac ctctaaagga tatcccatcg ggtagtgccc ggaatggata ttgggcttg     420
agcaatgatg aagttcaaga gattgatcat gtcccttaca acttgagata ttattgttac     480
tggtgcagaa atgaatatcc tgggagcttt tatatgagat atgtaaagaa agttcggatc     540
ataagaaatc ctgatgggtc tataaagact cctagaggat cctgggttca tgagttggac     600
aacttgtggg gagatcagat gaggtatcta gttattcgaa gatttggggg agaatctagc     660
tgccctctta agatatatga tgtgagagca ggggttctgt caaaatctcg gtcaaacttc     720
atcttagtgt cccttccctc cttgaatttg cagttctctg tatcacttga tccactgag     780
acgaaatgct catttggaga taagacatat gatattgtgc agagcatggg aggctatctc     840
ctctccatcg acataggtaa tgcgaactgg cgaggcccct gggatcctac ccctcagcat     900
ccgggtcgtg aaagaagatc aattatggag tttccggatc aaacatcttt cagatataac     960
caatttataa attatcactc atccccaaga cacaagagac atgatcaaga atttgagttc    1020
cctctcagtc taaaatccag ttatgattat gctcaattta gatatgagca gaatttcatc    1080
atccgacaga tcaataagaa ttttggatta ttacagaaga gcatttgtga tattcagttt    1140
tctaagtggc agaatctcag tccacccaat cttgctatga aaattgccca ttatgtcacc    1200
ggctctatcc actctatagg tggtgttcat catggatctt attcaattca aagaacggaa    1260
aaatccatta ctaaggtcaa tctggtgttt cccattgtta ttgttcatgg aatgtataag    1320
tgccaaaggg aaccatccaa ggaggtggtt tgggcagaac ccgtcacagg gatcttattc    1380
aagtctccta ttccgactca tttctcacta agttcctctt ggctacctgg ggtaaatggt    1440
tcttctattg tccctctgac aggtcaaatt cttctccctg aaatcacaat ggatcacttg    1500
gaggttgtac aacaggttga agcaaagatg gtcaaaagta tgtacacgaa tgtagagttg    1560
tttggatcaa cagaggaatt tcaaagatac caaactcagg gaattacctc tgatgaacaa    1620
tcaaatacag taaatccttg gattgggctt                                     1650
```

<210> SEQ ID NO 11
<211> LENGTH: 1854
<212> TYPE: DNA
<213> ORGANISM: Artificial Sequence
<220> FEATURE:
<223> OTHER INFORMATION: Nucleic acid sequence encoding a truncated Spodoptera frugiperda rhabdovirus G protein with an N-terminal melittin peptide and modified to include a 6x His tag

<400> SEQUENCE: 11

```
atgaaattct tagtcaacgt tgcccttgtt tttatggtcg tatacatttc ttacatctat      60
gccaatcctc tctcctatcc taatggcaat cctctctcct atcctaatgg cattttgact     120
aacaactcta ctcacaatca tcccctatcg gactttatata tttttatga gaacagttcc     180
cttacctata ctcaattccc tgtggcccca gactgctcta gtattctaga tactagagat     240
gagcagtatc ccaccactgt tactttgtgg aaggttgatc aagaatctca agctgagtgg     300
```

```
ggactcctttt tatggcaaga gagaattgac accacttgct cctggaactt ctggggcaat    360
tacaaaggat ccattgtatc taaatcctca gtacctctaa aggatatccc atcgggtagt    420
gcccggaatg gatattgggc tttgagcaat gatgaagttc aagagattga tcatgtccct    480
tacaacttga gatattattg ttactggtgc agaaatgaat atcctgggag cttttatatg    540
agatatgtaa agaaagttcg gatcataaga aatcctgatg ggtctataaa gactcctaga    600
ggatcctggg ttcatgagtt ggacaacttg tggggagatc agatgaggta tctagttatt    660
cgaagatttg ggggagaatc tagctgccct cttaagatat atgatgtgag agcagggggtt   720 ctgtcaaaat ctcggtcaaa cttcatctta gtgtcccttc cctccttgaa tttgcagttc    780
tctgtatcac ttgaatccac tgagacgaaa tgctcatttg gagataagac atatgatatt    840
gtgcagagca tgggaggcta tctcctctcc atcgacatag gtaatgcgaa ctggcgaggc    900
ccttgggatc ctaccccctca gcatccgggt cgtgaaagaa gatcaattat ggagtttccg    960
gatcaaacat ctttcagata taaccaattt ataaattatc actcatcccc aagacacaag  1020
agacatgatc aagaatttga gttccctctc agtctaaaat ccagttatga ttatgctcaa  1080
tttagatatg agcagaattt catcatccga cagatcaata agaattttgg attattacag  1140
aagagcattt gtgatattca gttttctaag tggcagaatc tcagtccacc caatcttgct  1200
atgaaaattg cccattatgt caccggctct atccactcta taggtggtgt tcatcatgga  1260
tcttattcaa ttcaaagaac ggaaaaatcc attactaagg tcaatctggt gtttcccatt  1320
gttattgttc atggaatgta taagtgccaa agggaaccat ccaaggaggt ggtttgggca  1380
gaacccgtca cagggatctt attcaagtct cctattccga ctcatttctc actaagttcc  1440
tcttggctac ctggggtaaa tggttcttct attgtccctc tgacaggtca aattcttctc  1500
cctgaaatca caatggatca cttggaggtt gtacaacagg ttgaagcaaa gatggtcaaa  1560
agtatgtaca cgaatgtaga gttgtttgga tcaacagagg aatttcaaag ataccaaact  1620
cagggaatta cctctgatga acaatcaaat acagtaaatc cttggattgg gcttttgata  1680
catggtggag tgtccatagc tactggaata ttagtagcac ttttgatccc ctcaatctta  1740
aaattgttca gacatataat tgagaaaggg gaggcatcgt tagaggagag gttgcatctg  1800
agggaaacct caagaaaaga atttgtcaag gttaggggga aaccatgggg tgtc         1854
```

<210> SEQ ID NO 12
<211> LENGTH: 1884
<212> TYPE: DNA
<213> ORGANISM: Artificial Sequence
<220> FEATURE:
<223> OTHER INFORMATION: Nucleic acid sequence encoding a Spodoptera
     frugiperda rhabdovirus G protein modified to include a 6x His tag

<400> SEQUENCE: 12

```
gaattcatgg ttttcttaag tttatcaacg atcatatttta tcctaagcct ccgggctgta     60
acctgctcca atcctctctc ctatcctaat ggcattttga ctaacaactc tactcacaat    120
catcccctat cggacttttta tatttttttat gagaacagtt cccttaccta tactcaattc    180
cctgtggccc cagactgctc tagtattcta gatactagag atgagcagta tcccaccact    240
gttactttgt ggaaggttga tcaagaatct caagctgagt ggggactcct tttatggcaa    300
gagagaattg acaccacttg ctcctggaac ttctggggca attacaaagg atccattgta    360
tctaaatcct cagtacctct aaaggatatc ccatcgggta gtgcccggaa tgatattgg    420 gctttgagca atgatgaagt tcaagagatt gatcatgtcc cttacaactt gagatattat    480
```

| | |
|---|---|
| tgttactggt gcagaaatga atatcctggg agctttata tgagatatgt aaagaaagtt | 540 |
| cggatcataa gaaatcctga tgggtctata aagactccta gaggatcctg ggttcatgag | 600 |
| ttggacaact tgtggggaga tcagatgagg tatctagtta ttcgaagatt tgggggagaa | 660 |
| tctagctgcc ctcttaagat atatgatgtg agagcagggg ttctgtcaaa atctcggtca | 720 |
| aacttcatct tagtgtccct tccctccttg aatttgcagt tctctgtatc acttgaatcc | 780 |
| actgagacga aatgctcatt tggagataag acatatgata ttgtgcagag catgggaggc | 840 |
| tatctcctct ccatcgacat aggtaatgcg aactggcgag gcccttggga tcctacccct | 900 |
| cagcatccgg gtcgtgaaag aagatcaatt atggagtttc cggatcaaac atctttcaga | 960 |
| tataaccaat ttataaatta tcactcatcc ccaagacaca gagacatga tcaagaattt | 1020 |
| gagttccctc tcagtctaaa atccagttat gattatgctc aatttagata tgagcagaat | 1080 |
| ttcatcatcc gacagatcaa taagaatttt ggattattac agaagagcat ttgtgatatt | 1140 |
| cagttttcta gtggcagaa tctcagtcca cccaatcttg ctatgaaaat tgcccattat | 1200 |
| gtcaccggct ctatccactc tataggtggt gttcatcatg gatcttattc aattcaaaga | 1260 |
| acggaaaaat ccattactaa ggtcaatctg gtgtttccca ttgttattgt tcatggaatg | 1320 |
| tataagtgcc aaagggaacc atccaaggag gtggtttggg cagaacccgt cacagggatc | 1380 |
| ttattcaagt ctcctattcc gactcatttc tcactaagtt cctcttggct acctggggta | 1440 |
| aatggttctt ctattgtccc tctgacaggt caaattcttc tccctgaaat cacaatggat | 1500 |
| cacttggagg ttgtacaaca ggttgaagca agatggtca aaagtatgta cacgaatgta | 1560 |
| gagttgtttg gatcaacaga ggaatttcaa agataccaaa ctcagggaat tacctctgat | 1620 |
| gaacaatcaa atacagtaaa tccttggatt gggcttttga tacatggtgg agtgtccata | 1680 |
| gctactggaa tattagtagc acttttgatc ccctcaatct taaaattgtt cagacatata | 1740 |
| attgagaaag gggaggcatc gttagaggag aggttgcatc tgagggaaac ctcaagaaaa | 1800 |
| gaatttgtca aggttagggg gaaaccatgg ggtgtcgaaa acctgtattt tcagggccac | 1860 |
| catcaccatc accattaact gcag | 1884 |

<210> SEQ ID NO 13
<211> LENGTH: 1704
<212> TYPE: DNA
<213> ORGANISM: Artificial Sequence
<220> FEATURE:
<223> OTHER INFORMATION: Nucleic acid sequence encoding a truncated Spodoptera frugiperda rhabdovirus G protein modified to include a 6x His tag

<400> SEQUENCE: 13

| | |
|---|---|
| gaattcatgg ttttcttaag tttatcaacg atcatatta tcctaagcct ccgggctgta | 60 |
| acctgctcca atcctctctc ctatcctaat ggcattttga ctaacaactc tactcacaat | 120 |
| catcccctat cggactttta tattttttat gagaacagtt cccttaccta tactcaattc | 180 |
| cctgtggccc cagactgctc tagtattcta gatactagag atgagcagta tcccaccact | 240 |
| gttactttgt ggaaggttga tcaagaatct caagctgagt ggggactcct tttatggcaa | 300 |
| gagagaattg acaccacttg ctcctggaac ttctggggca attacaaagg atccattgta | 360 |
| tctaaatcct cagtacctct aaaggatatc ccatcgggta gtgcccggaa tggatattgg | 420 |
| gctttgagca atgatgaagt tcaagagatt gatcatgtcc cttacaactt gagatattat | 480 |
| tgttactggt gcagaaatga atatcctggg agctttata tgagatatgt aaagaaagtt | 540 |
| cggatcataa gaaatcctga tgggtctata aagactccta gaggatcctg ggttcatgag | 600 |

```
ttggacaact tgtggggaga tcagatgagg tatctagtta ttcgaagatt tgggggagaa      660
tctagctgcc ctcttaagat atatgatgtg agagcagggg ttctgtcaaa atctcggtca      720
aacttcatct tagtgtccct tccctccttg aatttgcagt tctctgtatc acttgaatcc      780
actgagacga aatgctcatt tggagataag acatatgata ttgtgcagag catgggaggc      840
tatctcctct ccatcgacat aggtaatgcg aactggcgag gcccttggga tcctacccct      900
cagcatccgg gtcgtgaaag aagatcaatt atggagtttc cggatcaaac atctttcaga      960
tataaccaat ttataaatta tcactcatcc ccaagacaca agagacatga tcaagaattt     1020
gagttccctc tcagtctaaa atccagttat gattatgctc aatttagata tgagcagaat     1080
ttcatcatcc gacagatcaa taagaatttt ggattattac agaagagcat tgtgatatt      1140 cagttttcta gtggcagaa tctcagtcca cccaatcttg ctatgaaaat tgcccattat      1200
gtcaccggct ctatccactc tataggtggt gttcatcatg gatcttattc aattcaaaga     1260
acggaaaaat ccattactaa ggtcaatctg gtgtttccca ttgttattgt tcatggaatg     1320
tataagtgcc aaagggaacc atccaaggag gtggtttggg cagaacccgt cacagggatc     1380
ttattcaagt ctcctattcc gactcatttc tcactaagtt cctcttggct acctggggta     1440
aatggttctt ctattgtccc tctgacaggt caaattcttc tccctgaaat cacaatggat     1500
cacttggagg ttgtacaaca ggttgaagca aagatggtca aaagtatgta cacgaatgta     1560
gagttgtttg gatcaacaga ggaatttcaa agataccaaa ctcagggaat tacctctgat     1620
gaacaatcaa atacagtaaa tccttggatt gggcttgaaa acctgtattt tcagggccac     1680
catcaccatc accattaact gcag                                             1704
```

<210> SEQ ID NO 14
<211> LENGTH: 1908
<212> TYPE: DNA
<213> ORGANISM: Artificial Sequence
<220> FEATURE:
<223> OTHER INFORMATION: Nucleic acid sequence encoding a truncated
      Spodoptera frugiperda rhabdovirus G protein with an N-terminal
      melittin peptide and modified to include a 6x His tag

<400> SEQUENCE: 14

```
gaattcatga aattcttagt caacgttgcc cttgttttta tggtcgtata catttcttac       60
atctatgcca atcctctctc ctatcctaat ggcaatcctc tctcctatcc taatggcatt      120
ttgactaaca actctactca caatcatccc ctatcggact tttatatttt ttatgagaac      180
agttccctta cctatactca attccctgtg gccccagact gctctagtat tctagatact      240
agagatgagc agtatcccac cactgttact ttgtggaagg ttgatcaaga atctcaagct      300 gagtgggggac tcctttttatg gcaagagaga attgacacca cttgctcctg gaacttctgg      360
ggcaattaca aaggatccat tgtatctaaa tcctcagtac ctctaaagga tatcccatcg      420
ggtagtgccc ggaatggata ttgggctttg agcaatgatg aagttcaaga gattgatcat      480
gtcccttaca acttgagata ttattgttac tggtgcagaa atgaatatcc tgggagcttt      540
tatatgagat atgtaaagaa agttcggatc ataagaaatc ctgatgggtc tataaagact      600
cctagaggat cctgggttca tgagttggac aacttgtggg gagatcagat gaggtatcta      660
gttattcgaa gatttggggg agaatctagc tgccctctta agatatatga tgtgagagca      720
ggggttctgt caaatctccg gtcaaacttc atcttagtgt cccttccctc cttgaatttg      780
cagttctctg tatcacttga atccactgag acgaaatgct catttggaga taagacatat      840
gatattgtgc agagcatggg aggctatctc ctctccatcg acataggtaa tgcgaactgg      900
```

-continued

| | |
|---|---|
| cgaggcccctt gggatcctac ccctcagcat ccgggtcgtg aagaagatc aattatggag | 960 |
| tttccggatc aaacatcttt cagatataac caatttataa attatcactc atccccaaga | 1020 |
| cacaagagac atgatcaaga atttgagttc cctctcagtc taaaatccag ttatgattat | 1080 |
| gctcaattta gatatgagca gaatttcatc atccgacaga tcaataagaa ttttggatta | 1140 |
| ttacagaaga gcatttgtga tattcagttt tctaagtggc agaatctcag tccacccaat | 1200 |
| cttgctatga aaattgccca ttatgtcacc ggctctatcc actctatagg tggtgttcat | 1260 |
| catggatctt attcaattca agaacggaa aaatccatta ctaaggtcaa tctggtgttt | 1320 |
| cccattgtta ttgttcatgg aatgtataag tgccaaaggg aaccatccaa ggaggtggtt | 1380 |
| tgggcagaac ccgtcacagg gatcttattc aagtctccta ttccgactca tttctcacta | 1440 |
| agttcctctt ggctacctgg ggtaaatggt tcttctattg tccctctgac aggtcaaatt | 1500 |
| cttctccctg aaatcacaat ggatcacttg gaggttgtac aacaggttga agcaaagatg | 1560 |
| gtcaaaagta tgtacacgaa tgtagagttg tttggatcaa cagaggaatt tcaaagatac | 1620 |
| caaactcagg gaattacctc tgatgaacaa tcaaatacag taaatccttg gattgggctt | 1680 |
| ttgatacatg gtggagtgtc catagctact ggaatattag tagcactttt gatcccctca | 1740 |
| atcttaaaat tgttcagaca tataattgag aaaggggagg catcgttaga ggagaggttg | 1800 |
| catctgaggg aaacctcaag aaaagaattt gtcaaggtta gggggaaacc atggggtgtc | 1860 |
| gaaaacctgt attttcaggg ccaccatcac catcaccatt aactgcag | 1908 |

<210> SEQ ID NO 15
<211> LENGTH: 1563
<212> TYPE: DNA
<213> ORGANISM: Unknown
<220> FEATURE:
<223> OTHER INFORMATION: Nucleic acid sequence encoding a Spodoptera
      frugiperda rhabdovirus N protein

<400> SEQUENCE: 15

| | |
|---|---|
| atgacacagg gaaccatgaa gccagtatgg gaagaattgg ggacaggaga acagagttc | 60 |
| caagggaccg tggacattcc agggagatct ctcaagccag aaaaaacaga ttggagtgtt | 120 |
| gatacatgtc gggagatcag tttaaatctg aagttacctg gtgaaatatg gcaactggcc | 180 |
| catcaagaaa ccatcttcaa cagatttctt acattttacg ctactgggta tgttccaaat | 240 |
| acacacacag ccacagaaat tgtactctcc atggcatcac taatcttcaa ggacaaggcc | 300 |
| aaagcaccta ttgatttgat ttgggatgac tcatttcaag ctagtccctc tgaggagtgt | 360 |
| gggttctccg ttgttggaga aactccattg gttatcggac aacacccgga tgatgatgac | 420 |
| tacacattga gaagatgaa gaatcagcc gctatgaatg aggaagaaaa aatacaagca | 480 |
| gctctaaaaa ctttgggaat tcaagatact ccagtagacc tgaaggatgc atctggaatt | 540 |
| gtctttgaga caaaggagga cagagaacaa aggatcaaga atgagaaagc tctacatgta | 600 |
| gaggatgata tcaacgctct aactcagatt acaaaacaat tcttgtttga gtattccaca | 660 |
| ggctccctac agaaatttgt tgcaaaggct actactattt tcatagataa taatgctact | 720 |
| aacggcttca cccgttttgca tctccatgcc atcagagtca tgaacttcat tgctctaaca | 780 |
| atgcttagaa aggtaaccaa gtcaaatgcc cagatgatca atgcctttct gaaggagcaa | 840 |
| tacaagagaa atattgcctc cctaatcccc ggcgccctct cctctgatt tgctcctccc | 900 |
| agtaagagct gcattgataa actgacagct atttctaaga atgacccggc agtcagttca | 960 |
| ttctttgcaa aggttgtgat gctcaacatg gaggaggaac ggagaaaccc ttctctggtt | 1020 |

```
gcttgtcttg gggcttccct tctcacccac accacttgga atggaatggg gattttacat    1080 gttattttg aagtttgtct attccatcag attagctgga agaggttggt cacagagtcc     1140
ctgacctcac taacaaagat gtcatgqggt gaagtcagtc aattcctcat caagtatcaa    1200
gcaaagggaa atcctgaccc aacggttgcc tgggccagaa tcattgatga ttcttacttt    1260
atgagattaa ccatagtaaa tcatcccaca cttgctgcat tattagtgga atccctcata    1320
agatctcaga aagatgatgg aatcctgaat gccaactggg ccatccaaca cagggacacc    1380
atcaattatt atagggacgc tgccaagctt ctcactgata agctcacagg acagactgct    1440
acagtccaag cccttaccaa tgaagccgct gatctagtta aacaatgaa tgcaggaccc     1500 tctagatacc acccaaggcc tagtacccct atccccatgg tagatctaaa cccggaagac    1560
tta                                                                  1563
```

<210> SEQ ID NO 16
<211> LENGTH: 1617
<212> TYPE: DNA
<213> ORGANISM: Artificial Sequence
<220> FEATURE:
<223> OTHER INFORMATION: Nucleic acid sequence encoding a Spodoptera
      frugiperda rhabdovirus N protein modified to include a 6x His tag

<400> SEQUENCE: 16

```
ggatccatga cacagggaac catgaagcca gtatgggaag aattggggac aggagaaaca    60
gagttccaag ggaccgtgga cattccaggg agatctctca agccagaaaa aacagattgg    120
agtgttgata catgtcggga gatcagttta aatctgaagt tacctggtga atatatggcaa   180 ctggcccatc aagaaaccat cttcaacaga tttcttacat tttacgctac tgggtatgtt    240
ccaaatacac acacagccac agaaattgta ctctccatgg catcactaat cttcaaggac    300
aaggccaaag cacctattga tttgatttgg gatgactcat ttcaagctag tccctctgag    360
gagtgtgggt tctccgttgt tggagaaact ccattggtta tcggacaaca cccgatgat    420 gatgactaca cattgagaga agatgaagaa tcagccgcta tgaatgagga agaaaaaata    480
caagcagctc taaaaacttt gggaattcaa gatactccag tagacctgaa ggatgcatct    540
ggaattgtct ttgagacaaa ggaggacaga gaacaaagga tcaagaatga aaagctcta    600 catgtagagg atgatatcaa cgctctaact cagattacaa acaattctt gtttgagtat    660 tccacaggct ccctacagaa atttgttgca aaggctacta ctattttcat agataataat    720
gctactaacg gcttcacccg tttgcatctc catgccatca gagtcatgaa cttcattgct    780
ctaacaatgc ttagaaaggt aaccaagtca aatgcccaga tgatcaatgc ctttctgaag    840
gagcaataca agaaaatat tgcctcccta atccccggcg ccctctcctc tgattttgct    900
cctcccagta agagctgcat tgataaactg acagctattt ctaagaatga cccggcagtc    960
agttcattct ttgcaaaggt tgtgatgctc aacatggagg aggaacggag aaacccttct    1020
ctggttgctt gtcttggggc ttcccttctc acccacacca cttggaatgg aatgggggatt   1080 ttacatgtta tttttgaagt ttgtctattc catcagatta gctggaagag gttggtcaca    1140
gagtccctga cctcactaac aaagatgtca tggggtgaag tcagtcaatt cctcatcaag    1200
tatcaagcaa agggaaatcc tgacccaacg gttgcctggg ccagaatcat tgatgattct    1260
tactttatga gattaaccat agtaaatcat cccacacttg ctgcattatt agtggaatcc    1320
ctcataagat ctcagaaaga tgatggaatc ctgaatgcca ctgggccat ccaacacagg     1380 gacaccatca attattatag ggacgctgcc aagcttctca ctgataagct cacaggacag    1440
```

```
actgctacag tccaagccct taccaatgaa gccgctgatc tagttagaac aatgaatgca    1500
ggaccctcta gataccaccc aaggcctagt acccttatcc ccatggtaga tctaaacccg    1560
gaagacttag aaaacctgta ttttcagggc caccatcacc atcaccatta actgcag       1617
```

```
<210> SEQ ID NO 17
<211> LENGTH: 26
<212> TYPE: DNA
<213> ORGANISM: Artificial Sequence
<220> FEATURE:
<223> OTHER INFORMATION: forward primer to construct SEQ ID NO:12 or SEQ
      ID NO:13

<400> SEQUENCE: 17
aaaaaagaat tcatggtttt cttaag                                          26

<210> SEQ ID NO 18
<211> LENGTH: 66
<212> TYPE: DNA
<213> ORGANISM: Artificial Sequence
<220> FEATURE:
<223> OTHER INFORMATION: reverse primer to construct SEQ ID NO:12 or SEQ
      ID NO:14

<400> SEQUENCE: 18
tttttctgca gttaatggtg atggtgatgg tggccctgaa aatacaggtt ttcgacaccc    60
catggt                                                                66

<210> SEQ ID NO 19
<211> LENGTH: 68
<212> TYPE: DNA
<213> ORGANISM: Artificial Sequence
<220> FEATURE:
<223> OTHER INFORMATION: reverse primer to construct SEQ ID NO:13

<400> SEQUENCE: 19 tttttctgc agttaatggt gatggtgatg gtggccctga aaatacaggt ttcaagccc      60 aatccaag                                                              68

<210> SEQ ID NO 20
<211> LENGTH: 99
<212> TYPE: DNA
<213> ORGANISM: Artificial Sequence
<220> FEATURE:
<223> OTHER INFORMATION: forward primer to construct SEQ ID NO:14

<400> SEQUENCE: 20
tatatagaat tcatgaaatt cttagtcaac gttgcccttg tttttatggt cgtatacatt    60
tcttacatct atgccaatcc tctctcctat cctaatggc                            99

<210> SEQ ID NO 21
<211> LENGTH: 22
<212> TYPE: DNA
<213> ORGANISM: Artificial Sequence
<220> FEATURE:
<223> OTHER INFORMATION: forward primer to construct SEQ ID NO:16

<400> SEQUENCE: 21
aaaaaaggat ccatgacaca gg                                              22

<210> SEQ ID NO 22
<211> LENGTH: 66
<212> TYPE: DNA
<213> ORGANISM: Artificial Sequence
```

```
<220> FEATURE:
<223> OTHER INFORMATION: reverse primer to construct SEQ ID NO:16

<400> SEQUENCE: 22 ttttctgca gttaatggtg atggtgatgg tggccctgaa aatacaggtt ttctaagtct    60
tccggg                                                              66

<210> SEQ ID NO 23
<211> LENGTH: 233
<212> TYPE: PRT
<213> ORGANISM: Porcine circovirus

<400> SEQUENCE: 23
```

Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Glu Pro
225                 230

```
<210> SEQ ID NO 24
<211> LENGTH: 552
<212> TYPE: PRT
<213> ORGANISM: Avian influenza virus

<400> SEQUENCE: 24
```

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

```
Pro Leu Ile Leu Arg Asp Cys Ser Val Ala Gly Trp Leu Leu Gly Asn
 50                  55                  60

Pro Met Cys Asp Glu Phe Ile Asn Val Pro Glu Trp Ser Tyr Ile Val
 65                  70                  75                  80

Glu Lys Ala Asn Pro Ala Asn Asp Leu Cys Tyr Pro Gly Asn Phe Asn
                 85                  90                  95

Asp Tyr Glu Glu Leu Lys His Leu Leu Ser Arg Ile Asn His Phe Glu
            100                 105                 110

Lys Ile Gln Ile Ile Pro Lys Asn Ser Trp Ser Asp His Glu Ala Ser
        115                 120                 125

Ser Gly Val Ser Ser Ala Cys Pro Tyr Gln Gly Ser Ser Ser Phe Phe
    130                 135                 140

Arg Asn Val Val Trp Leu Ile Lys Lys Asn Asn Ala Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Val Gly Thr Ser Thr Leu Asn Gln Arg
        195                 200                 205

Leu Val Pro Lys Ile Ala Thr Arg Ser Lys Val Asn Gly Gln Asn Gly
    210                 215                 220

Arg Met Asp Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Val Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Lys Leu Val Leu Ala Thr Gly Leu Arg Asn Ser
305                 310                 315                 320

Pro Gln Arg Glu Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
        355                 360                 365

Glu Ser Thr Gln Lys Ala Ile Asp Gly Val Thr Asn Lys Val Asn Ser
    370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
    435                 440                 445

Tyr Asp Lys Val Arg Leu Gln Leu Arg Asp Asn Ala Lys Glu Leu Gly
450                 455                 460
```

-continued

```
Asn Gly Cys Phe Glu Phe Tyr His Lys Cys Asp Asn Glu Cys Met Glu
465                 470                 475                 480

Ser Val Arg Asn Gly Thr Tyr Asp Tyr Pro Gln Tyr Ser Glu Ala
                485                 490                 495

Arg Leu Lys Arg Glu Glu Ile Ser Gly Val Lys Leu Glu Ser Ile Gly
            500                 505                 510

Thr Tyr Gln Ile Leu Ser Ile Tyr Ser Thr Val Ala Ser Ser Leu Ala
            515                 520                 525

Leu Ala Ile Met Val Ala Gly Leu Ser Leu Trp Met Cys Ser Asn Gly
            530                 535                 540

Ser Leu Gln Cys Arg Ile Cys Ile
545                 550
```

<210> SEQ ID NO 25
<211> LENGTH: 18
<212> TYPE: DNA
<213> ORGANISM: Artificial Sequence
<220> FEATURE:
<223> OTHER INFORMATION: forward primer constructed to target a
      Spodoptera frugiperda rhabdovirus genomic region encoding a
      glycoprotein

<400> SEQUENCE: 25
ctattgtccc tctgacag                                                 18

<210> SEQ ID NO 26
<211> LENGTH: 19
<212> TYPE: DNA
<213> ORGANISM: Artificial Sequence
<220> FEATURE:
<223> OTHER INFORMATION: reverse primer constructed to target a
      Spodoptera frugiperda rhabdovirus genomic region encoding a
      glycoprotein

<400> SEQUENCE: 26
gaccatcttt gcttcaacc                                                19

<210> SEQ ID NO 27
<211> LENGTH: 23
<212> TYPE: DNA
<213> ORGANISM: Artificial Sequence
<220> FEATURE:
<223> OTHER INFORMATION: probe constructed to target a Spodoptera
      frugiperda rhabdovirus genomic region encoding a glycoprotein

<400> SEQUENCE: 27
caacctccaa gtgatccatt gtg                                           23

<210> SEQ ID NO 28
<211> LENGTH: 126
<212> TYPE: DNA
<213> ORGANISM: Artificial Sequence
<220> FEATURE:
<223> OTHER INFORMATION: G-block control constructed to target a
      Spodoptera frugiperda rhabdovirus genomic region encoding a
      glycoprotein

<400> SEQUENCE: 28
cctggggtaa atggttcttc tattgtccct ctgacaggtc aaattcttct ccctgaaatc    60
acaatggatc acttggaggt tgtacaacag gttgaagcaa agatggtcaa aagtatgtac   120
acgaat                                                             126

```
<210> SEQ ID NO 29
<211> LENGTH: 13534
<212> TYPE: DNA
<213> ORGANISM: Spodoptera frugiperda

<400> SEQUENCE: 29
tgaaaattat acgataaatg atcctaactc ttatagatga caacgactac ttcacggata      60
tcggcttctt agatcttatc atgacacagg gaaccatgaa gccagtatgg gaagaattgg     120
ggacaggaga aacagagttc aagggaccg tggacattcc agggagatct ctcaagccag      180
aaaaaacaga ttggagtgtt gatacatgtc gggagatcag tttaaatctg aagttacctg     240
gtgaaatatg gcaactggcc catcaagaaa ccatcttcaa cagatttctt acattttacg     300
ctactgggta tgttccaaat acacacacag ccacagaaat tgtactctcc atggcatcac     360
taatcttcaa ggacaaggcc aaagcaccta ttgatttgat ttgggatgac tcatttcaag     420
ctagtccctc tgaggagtgt gggttctccg ttgttggaga aactccattg gttatcggac     480
aacacccgga tgatgatgac tacacattga gagaagatga agaatcagcc gctatgaatg     540
aggaagaaaa aatacaagca gctctaaaaa ctttgggaat tcaagatact ccagtagacc     600
tgaaggatgc atctggaatt gtcttttgaga caaaggagga cagagaacaa aggatcaaga     660
atgagaaagc tctacatgta gaggatgata tcaacgctct aactcagatt acaaaacaat     720
tcttgtttga gtattccaca ggctccctac agaaatttgt tgcaaaggct actactattt     780
tcatagataa taatgctact aacggcttca cccgtttgca tctccatgcc atcagagtca     840
tgaacttcat tgctctaaca atgcttagaa aggtaaccaa gtcaaatgcc cagatgatca     900
atgcctttct gaaggagcaa tacaagagaa atattgcctc cctaatcccc ggcgccctct     960
cctctgattt tgctcctccc agtaagagct gcattgataa actgacagct atttctaaga    1020
atgacccggc agtcagttca ttcttttgcaa aggttgtgat gctcaacatg gaggaggaac    1080
ggagaaaccc ttctctggtt gcttgtcttg gggcttccct tctcacccac accacttgga    1140
atggaatggg gattttacat gttattttg aagtttgtct attccatcag attagctgga    1200
agaggttggt cacagagtcc ctgacctcac taacaaagat gtcatggggt gaagtcagtc    1260
aattcctcat caagtatcaa gcaaaggaa atcctgaccc aacggttgcc tgggccagaa    1320
tcattgatga ttcttacttt atgagattaa ccatagtaaa tcatcccaca cttgctgcat    1380
tattagtgga atccctcata agatctcaga aagatgatgg aatcctgaat gccaactggg    1440
ccatccaaca cagggacacc atcaattatt atagggacgc tgccaagctt ctcactgata    1500
agctcacagg acagactgct acagtccaag cccttaccaa tgaagccgct gatctagtta    1560
gaacaatgaa tgcaggaccc tctagatacc acccaaggcc tagtaccctt atccccatgg    1620
tagatctaaa cccggaagac ttataagact tacctattat cccaagacta atttccataa    1680
taatccccaa aaagacaatt actgttattt tctattaaaa aaccaatgaa aattatgcag    1740
agaatattga gacatatagt atccttcttc tcaaagtcct ggtgccaatc ctccgatccc    1800
gctctagtgt gcgactgtga gtatcctcct ctcaagagaa actatcaact gatttactct    1860
ataatggctt cccactctct tgacaccatt gatctatctg aaattggatt gacaagggag    1920
gttctgactg gggttggcga ttacatgact ggacaaagac cggttccagc cttcaatcct    1980
ccagaggtcg gtcactcccc ctctgatgaa gtggcaaaac gattgggaga actgaagaat    2040
tactggactc agttagagga tcctcttgat gagagaattc tcaataccct tgaaagcgatc   2100 agcatcctga gcggagacac cagaggagat ctgagtggaa aatataaaca tctagtccgc    2160
```

-continued

```
attagcggag atgacatgcc ccaattattg gacgaactta tagacatctg tcttctgggg    2220
cctaagactc taattgctac cttacgaatg gcgataaccg cctataccgc tgcattagcc    2280
agaaatgcca agtccaccat ctcagatatt actaccgcat cagcagattt gatggtcatc    2340
actcagatga tacagtccca gcaggaatct ttccaatcat cattagagca tctctctcat    2400
gcttggaata acgtcgccag tggtatgact gcttatacag cggaactgga taagagaacc    2460
ctcaagttga cacagcttac accgccagtc aagcctgacc atcaccgggc ccctctaca    2520 gcctccagtc ataccctga tgcttcagtg gggcttcata taaacataac cccggttgt     2580 gcatataagt cccaatttgg ggtattgact tgctgtccca atgggaacat tggttttctt    2640
gcaaataact ccgatggcac tgtgatagcc aaacttgtgg aagtaattag gaagccacgc    2700
cctctcacga cggccctcaa taagaacctg tctgagctga tcaattatgt caaggcaaat    2760
ccgaagatcc ttgctactta ctctacctct tctcctcagg ataagcttaa tatcctgaat    2820
gagatccact tctgcatccc agatcttacc aatcaatggg tcaaggcctg ataacattcc    2880
cttccctcac aaactctaaa gatatctcca tccttgatga cattttatt aattatattt     2940 aagtacgatt taagatctac ataccaaaac caaccatttt gatgattaac atgttattat    3000
aaaaaaccaa tgaaacttat acgttaattg agataagttt gatttcattg ttccttgtgt    3060
catcaccgaa cttttgagc tcgaacaatg agtgctcttg aacggattgc acggagccta     3120
tcattgaaga agttgaaccc taggagaact ccaaagactc agcctattcc tgaaaaggct    3180
actgtctatc atcctttcat gctctcttat gatctcaatt tagctattga gggtaaaatc    3240
cacatctccg ctatccaccat tatagtgaat gcccttccct tagcttgggc aatagaactc    3300
tttcactctg actcatcgtg gtcagggtgt cttgagtact tttggaaatc catcaaggat    3360
aacatattgg catccataaa ccctcgagtt gatccaaatg gaacttgtca tatgatgaca    3420
tcaatcataa ctttcctcgg attctcagat ggatcctgca tcaactcaga agcagagcca    3480
agacagctca caggatctag atcctgggag atcatgtctc taatcagaa tctcattgtg      3540 ataaccctag gattcaaaat aaccttgaaa accttcgcac agcaccagag atacagcttg    3600
cgtgaccatg gattccacaa attggagatg ctcaacgaga aagagaagaa atgttgaac     3660 tatatggggg tcaaacaatt aaaaccccag tatacacatg aaaagacatt cgagaaactc    3720
attctcaaga caaaggtcc aaaggggtct cgtgtcaggg caattcttca ctctcaaagt      3780
cgtgacatgt ggtctccaac cgctccttct cctccaccca catatgaaga tggatcctca    3840
gatgaatggg atcagcaaca actgcacagc ctcaaccacc tgcatacacc ttctgtcccc    3900
ctgagggccc ccaggacatc cccaccccaa caactctccc caaaaccgac atccacaacc    3960 caaccccctcc cacaactcac acaaccaaac aagcccaag aactctccaa gtagacactt     4020
gacagccccc accaattact tttagatcat aaaaaaccaa caggcagaat ataagaccta    4080
tcaattagag atattaaaaa atactaatta aacaattata catcaagcat ggctcatta     4140 tggttttctt aagtttatca acgatcatat ttatcctaag cctccgggct gtaacctgct    4200
ccaatcctct ctcctatcct aatggcattt tgactaacaa ctctactcac aatcatcccc    4260
tatcggactt ttatatttt tatgagaaca gttcccttac ctatactcaa ttccctgtgg     4320
ccccagactg ctctagtatt ctagatacta gagatgagca gtatcccacc actgttactt    4380
tgtggaaggt tgatcaagaa tctcaagctg agtggggact cctttatgg caagagaaa     4440 ttgacaccac ttgctcctgg aacttctggg gcaattacaa aggatccatt gtatctaaat    4500
cctcagtacc tctaaaggat atcccatcgg gtagtgcccg gaatggatat tgggctttga    4560
```

```
gcaatgatga agttcaagag attgatcatg tcccttacaa cttgagatat tattgttact    4620
ggtgcagaaa tgaatatcct gggagctttt atatgagata tgtaaagaaa gttcggatca    4680
taagaaatcc tgatgggtct ataaagactc ctagaggatc ctgggttcat gagttggaca    4740
acttgtgggg agatcagatg aggtatctag ttattcgaag atttggggga gaatctagct    4800
gccctcttaa gatatatgat gtgagagcag gggttctgtc aaaatctcgg tcaaacttca    4860
tcttagtgtc ccttccctcc ttgaatttgc agttctctgt atcacttgaa tccactgaga    4920
cgaaatgctc atttggagat aagacatatg atattgtgca gagcatggga ggctatctcc    4980
tctccatcga cataggtaat gcgaactggc gaggcccttg ggatcctacc cctcagcatc    5040
cgggtcgtga agaagatca attatggagt ttccggatca acatctttc agatataacc    5100
aatttataaa ttatcactca tccccaagac acaagagaca tgatcaagaa tttgagttcc    5160
ctctcagtct aaaatccagt tatgattatg ctcaatttag atatgagcag aatttcatca    5220
tccgacagat caataagaat tttggattat tacagaagag catttgtgat attcagtttt    5280
ctaagtggca gaatctcagt ccacccaatc ttgctatgaa aattgcccat tatgtcaccg    5340
gctctatcca ctctataggt ggtgttcatc atggatctta ttcaattcaa gaacggaaa    5400
aatccattac taaggtcaat ctggtgtttc ccattgttat tgttcatgga atgtataagt    5460
gccaaaggga accatccaag gaggtggttt gggcagaacc cgtcacaggg atcttattca    5520
agtctcctat tccgactcat ttctcactaa gttcctcttg gctacctggg gtaaatggtt    5580
cttctattgt ccctctgaca ggtcaaattc ttctccctga atcacaatg gatcacttgg     5640
aggttgtaca acaggttgaa gcaaagatgg tcaaaagtat gtacgaat gtagagttgt      5700
ttggatcaac agaggaattt caaagatacc aaactcaggg aattacctct gatgaacaat    5760
caaatacagt aaatccttgg attgggcttt tgatacatgg tggagtgtcc atagctactg    5820
gaatattagt agcacttttg atcccctcaa tcttaaaatt gttcagacat ataattgaga    5880
aagggggagc atcgttagag gagaggttgc atctgaggga aacctcaaga aaagaatttg    5940
tcaaggttag ggggaaacca tggggtgtct aagctaccac agcttccaca agagattgga    6000
ctccaggtgg ctctctccat caagcgatca tgactcacaa agtcccttca ggccctaaca    6060
gatcagtaca gccatcattc atttgggctc catctggccc caaccgactc tcttataaa    6120
aaaccaatga aacttataca gatcgtcctt gactgccaaa atggatctca ctttagacac    6180
tatgaggcat attgaaactc tgatcaattc acatctagag cttgaagacc ttaaatcttt    6240
gattacagac acttgtttga ttcactcaag ggatctatac aatcccttct tatacattat    6300
ctgttttgtc aaacctacca tcacagccag tgctgaaaac tttatgattg ggaaattaaa    6360
gaagatcata attccattct gggatgtggt tgatgtcaca agatgcaaaa gaatcatttg    6420
tactgaattt gctccagatg atgtgatatt aatgaaactg accctgtga tctcttatca     6480
ctctgcataa taaccagatc tctaaatata ttttaaaggg atagaaaaat ccttccctag    6540
ttattagttt ataccagtgt ctttatttat atttaatcta gatttctttt atagtgattc    6600
caattagaga agggatgaac tttagactta ttggttgtga tatagtaatg aaatagacag    6660
ttatttattc ttagttaatc tttaaacatt ttccttcttc tattttcgg ttaagtcacc     6720
aaactaccta tcaaaccaat acatgagaac agtgtattat tcctgctatt aaaaaagatc    6780
ataccttttc catctcagct cctcagtcaa atcttagttt cattaaatca ccatggatga    6840
attacaaagt gataatgtcc gtaaaaaacg tcccccttta tcaactcatt gtgacacccc    6900
tctcaccctc aacaatgcca gaaaagcctt attagtacct gcacccggtc aattcataca    6960
```

```
tcccaataac cccattcgac gagagtactt ggagatgcag agacaacttc agataacacc   7020
ccccaatcta tttgatctat caaaagttca gggttttttc ctaaatgtgt ttaatgtacc   7080
agtctctagc cttcctttat tagaatttag acaagcattg cacttggctt ctcaactata   7140
ccaagtagaa gttgaagggg ttctcaaaga gctaggggca tcagctacta aaattgatat   7200
atctcctctg atgaaaaata aggacttaat taatctttat ctgagaaaat gtttctggga   7260
ggaagcagtt gtcatgagtg gaaatgataa ctctagtcag ggatcctggt ggtcaagagc   7320
agataaaggg cttattctct ttagacgacc tgggcttgat atcataattg gggagaattt   7380
aatgtcaatc cagacatctc agaactccat attggtctcc cgagatcacc taaccatatt   7440
gtcagatctc gctgctgagc ggtttagtat aattctccaa tccttcttag ctgatcaaac   7500
ccataataca gatatgccca ccccttccga attaagttta tttcttaagg aaggagatga   7560
aatgctaact ttagcaggaa atcaaggata tgatctaatt tatactttag aatcttcctg   7620
tacttcccga ttagtaggga actatgaagg aggctcgtgg aaagattcta aattccggca   7680
tgaaattgtt aaagatttag agaaaaaagc ctcagatcta aatttacatc ctcaacttag   7740
agttagagaa caactgttag attcagtttt tgaacgaaat ctaaacgcct tcacccaact   7800
gtatgggcta tatcgcatat ggggtcaccc aactctggat ccattacttg ggacaatagc   7860
cctcaaagaa ttgggaacaa caccaagatt gtacctatca caccaagctc aggagattaa   7920
caacaagttt aaggaagagt tcataaaaag atatttaaat agacataagg agtggccgga   7980
attagatgta tcgaaattac caagacataa catcattcga gtccattatg agaagaaatt   8040
acaatttcct tctaaatcca gacaatatag gagatctcat ctctccttgg tagaattcaa   8100
agaggtattc cctgttgatc ctaaatttga tcttattgaa tttattgatg ataaatccat   8160
ctccttaggt ttcccagatc tccttaacga gatctataga aacaagagta tcgggaattc   8220
actagcaaga tccttattgc ttaatttcct ctcctctgac atttcagacc cccaagaatt   8280
tctgaagaat atagatacct cagggtttcc tcctgaagag atttgtgttg ggtacacga   8340 aaaagagaga gaaggaaagc taaaggcaag gctgtttgga ttactgacct tagtgaaacg   8400
atcatatgta gttatcacag aaaaactctt ggctgagcat ctatttccgt atttccctga   8460
aataaccatg acggatgacg agttagtttt ggagaaaaag aggcatgcat tcaatacaga   8520
acgaaaaaac aaatttatgg tgagtttgga tttttccaag tggaacacca atatgagagc   8580
cccagacaca cagccatttt accacactat agatacgatg tttggtttgg aaaattgttt   8640
taccaggaca catgaaatgt tctacaattc cttttttgtac cttatagacg gttcttatct   8700
cccaacaata gttgatgatg ggttcaaaac agatattgga tgttggcgac atcatcttgg   8760
gggaatcgaa ggtctcagac aaaaaggatg gactctgtgg acagttatgt tgatcaggct   8820
agttgcggaa aaatatattt tcaatatgtc tatcatggga cagggggaca atcaaatgct   8880
acttctaact ttcgattcta ataccccgga agaatatgcc ctctctcaag ttaatgattt   8940
ccttcagtca ttaaaggata aactgtcact aataggtcct cctctcaagt tggaggaaac   9000
ttggatttcc aaagactttt atttatatgg aaagtatcct atcaaaggag gtgtttctct   9060
caccacatcg tggaaaaaat catgcagaat gttccgatgt tgcaacgagg actatcccac   9120
catagagtcc agtttgtcct ccttagctgc aaacctgtac tctgcagtgg ctgctgataa   9180
ctttacacag actctgtttt tgtttactt atttgaatta gtaggtctat tccaatgcaa   9240
tattagaaga ccctatctcc aaaagaactc atttttatcaa tcgttagatc gaaatagaac   9300
cttcacagtt gcttctgcaa aagaccaaaa gaagaaactt catgtccctc ttgttctatc   9360
```

```
accccccaaat cagctacagc ctaccgaggt tttgttagga ctatgtttga ctccgaggac    9420 tttggggagga tatccagttg ttctgtaccc atcggtcttg ataaagggag ccccagacca    9480
attatcattt gatcttgcgt ccttaaaatt attttcaaag tcagcagatg caactgttaa    9540
taggataata acccgtgtat ccagtccatt cctctccgag tataagaatt attctctact    9600
ttttatgaac cctgaggcaa ttatcctgga gtctacaccc actcctgcag aggcaaggag    9660
aactacgatt ttagaatttc tttccaacag tgatcgtgtt aaccagcctt acataaaaga    9720
attcctaaac atcattcatg agaatgcaaa tcaatctatg gaagattttt taacctcaaa    9780
tcctgtactt catccacgtg taatctctct tctacttcag gcaactccac aatacagagc    9840
tcaacaagta attggaaggc tccaaaagac cccaacaatg gctagagtct acttaagaga    9900
gggagataga gatctttatg cactgttaga gatgtctgag ttgaatcatt ttaagtcagt    9960
attacgacaa gtctttgctg aggtaggcag gtattcattg cctcacttca actctttggt   10020
tgaacattcc accttttaa ggaacatggg ttggggtaaa ataattgaag gtgtagatag    10080
tgcccctcct catgaggtct tccatctaga ggtcatgaca tctattacag aatgccagga   10140
ttctccacat gcagacctgg ggttcatatc agttagactg aacacccta aagatgttgc    10200 aggaaattct cttgcaattg gaaccacaag accttataga ggatctatca ctaaaaataa   10260
agtcaactcc ttatcaacaa aaatccaagc cagaaccccct ctctgttac aaagagctct   10320 catggttgca ggactggaat cctgggcatt cactaaggat tcttcacttg ctcagttatc   10380
aagggggtta gtttggagtg ttacagactt accgtatgaa ctgttgactc cacaggtaga   10440
tcaggtttcg ggatcatatc aacatcgctt acgaaatgat agactagaca atgggggaat   10500
cagtcctgtt ttaccgaatc aaggtaccaa attcaattc aacactgtcc ctcttgtatg    10560
tttgaataaa ggaagtaaaa ataagaatgt catgttccaa gggcctttag tgatgtttgg   10620
aagtgtaatt ggcgagggac tgcttacaga aggtatcaat tatccagaga caaaactatt   10680
tcacatccat attaggaatc cctcttccat acaggatctt gatgaaaatc caatcaccta   10740
tccccctatt caacagccta tcagattgtt acgaaacccc caatctcctt tcttattttt   10800
cccatctgac aaaatcatgc cttatataaa aagaattcta aaatatccta tctgttcacg   10860
ggaagatctc aatgtgattt ctacagaatc tcgcttcaat actttattgg cctacgagtg   10920
cataaacttg cttgatccat ggtcatgggt ctctggatct gactcgagat tggtaactaa   10980
cggaataacc atcaactggg ctctctcttg taatattgta gagctatgtc ttgtgatcag   11040
cctcttactt ctagctattt tcttcacccc aactaaaatc attgatccgg aatggcatat   11100
caatagagtg ataaatgttg tcaaagcttc ccctctctcc tcatgggaga atttaacaaa   11160
tctctgtttc tgcaatgtct tcccaacccc tctattacat tttcttagag ctatgagccc   11220
acaaacctct gagggtttaa caaattcaaa tgttgcactt atactaaaga cttccattac   11280
attgatcctt cagaatatcc tttacgatag gaatttcata aaaggaaaag tacctcaccct   11340 gattgcaccc ccggctgtgt cttttaacct gcacccttac agggtcatag aaatcctagg   11400
gtggttatat aaggaacatg aagttcataa atcccatctt tcgtacctct ctaaggacat   11460
gctagatttg aaactaggga gtttggaagg tccctatgtt caccaattag acttttgggg   11520
gagccctacc cgaatatctg gaatcagctc tgagtctctg gattatcttt gtaaattgga   11580
agacgtaatt aaatctagat ccatagaggt actcacagtt gctacaatat ttgatccaaa   11640
tccactccca atgcctctag ttactggccc cattgttaag tcgggtgttg tgaacacaag   11700
gctgcaagta tctttttatt cagaggggga cgtactgcat ccggaattag gacatagaga   11760
```

| | |
|---|---|
| ttatagaact tcttttttcc gaccagctcc attgcccaca tcaggggctt ataagctatc | 11820 |
| aagtgttttg ccccttactag gaagctgtgc cttgacaaaa tgcctctgtt tagctgatgg | 11880 |
| aacaggtgga ttcaccagaa cactcgctct tagagatgat tcgaaaacaa ttgtattcaa | 11940 |
| tacattagta actgatcaag attatgtaac acaaatggac ccaattcaaa atatcccaga | 12000 |
| cattgcagat cttccaattt cttgtcagaa gaaagttgtg ggcctaaggg aggtcaatga | 12060 |
| ttatccaaca gatataacaa gcccggattt cggacatcaa attctggaca gatttggagg | 12120 |
| tgatttcatc ttggttacag gagatgcgga agaccctct ctgcaccata gtgggaatgt | 12180 |
| tttagctttg ttcaaagcct atatggatat tagcctaatt gtgaattccg ttcatggtat | 12240 |
| ctttaagatt catactcaca gaaggtctgt cctacatcag gctctggtta tattgttgac | 12300 |
| ttattatgac tctgtagttg tagtaagaag tcaattctct ctccgatcca acaatgaatt | 12360 |
| ttatcttgtt ggtgcaagaa acaagttagc tcctaaaatc cttccattaa atattattac | 12420 |
| tctggcagat ggtaatccga ccctaaatgt tggtctaagc agagatgctg aactgatgct | 12480 |
| gaataaaagt ctcaacaact taaatagaca acaaggtcaa ctgcaagagc tacaaaaatc | 12540 |
| tacctacata cagattacat ccaacttaat gcctcacctc cattaccaag atctaatctt | 12600 |
| tcacctagtt ggtcagtatc catggttgaa acaggaatac tttgatatcg gggaatccaa | 12660 |
| ggatggggat ctcagaccta tctactcatc ttgtatccat aagtttgtaa cctctataca | 12720 |
| caaggcaaat accaaatatg aggagaaaga tgtagcaaga tttgtggtaa agcaatttac | 12780 |
| tctaagagag ctgtcagata tattatcctc ctatctcttt ctgatactgt ctgttcttcc | 12840 |
| cctagccaga tggaattctt ggatacctca cttcttgaaa gaaggatgct tgttatggat | 12900 |
| acaatgtgag aatgggttgt ggttcttttc tccctatctg ggggttgtcc cacctgcgag | 12960 |
| atcaacctat catttagac tgtataggac acaagattta ttaaatcatg ttgcgatcca | 13020 |
| gaggatttgc agatctgttg gtttagctca catgttacac ttcagggaac ctgacgataa | 13080 |
| acatcttaaa gaagagtcca tctttactag accatcaagg aaattcacat tctatgatcc | 13140 |
| taaactcaag ggactaaaag acaagattaa atgtcagagt tggcaatggc tcagtcaatc | 13200 |
| tcctggttat caactggatc agtttgctcg aatttcccaa atcccaagaa ataaggagc | 13260 |
| atctatcaaa tcccccgacc aatgattgtc tctttgtcct ccatcaaact atatataaat | 13320 |
| caatcaatcg tcttaaagtt ctcttgattt ttgttgtata gattataaaa aaccaattat | 13380 |
| tttaattact tctctcattt acagttagtg tcccttaaga atatctggct tcatgtcatc | 13440 |
| aagggtggac cctctatttt atcttcattt tctctcagca acccactgca tcaatcattt | 13500 |
| cttcccctgc ttgccccccc tccccacga tcta | 13534 |

<210> SEQ ID NO 30
<211> LENGTH: 3208
<212> TYPE: DNA
<213> ORGANISM: Artificial Sequence
<220> FEATURE:
<223> OTHER INFORMATION: pVL1393 (Pharmingen)

<400> SEQUENCE: 30

| | |
|---|---|
| aagctttact cgtaaagcga gttgaaggat catatttagt tgcgtttatg agataagatt | 60 |
| gaaagcacgt gtaaaatgtt tcccgcgcgt tggcacaact atttacaatg cggccaagtt | 120 |
| ataaagatt ctaatctgat atgttttaaa acacctttgc ggcccgagtt gtttgcgtac | 180 |
| gtgactagcg aagaagatgt gtggaccgca gaacagatag taaaacaaaa ccctagtatt | 240 |
| ggagcaataa tcgatttaac caacacgtct aaatattatg atggtgtgca ttttttgcgg | 300 |

```
gcgggcctgt tatacaaaaa aattcaagta cctggccaga ctttgccgcc tgaaagcata    360
gttcaagaat ttattgacac ggtaaaagaa tttacagaaa agtgtcccgg catgttggtg    420
ggcgtgcact gcacacacgg tattaatcgc accggttaca tggtgtgcag atatttaatg    480
cacaccctgg gtattgcgcc gcaggaagcc atagatagat cgaaaaagc cagaggtcac     540 aaaattgaaa gacaaaatta cgttcaagat ttattaattt aattaatatt atttgcattc    600
tttaacaaat actttatcct attttcaaat tgttgcgctt cttccagcga accaaaacta    660
tgcttcgctt gctccgttta gcttgtagcc gatcagtggc gttgttccaa tcgacggtag    720
gattaggccg atattctcc accacaatgt tggcaacgtt gatgttacgt ttatgctttt     780
ggttttccac gtacgtcttt tggccggtaa tagccgtaaa cgtagtgccg tcgcgcgtca    840
cgcacaacac cggatgtttg cgcttgtccg cggggtattg aaccgcgcga tccgacaaat    900
ccaccacttt ggcaactaaa tcggtgacct gcgcgtcttt tttctgcatt atttcgtctt    960
tcttttgcat ggtttcctgg aagccggtgt acatgcggtt tagatcagtc atgacgcgcg   1020
tgacctgcaa atctttggcc tcgatctgct tgtccttgat ggcaacgatg cgttcaataa   1080
actcttgttt tttaacaagt tcctcggttt tttgcgccac caccgcttgc agcgcgtttg   1140
tgtgctcggt gaatgtcgca atcagcttag tcaccaactg tttgctctcc tcctcccgtt   1200
gtttgatcgc gggatcgtac ttgccggtgc agagcacttg aggaattact tcttctaaaa   1260
gccattcttg taattctatg gcgtaaggca atttggactt cataatcagc tgaatcacgc   1320
cggatttagt aatgagcact gtatgcggct gcaaatacag cgggtcgccc cttttcacga   1380
cgctgttaga ggtagggccc ccattttgga tggtctgctc aaataacgat ttgtatttat   1440
tgtctacatg aacacgtata gctttatcac aaactgtata ttttaaactg ttagcgacgt   1500
ccttggccac gaaccggacc tgttggtcgc gctctagcac gtaccgcagg ttgaacgtat   1560
cttctccaaa tttaaattct ccaatttttaa cgcgagccat tttgatacac gtgtgtcgat   1620
tttgcaacaa ctattgtttt ttaacgcaaa ctaaacttat tgtggtaagc aataattaaa   1680 tatggggaa catgcgccgc tacaacactc gtcgttatga acgcagacgg cgccggtctc    1740
ggcgcaagcg gctaaaacgt gttgcgcgtt caacgcggca acatcgcaa aagccaatag    1800 tacagttttg atttgcatat taacggcgat ttttttaaatt atcttattta ataaatagtt   1860
atgacgccta caactccccg cccgcgttga ctcgctgcac ctcgagcagt tcgttgacgc   1920
cttcctccgt gtggccgaac acgtcgagcg ggtggtcgat gaccagcggc gtgccgcacg   1980
cgacgcacaa gtatctgtac accgaatgat cgtcgggcga aggcacgtcg gcctccaagt   2040
ggcaatattg gcaaattcga aaatatatac agttgggttg tttgcgcata tctatcgtgg   2100
cgttgggcat gtacgtccga acgttgattt gcatgcaagc cgaaattaaa tcattgcgat   2160
tagtgcgatt aaaacgttgt acatcctcgc ttttaatcat gccgtcgatt aaatcgcgca   2220
atcgagtcaa gtgatcaaag tgtggaataa tgttttcttt gtattcccga gtcaagcgca   2280
gcgcgtattt taacaaacta gccatcttgt aagttagttt catttaatgc aactttatcc   2340
aataatatat tatgtatcgc acgtcaagaa ttaacaatgc gcccgttgtc gcatctcaac   2400
acgactatga tagagatcaa ataaagcgcg aattaaatag cttgcgacgc aacgtgcacg   2460
atctgtgcac gcgttccggc acgagctttg attgtaataa gttttacga agcgatgaca    2520 tgacccccgt agtgacaacg atcacgccca aagaactgc cgactacaaa attaccgagt    2580
atgtcggtga cgttaaaact attaagccat ccaatcgacc gttagtcgaa tcaggaccgc    2640
tggtgcgaga agccgcgaag tatggcgaat gcatcgtata acgtgtggag tccgctcatt   2700
```

-continued

```
agagcgtcat gtttagacaa gaaagctaca tatttaattg atcccgatga ttttattgat    2760
aaattgaccc taactccata cacggtattc tacaatggcg gggttttggt caaaatttcc    2820
ggactgcgat tgtacatgct gttaacggct ccgcccacta ttaatgaaat taaaaattcc    2880
aattttaaaa aacgcagcaa gagaaacatt tgtatgaaag aatgcgtaga aggaaagaaa    2940
aatgtcgtcg acatgctgaa caacaagatt aatatgcctc cgtgtataaa aaaaatattg    3000
aacgatttga aagaaaacaa tgtaccgcgc ggcggtatgt acaggaagag gtttatacta    3060
aactgttaca ttgcaaacgt ggtttcgtgt gccaagtgtg aaaaccgatg tttaatcaag    3120
gctctgacgc atttctacaa ccacgactcc aagtgtgtgg gtgaagtcat gcatctttta    3180
atcaaatccc aagatgtgta taaaccac                                      3208
```

MARKER SYSTEM, IN PARTICULAR FOR BACULOVIRUS-EXPRESSED SUBUNIT ANTIGENS

CROSS-REFERENCE TO OTHER APPLICATIONS

This application is a continuation of U.S. patent application Ser. No. 15/061,690, filed Mar. 4, 2016, now U.S. Pat. No. 10,168,330, which claims the benefit of U.S. Patent Application No. 62/128,744, filed Mar. 5, 2015, the entire contents of which are hereby incorporated by reference herein.

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

Field of the Invention

The present invention belongs to the field of compliance markers and marker vaccines which allow for the differentiation between infected and vaccinated individuals. In particular, it relates to a compliance marker for vaccines including a subunit antigen, and a DIVA (Differentiating Infected from Vaccinated Animals) system which makes it possible to differentiate between animals infected with a pathogen and animals treated with a subunit antigen derived from said pathogen, wherein said subunit antigen has been expressed in cultured insect cells, preferably by means of a genetically engineered baculovirus.

Description of the Related Art

Baculoviruses are large rod-shaped double stranded DNA viruses that infect invertebrates, in particular insects, but do not replicate in mammalian or other vertebrate cells. Starting in the 1940's they were first used as biopesticides in the crop fields. Additionally, after the publication of a first paper describing the overexpression of human beta interferon in insect cells (Smith et al. Mol Cell Biol. 3: 2156-2165 (1983)), genetically engineered baculoviruses have been widely used for producing complex recombinant proteins in insect cell cultures, including the production of antigens for several approved human and veterinary subunit vaccines (van Oers et al. J Gen Virol. 96: 6-23 (2015)).

Vaccination is an essential tool to manage herd health, in particular in high density confinement settings where many food animals are raised. When disease outbreaks occur in animals that were supposedly vaccinated, questions arise as to whether the vaccine failed to protect the animals or whether the vaccine was delivered properly, wherein the latter possibility regarding proper delivery of the vaccine is referred to as vaccine compliance.

The use of compliance markers for determining if an animal has been properly vaccinated is thus highly desired by producers. WO 2009/058835 A1 describes e.g. the use of purified xylanase which was added as a compliance marker to a swine influenza vaccine. Regarding vaccines comprising baculovirus-expressed subunit antigens, it is possible to use baculovirus antigens as a compliance marker, wherein, however, currently used systems have limitations in animals testing positive and that a high amount of antigen is needed (Gerber et al. Res Vet Sci. 95:775-81 (2013); Lehnert. Top Agrar 5: S11-S14 (2011)).

Vaccines used in programs for controlling viral outbreaks and infections must have an effective system to monitor for continued presence of viral infection within the population. However, vaccination complicates large scale surveillance for the spread of the infection by e.g. serological means, as both vaccinated and exposed individuals produce antibody specific for the virus. The antigenic similarity between the infecting virulent field strain of the virus and the viral vaccine frequently hampers the discrimination between infected and vaccinated subjects as vaccination results in the occurrence and persistence of antibodies that are indistinguishable between infected and vaccinated individuals.

There is increasing worldwide interest in DIVA (differentiating infected and vaccinated animals) vaccination strategies. For example, the joint WHO/FAO/OIE meetings on avian influenza strain H5N1 HPAI have recommended that all vaccination is practiced using a DIVA, so spread of infection can be monitored. However, current DIVA methods are difficult to scale-up and often have problems with the differentiation of vaccination from infection with other circulating viral strains.

Current methods of monitoring include physical tagging of vaccinated animals, the use of sentinel animals, and virological testing. However, these current methods have a number of limitations due to logistical and economic reasons.

The physical tagging of vaccinated animals involves the time consuming individual identification of vaccinated individuals by physical means such as ear tags, leg bands or wing tags. Also, the use of unvaccinated sentinel animals is logistically and economically difficult and there is also a risk that if sentinels become infected with the virus, e.g. poultry infected with H5N1 virus, there is increased risk of spread to humans. Virological testing of individuals via screening and detection of live virus or RT-PCR surveillance testing is a very expensive and infrastructure heavy process, which is not applicable for subunit vaccines, and only provides information relating to the current status of an individual, and does not allow analysis of the infection and/or vaccination history of that individual.

In view of said limitations, the use of marker vaccines allowing a serological discrimination of vaccinated and infected animals is highly preferable, wherein such marker vaccines can be prepared either as negative or positive marker vaccine.

A negative marker vaccine is prepared by using an antigenic portion of the pathogen or by the removal of an antigen from the pathogen, which provokes specific antibodies in infected animals. Negative marker vaccines are usually either subunit vaccines or attenuated live vaccines containing a genetically engineered strain lacking an immunogenic antigen. An example for a negative marker vaccine is e.g. the use of baculovirus-expressed classical swine fever virus (CSFV) E2 protein as a subunit antigen for vaccinating against classical swine fever, wherein a detection of antibodies specific for other antigens of CSFV, e.g. $E^{RNS}$ protein or NS3 protein, in sera of vaccinated pigs shows a CSFV infection.

A positive marker vaccine contains an additional antigen which induces specific antibodies in vaccinated individuals but not in infected ones. An example for a positive marker vaccine approach is described in WO 2007/053899 A1, where inactivated H6N2 Avian Influenza (AI) virus and tetanus toxin, both of which separately produced, were combined in one injection for vaccinating birds, and subsequently antibodies specific for tetanus toxin were detected in sera obtained from said birds as markers showing that the birds were vaccinated.

However, the separate production of both the vaccine antigen and the marker antigen is relatively expensive and, furthermore, a mixing step is required for combining both components in one vaccinating agent, wherein this additionally may also affect the stability of the vaccine components/antigens.

Thus, a simple marker system is needed for inexpensively producing positive marker vaccines, in particular subunit vaccines comprising baculovirus-expressed antigens.

Furthermore, effective compliance markers are needed which also enable the sensitive identification of vaccinations with a low amount of baculovirus-expressed subunit antigen.

BRIEF DESCRIPTION OF THE DRAWINGS

FIG. 1: Amplified products were run on a gel to verify size.

FIG. 2: Cut insert and vector were run on a gel to check for linearization of vector.

FIG. 3: Positive clones from wells 2, 5, 7, 10, 11, and 12 were sequenced and the contigs were aligned with the construct reference sequence to check for mutations; all clones were a perfect match.

FIG. 4: Western blots to evaluate expression of G gene construct.

FIG. 5: The supernatant, soluble and insoluble cell fractions were probed for the protein; at this time protein is present in the insoluble portion.

FIG. 6: Results of size exclusion chromatography run using isocratic conditions on an AKTA. Elution of proteins from the column was monitored with UV absorption at 280 nm.

FIG. 7: Real Time PCR results: Column 1 indicates the well numbers. Column 2 shows the fluorophore 6-carboxyfluorescein (FAM) linked to the specific probe used. Column 3 indicates the fractions of SfRV antigen derived from size exclusion chromatography (fractions A11, A12, B1, B5, B12 and C6) or the standards with known quantities of SfRV specific nucleic acid used to generate the standard curve (wells 7-14). Well 15 is the negative control (no template) and well 16 is the positive control containing concentrated SfRV antigen prior to fractionation by seize (SEC).

FIG. 8: ELISA; ELISA plates were coated with four different antigens including semi-purified SfRV (panel A), size exclusion fractions A11 (Panel B), A12 (Panel C) and B1 (Panel D). Plates were probed with sera from negative control animals (inverted triangles) or Day 28 sera from animals administered with experimental vaccine containing SfRV (circles).

DESCRIPTION OF THE INVENTION

The solution to the above technical problems is achieved by the description and the embodiments characterized in the claims.

Thus, the invention in its different aspects is implemented according to the claims.

The invention is based on the surprising finding that the use of Sf+ cells, which are infected with a rhabdovirus, for producing baculovirus-expressed antigens enables the inexpensive and efficient production of positive marker vaccines, and an easy and production inherent compliance marking which allows a sensitive method showing the proper delivery of the subunit vaccine.

In a first aspect, the invention thus provides a method of determining whether an individual has received an immunogenic composition, in particular a vaccine, comprising a recombinant protein produced by an expression system, preferably by a baculovirus expression system, in cultured insect cells, wherein said method, comprises the steps of: obtaining a biological sample from an individual; and determining in said biological sample the presence or absence of one or more markers showing that the individual has received one or more antigens from a virus which is an RNA virus capable of infecting insect cells, wherein the presence of said one or more markers in said biological sample indicates that said individual has received said immunogenic composition or wherein the absence of said one or more markers in said biological sample indicates that said individual has not received said immunogenic composition.

The term "recombinant protein", as used herein, in particular refers to a protein molecule which is expressed from a recombinant DNA molecule, such as a polypeptide which is produced by recombinant DNA techniques. An example of such techniques includes the case when DNA encoding the expressed protein is inserted into a suitable expression vector, preferably a baculovirus expression vector, which is in turn used to transfect, or in case of a baculovirus expression vector to infect, a host cell to produce the protein or polypeptide encoded by the DNA. The term "recombinant protein", as used herein, thus in particular refers to a protein molecule which is expressed from a recombinant DNA molecule.

According to a particular example, the recombinant protein is produced by a method with the following steps: the gene encoding the protein is cloned into a baculovirus transfer vector; the transfer vector is used to prepare recombinant baculovirus containing said gene by homologous recombination in insect cells; and the protein is then expressed in insect cells during infection with the recombinant baculovirus.

According to an alternative example, the recombinant protein is expressed in insect cells from a recombinant expression plasmid. In the case of this alternative example baculovirus is not needed.

It is further understood that the term "recombinant protein consisting of a sequence" in particular also concerns any cotranslational and/or posttranslational modification or modifications of the sequence affected by the cell in which the polypeptide is expressed. Thus, the term "recombinant protein consisting of a sequence", as described herein, is also directed to the sequence having one or more modifications effected by the cell in which the polypeptide is expressed, in particular modifications of amino acid residues effected in the protein biosynthesis and/or protein processing, preferably selected from the group consisting of glycosylations, phosphorylations, and acetylations.

Preferably, the recombinant protein of the present invention is produced or obtainable by a baculovirus expression system, in particular in cultured insect cells.

The term "expression system" as used herein particularly includes vehicles or vectors for the expression of a gene in a host cell as well as vehicles or vectors which bring about stable integration of a gene into the host chromosome.

As used herein "baculovirus expression system" in particular means a system for producing a desired protein in an insect cell using a recombinant baculovirus vector designed to express said protein. A baculovirus expression system generally comprises all elements necessary to achieve recombinant protein expression in insect cells, and typically involves the engineering of a baculovirus vector to express a desired protein, the introduction of the engineered baculovirus vector into insect cells, the culturing of the insect cells containing the engineered baculovirus vector in a suitable growth medium such that the desired protein is expressed, and the recovery of the protein. Typically, engineering a baculovirus vector involves the construction and isolation of recombinant baculoviruses in which the coding sequence for a chosen gene is inserted behind the promoter for a nonessential viral gene, wherein most of the presently used baculovirus expression systems are based on the sequence of *Autographa californica* nuclear polyhedrosis virus (AcMNPV) ((Virology 202 (2), 586-605 (1994), NCBI Accession No.: NC_001623). Baculovirus expression systems are well known in the art and have been described, for example, in "Baculovirus Expression Vectors: A Laboratory Manual" by David R. O'Reilly, Lois Miller, Verne Luckow, pub. by Oxford Univ. Press (1994), "The Baculovirus Expression System: A Laboratory Guide" by Linda A. King, R. D. Possee, published by Chapman & Hall (1992). An exemplary non-limiting example of a baculovirus system for producing a recombinant protein is e.g. described in WO 2006/072065 A2.

According to said first aspect, the present invention hence provides a method of determining whether an individual has received an immunogenic composition comprising a recombinant protein produced by an expression system in cultured insect cells, said method also being termed "the method of the present invention" hereinafter, wherein said method in particular comprises determining in a biological sample obtained from said individual the presence or absence of one or more markers showing that the individual has received one or more antigens from a virus which is an RNA virus capable of infecting insect cells, and wherein the presence of said one or more markers in said biological sample indicates that said individual has received said immunogenic composition.

"Insect cell" as used herein means a cell or cell culture derived from an insect species. Of particular interest with respect to the present invention are insect cells derived from the species *Spodoptera frugiperda* and *Trichoplusia ni*.

As used herein, a "virus capable of infecting insect cells" is particularly understood as a virus harboring structures on the viral surface that are capable of interacting with insect cells to such an extent that the virus, or at least the viral genome, becomes incorporated into the insect cell.

Said infection of an insect cell more particular includes attachment of the virus to a host cell, entry of the virus into the cell, uncoating of the virion in the cytoplasm, replication and transcription of the viral genome, expression of viral proteins and assembly and release of new infectious viral particles.

Preferably, the immunogenic composition of the present invention is a marker vaccine, in particular a positive marker vaccine.

The term "marker vaccine" as described herein, in particular specifies a vaccine leading to an immunization in the immunized organism, which differs from the immunization of the organism caused by the real pathogen.

A "positive marker vaccine" particularly relates to a marker vaccine containing an additional antigen which induces the production of specific antibodies present in vaccinated individuals but not in infected ones.

The term "marker" as used within the context of the present invention is preferably equivalent to the term "biomarker", and in particular refers to a measurable substance or compound which indicates that an individual has been exposed to an immunogenic composition, preferably to a positive marker vaccine or, more particular, to the additional antigen of a positive marker vaccine which induces the production of specific antibodies found in vaccinated subjects but not in infected ones.

As used herein, the term "immunogenic composition" in particular refers to a composition that will elicit an immune response in an individual that has been exposed to the composition. An immune response may include induction of antibodies and/or induction of a T-cell response. Depending on the intended function of the composition, one or more antigens may be included. Preferably, the immunogenic composition as described herein is a vaccine.

The term "vaccine" as used herein, is defined in accordance with the pertinent art and relates to a composition that induces or enhances immunity of an individual to a particular disease. To this end, the vaccine comprises a compound that is similar to the pathogen or a compound of said pathogen causing said disease. Upon contact with this compound, the immune system of the individual is triggered to recognize the compound as foreign and to destroy it. The immune system subsequently remembers the contact with this compound, so that at a later contact with the disease-causing pathogen an easy and efficient recognition and destruction of the pathogen is ensured. In accordance with the present invention, the vaccine may be in any formulation for vaccines known in the art, such as for example vaccines for intramuscular injection, mucosal vaccines or vaccines for subcutaneous or intradermal injection as well as vaccines for inhalation, such as e.g. as aerosols. Such vaccine formulations are well known in the art and have been described, e.g. in Neutra M R et al. 2006 Mucosal vaccines: the promise and the challenge 6(2): 148-58 or F. P. Nijkamp, Michael J Parnham 2011; Principles of Immunopharmacology ISBN-13: 978-3034601351.

The method of the present invention is thus in particular a method of determining whether an individual has received an immunogenic composition comprising a recombinant protein produced by a baculovirus expression system in cultured insect cells, wherein said method comprises determining in a biological sample obtained from said individual the presence or absence of one or more markers showing that the individual has received one or more antigens from a virus which is an RNA virus capable of infecting insect cells, and wherein the presence of said one or more markers in said biological sample indicates that said individual has received said immunogenic composition.

Preferably, the biological sample is obtained from said individual at least 14 days and most preferably 14 to 35 days after the day the individual has been vaccinated or, respectively, has been supposedly vaccinated.

Preferably, the insect cell, as mentioned herein, is a *Spodoptera Frugiperda* (Sf) cell or a cell from a cell line derived from *Spodoptera Frugiperda*, and is more preferably selected from the group consisting of Sf9 cell and Sf+ cell. Respectively, the insect cells, as mentioned herein, are preferably *Spodoptera Frugiperda* (Sf) cells or cells from a cell line derived from *Spodoptera Frugiperda*, and are more preferably selected from the group consisting of Sf9 cells and Sf+ cells.

The one or more markers showing that the individual has received one or more antigens from an RNA virus capable of infecting insect cells, as mentioned herein, which are also termed "the one or more markers of the present invention" hereinafter, are preferably one or more markers selected from the group consisting of: antibodies specific for one or more antigens from a virus which is an RNA virus capable of infecting insect cells; one or more antigens from a virus which is an RNA virus capable of infecting insect cells, and; one or more nucleic acid molecules specific for an RNA virus capable of infecting insect cells.

Most preferably, the one or more markers of the present invention are antibodies specific for an antigen from a virus which is an RNA virus capable of infecting insect cells.

Preferably, the antibodies as described herein are polyclonal antibodies.

As used herein, the term "antibodies specific for" a defined antigen in particular refers to antibodies, preferably polyclonal antibodies, that bind an antigen with an affinity or $K_a$ (i.e., an equilibrium association constant of a particular binding interaction with units of 1/M) of, for example, greater than or equal to about $10^5$ $M^{-1}$, $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$ or $10^{13}$ $M^{-1}$. Alternatively, binding affinity may be defined as an equilibrium dissociation constant ($K_d$) of a particular binding interaction with units of M (e.g., $10^{-5}$ M to $10^{-13}$ M). Binding affinities of antibodies can be readily determined using techniques well known to those of skill in the art (see, e.g., Scatchard et al. (1949) Ann. N.Y. Acad. Sci. 51:660; U.S. Pat. Nos. 5,283,173; 5,468,614; BIACORE® analysis; or the equivalent).

The one or more antigens from an RNA virus capable of infecting insect cells, as mentioned herein, which are also termed "the one or more antigens according to the present invention" hereinafter, is preferably a protein comprising or consisting of a sequence having at least 70%, preferably at least 80%, more preferably at least 90%, still more preferably at least 95% or in particular 100% sequence identity with the sequence of SEQ ID NO:1 and/or a protein comprising or consisting of a sequence having at least 70%, preferably at least 80%, more preferably at least 90%, still more preferably at least 95% or in particular 100% sequence identity with the sequence of SEQ ID NO:7.

Regarding the term "at least 90%", as mentioned in the context of the present invention, it is understood that said term preferably relates to "at least 91%", more preferably to "at least 92%", still more preferably to "at least 93%" or in particular to "at least 94%".

Regarding the term "at least 95%" as mentioned in the context of the present invention, it is understood that said term preferably relates to "at least 96%", more preferably to "at least 97%", still more preferably to "at least 98%" or in particular to "at least 99%".

The term "having 100% sequence identity", as used herein, is understood to be equivalent to the term "being identical".

As used herein, the term "antigen" in particular refers to any molecule, moiety or entity capable of eliciting an immune response. This includes cellular and/or humoral immune responses.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2. For purposes of the present invention, nucleotide sequences are aligned using Clustal W method in MegAlign software version 11.1.0 (59), 419 by DNASTAR Inc. using the default multiple alignment parameters set in the program (Gap penalty=15.0, gap length penalty=6.66, delay divergent sequence (%)=30%, DNA transition weight=0.50 and DNA weight matrix=IUB) and, respectively, protein/amino acid sequences are aligned using Clustal W method in MegAlign software software version 11.1.0 (59), 419 by DNASTAR Inc. using the default multiple alignment parameters set in the program (Gonnet series protein weight matrix with Gap penalty=10.0, gap length penalty=0.2, and delay divergent sequence (%)=30%).

As used herein, it is in particular understood that the term "sequence identity with the sequence of SEQ ID NO:X" is equivalent to the term "sequence identity with the sequence of SEQ ID NO:X over the length of SEQ ID NO: X" or to the term "sequence identity with the sequence of SEQ ID NO:X over the whole length of SEQ ID NO: X", respectively. In this context, "X" is any integer selected from 1 to 24 so that "SEQ ID NO: X" represents any of the SEQ ID NOs mentioned herein.

The one or more nucleic acid molecules specific for an RNA virus capable of infecting insect cells, as mentioned herein, which are also termed "the one or more nucleic acid molecules according to the present invention" hereinafter, is preferably a nucleic acid molecule which encodes: a protein comprising or consisting of a sequence having at least 70%, preferably at least 80%, more preferably at least 90%, still more preferably at least 95% or in particular 100% sequence identity with the sequence of SEQ ID NO: 1 and/or; a protein comprising or consisting of a sequence having at least 70%, preferably at least 80%, more preferably at least 90%, still more preferably at least 95% or in particular 100% sequence identity with the sequence of SEQ ID NO:7; and/or an RNA having a sequence that is inverse complementary to a nucleic acid sequence having at least 70%, preferably at least 80%, more preferably at least 90%, still more preferably at least 95% or in particular 100% sequence identity with the sequence of SEQ ID NO:9; and/or a sequence that is inverse complementary to a nucleic acid sequence having at least at least 70%, preferably at least 80%, more preferably at least 90%, still more preferably at least 95% or in particular 100% sequence identity with the sequence of SEQ ID NO:15.

Preferably, the method of the present invention comprises the steps of: contacting the biological sample with a capture reagent immobilized to a solid support, wherein the immobilized capture reagent is capable of binding the one or more markers of the present invention; and determining the presence or absence of said one or more markers bound to the capture reagent, wherein the presence of said one or more markers bound to the capture reagent is indicative for the presence of said one or more markers in said biological sample.

The term "capture reagent", as used herein, in particular refers to a molecule or a multi-molecular complex that can bind to a marker. The capture reagent is preferably capable of binding the marker in a substantially specific manner, preferably with an affinity or $K_a>10^5$ $M^{-1}$ or preferably $>10^6 M^{-1}$. The capture reagent may optionally be a naturally occurring, recombinant, or synthetic biomolecule. Proteins and nucleic acid ligands (aptamers) are highly suitable as capture agents. A whole virus or a virus fragment or a synthetic peptide may also serve as preferred capture reagents, since they are capable of binding antibodies.

As used herein the term "immobilized" particularly means that the capture reagent can be attached to a surface (e.g., the solid support) in any manner or any method; including, e.g., reversible or non-reversible binding, covalent or non-covalent attachment, and the like.

The herein mentioned capture reagent being immobilized to a solid support and being capable of binding one or more markers of the present invention, wherein said capture reagent is also termed "capture reagent according to the present invention" hereinafter, is preferably selected from the group consisting of: a protein comprising or consisting of an amino acid sequence having at least 70%, preferably at least 80%, more preferably at least 90%, still more preferably at least 95% or in particular 100% sequence identity with the sequence of any one of SEQ ID NOs: 1 to 6; a protein comprising or consisting of an amino acid sequence having at least 70%, preferably at least 80%, more preferably at least 90%, still more preferably at least 95% or in particular 100% sequence identity with the sequence of SEQ ID NO:7 or SEQ ID NO:8; an RNA virus capable of infecting insect cells, wherein said virus optionally has been inactivated; an oligonucleotide that is capable of specific hybridization with sequences characteristic of the sequence SEQ ID NO:9; and an oligonucleotide that is capable of specific hybridization with sequences characteristic of the sequence SEQ ID NO:15.

The term "specific hybridization" as described herein in particular relates to hybridization under stringent conditions. Said hybridization conditions may be established according to conventional protocols described, for example, in Sambrook, "Molecular Cloning, A Laboratory Handbook", $2^{nd}$ edition (1989), CSH Press, Cold Spring Harbor, N.Y.; Ausubel, "Current Protocols in Molecular Biology", Green Publishing Associates and Wiley Interscience, N.Y. (1989); or Higgins and Hames (eds) "Nucleic acid hybridization, a practical approach" IRL Press Oxford, Washington D.C. (1985). An example for specific hybridization conditions is hybridization in 4×SSC and 0.1% SDS at 65° C. with subsequent washing in 0.1×SSC, 0.1% SDS at 65° C. Alternatively, stringent hybridization conditions are, for example, 50% formamide, 4×SSC at 42° C.

The term "solid support", as mentioned herein, denotes a non-fluid substance, and includes chips, vessels, and particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid support component of an assay is distinguished from inert solid surfaces with which the assay may be in contact in that a "solid support" contains at least one moiety on its surface, which is intended to interact with the capture reagent, either directly or indirectly. A solid support may be a stationary component, such as a tube, strip, cuvette, or microtiter plate, or may be non-stationary components, such as beads and microparticles. Microparticles can also be used as a solid support for homogeneous assay formats. A variety of microparticles that allow both non-covalent or covalent attachment of proteins and other substances may be used. Such particles include polymer particles such as polystyrene and poly(methylmethacrylate); gold particles such as gold nanoparticles and gold colloids; and ceramic particles such as silica, glass, and metal oxide particles. See for example Martin, C. R., et al., Analytical Chemistry-News & Features 70 (1998) 322A-327A, which is incorporated herein by reference.

A "chip" is a solid, non-porous material, such as metal, glass or plastics. The material may optionally be coated, entirely or in certain areas. On the surface of the material any array of spots is present, either visible or in coordinates. On each spot a defined polypeptide, with or without linker or spacer to the surface of the material, may be immobilized. All documents mentioned herein, both supra and infra, are hereby incorporated herein by reference.

The RNA virus capable of infecting insect cells, as mentioned herein, which is also termed "the RNA virus according to the present invention" hereinafter, is preferably: a (−)ssRNA virus and is optionally a virus which belongs to the family Rhabdoviridiae; and/or a virus which comprises a protein comprising or consisting of an amino acid sequence having at least 70%, preferably at least 80%, more preferably at least 90%, still more preferably at least 95% or in particular 100% sequence identity with the sequence of SEQ ID NO:1 and/or; a protein comprising or consisting of an amino acid sequence having at least 70%, preferably at least 80%, more preferably at least 90%, still more preferably at least 95% or in particular 100% sequence identity with the sequence of SEQ ID NO:7; and/or a virus whose genome comprises a nucleic acid molecule which encodes a protein comprising or consisting of a sequence having at least 70%, preferably at least 80%, more preferably at least 90%, still more preferably at least 95% or in particular 100% sequence identity with the sequence of SEQ ID NO:1 and/or; a protein comprising or consisting of a sequence having at least 70%, preferably at least 80%, more preferably at least 90%, still more preferably at least 95% or in particular 100% sequence identity with the sequence of SEQ ID NO:7; and/or a virus whose genome comprises an RNA molecule having a sequence that is inverse complementary to a nucleic acid sequence having at least 70%, preferably at least 80%, more preferably at least 90%, still more preferably at least 95% or in particular 100% sequence identity with the sequence of SEQ ID NO:9 and/or; a sequence that is inverse complementary to a nucleic acid sequence having at least 70%, preferably at least 80%, more preferably at least 90%, still more preferably at least 95% or in particular 100% sequence identity with the sequence of SEQ ID NO:15.

All nucleotide sequences of the sequence listing are typed in 5'-'3 direction. The sequences of SEQ ID NOs. 9 and 15 encode cDNAs having a positive polarity (+ strand). The term "inverse complementary" means that the sequence is anti-parallel to the reference sequence.

The RNA virus according to the present invention is preferably able to replicate at least two or more preferably at least three weeks in an insect cell line.

Preferably, the method of the present invention comprises determining in the biological sample the presence or absence of the one or more markers of the present invention, wherein said markers are antibodies specific for a protein comprising or consisting of a sequence having at least 70%, preferably at least 80%, more preferably at least 90%, still more preferably at least 95% or in particular 100% sequence identity with the sequence of SEQ ID NO:1 or; antibodies specific for a protein comprising or consisting of a sequence having at least 70%, preferably at least 80%, more preferably at least 90%, still more preferably at least 95% or in particular 100% sequence identity with the sequence of SEQ ID NO:7; and wherein said method comprises the steps of:

a. contacting the biological sample with a capture reagent immobilized to a solid support, wherein the capture reagent is selected from the group consisting of a protein comprising or consisting of a sequence having at least 70%, preferably at least 80%, more preferably at least 90%, still more preferably at least 95% or in particular 100% sequence identity with the sequence of any one of SEQ ID NOs: 1 to 6 or a sequence having at least 70%, preferably at least 80%, more preferably at least 90%, still more preferably at least 95% or in particular 100% sequence identity with the sequence of SEQ ID NO:7 or SEQ ID NO:8, an optionally inactivated virus which comprises a protein comprising or consisting of an amino acid sequence having at least 70%, preferably at least 80%, more preferably at least 90%, still more preferably at least 95% or in particular 100% sequence identity with the sequence of SEQ ID NO:1 and/or; a protein comprising or consisting of an amino acid sequence having at least 70%, preferably at least 80%, more preferably at least 90%, still more preferably at least 95% or in particular 100% sequence identity with the sequence of SEQ ID NO:7, a virus whose genome comprises a nucleic acid molecule which encodes a protein comprising or consisting of an amino acid sequence having at least 70%, preferably at least 80%, more preferably at least 90%, still more preferably at least 95% or in particular 100% sequence identity with the sequence of SEQ ID NO:1 and/or; a protein comprising or consisting of a sequence having at least 70%, preferably at least 80%, more preferably at least 90%, still more preferably at least 95% or in particular 100% sequence identity with the sequence of SEQ ID NO:7, wherein said virus optionally has been inactivated, a virus whose genome comprises an RNA molecule which comprises a sequence that is inverse complementary to a nucleic acid sequence having at least 70%, preferably at least 80%, more preferably at least 90%, still more preferably at least 95% or in particular 100% sequence identity with the sequence of SEQ ID NO:9 and/or; a sequence that is inverse complementary to a nucleic acid sequence having at least 70%, preferably at least 80%, more preferably at least 90%, still more preferably at least 95% or in particular 100% sequence identity with the sequence of SEQ ID NO:15, wherein said virus optionally has been inactivated.

b. separating the biological sample from the immobilized capture reagent;

c. contacting the immobilized capture reagent-antibody complex with a detectable agent that binds to the antibody of the reagent-antibody complex; and d. measuring the level of antibody bound to the capture reagent using a detection means for the detectable agent, and wherein the measuring step (d) preferably further comprises a comparison with a standard curve to determine the level of antibody bound to the capture reagent.

Preferably, said detectable agent that binds to the antibody of the reagent-antibody complex is a detectable antibody, more preferably a labelled secondary antibody.

The capture reagent, as described herein, is preferably a baculovirus-expressed protein, and said baculovirus-expressed protein is preferably expressed by the baculovirus of the present invention, which is described herein underneath.

According to another preferred aspect of the invention, the one or more markers of the present invention may also be one or more T cells specific for the RNA virus according to the invention and/or one or more B cells specific for the RNA virus according to the invention and/or one or more antigen-presenting cells presenting one or more antigens according to the present invention. The presence or absence of said one or more B cells and/or said one or more T cells and/or said one or more antigen-presenting cells is preferably determined by means of a flow cytometry analysis, and wherein in particular one or more fluorescence labeled antigens according to the present invention are used for labeling said one or more B cells and/or said one or more T cells and/or wherein one or more fluorescence labeled antibodies specific for the RNA virus according to the present invention are used for labeling said one or more antigen-presenting cells.

The recombinant protein produced by an expression system in cultured insect cells, as mentioned herein, which is also termed "recombinant protein of the present invention" hereinafter is preferably PCV2 ORF2 protein, and said PCV2 ORF2 protein is in particular a protein having at least 90%, preferably at least 91%, more preferably at least 92%, still more preferably at least 93% or in particular at least 94% or at least 95% sequence identity with the sequence of SEQ ID NO:23.

According to another preferred aspect the recombinant protein of the present invention is influenza hemagglutinin, in particular avian influenza hemagglutinin, wherein said avian influenza hemagglutinin is preferably H5 protein of H5N1 virus, and wherein said H5 protein of H5N1 virus is more preferably a protein comprising or consisting of an amino acid sequence having at least 70%, preferably at least 80%, more preferably at least 90%, still more preferably at least 95% or in particular 100% sequence identity with the sequence of SEQ ID NO:24.

The method of the present invention preferably further comprises the step of determining in the biological sample the presence of one or more analytes selected from the group consisting of: antibodies specific for the recombinant protein of the present invention, a polypeptide specific for the recombinant protein of the present invention, a nucleotide sequence specific for the DNA sequence encoding the recombinant protein of the present invention.

Within the context of the method of the present invention, the immunogenic composition is preferably the immunogenic composition as described underneath.

The term "biological sample" as used herein refers to any sample that is taken from an individual (e.g. from a pig or a bird) and includes, without limitation, cell-containing bodily fluids, peripheral blood, blood plasma or serum, saliva, tissue homogenates, lung and other organ aspirates, and lavage and enema solutions, and any other source that is obtainable from a human or animal subject. For animals, examples of a "biological sample" include blood, cells, feces, diarrhea, milk, mucus, phlegm, pus, saliva, semen, sweat, tear, urine, tears, ocular fluids, vaginal secretions, and vomit, if present in that animal.

The biological sample, as referred to herein, has preferably been isolated from a mammal or a bird, preferably from a pig or a chicken (*Gallus gallus domesticus*), and/or is particular selected from the group consisting of whole blood, blood plasma, serum, urine, and oral fluids. Herein, the term "serum" is meant to be equivalent to "blood serum".

The term "oral fluids" as used herein, in particular refers to one or more fluids found in the oral cavity individually or in combination. These include, but are not limited to saliva and mucosal transudate. It is particularly understood that oral fluids can comprise a combination of fluids from a number of sources (e.g., parotid, submandibular, sublingual, accessory glands, gingival mucosa and buccal mucosa) and the term "oral fluids" includes the fluids from each of these sources individually, or in combination. The term "saliva" refers to a combination of oral fluids such as is typically found in the mouth, in particular after chewing. The term "mucosal transudate", as used herein, refers to fluid produced by the passive diffusion of serum components from oral mucosal interstitia into the oral cavity. Mucosal transudate often forms one component of saliva.

The immobilized capture reagent, as described herein, is preferably coated on a microtiter plate, in particular to a microtiter plate capable to be read out by an ELISA reader.

According to another aspect, the present invention provides a recombinant baculovirus, wherein said baculovirus comprises a DNA sequence encoding a protein comprising or consisting of an amino acid sequence having at least 70%, preferably at least 80%, more preferably at least 90%, still more preferably at least 95% or in particular 100% sequence identity with the sequence of any one of SEQ ID NOs: 1 to 6 and/or; a protein comprising or consisting of an amino acid sequence having at least 70%, preferably at least 80%, more preferably at least 90%, still more preferably at least 95% or in particular 100% sequence identity with the sequence of SEQ ID NO:7 or SEQ ID NO:8; and/or wherein said baculovirus comprises a DNA sequence comprising or consisting of a sequence having at least 70%, preferably at least 80%, more preferably at least 90%, still more preferably at least 95% or in particular 100% sequence identity with the sequence of any one of SEQ ID NOs: 9 to 14 and/or; a sequence having at least 70%, preferably at least 80%, more preferably at least 90%, still more preferably at least 95% or in particular 100% sequence identity with the sequence of SEQ ID NO:15 or SEQ ID NO:16.

The present invention further provides a vector, in particular a transfer vector, which contains a DNA sequence encoding a protein comprising or consisting of an amino acid sequence having at least 70%, preferably at least 80%, more preferably at least 90%, still more preferably at least 95% or in particular 100% sequence identity with the sequence of any one of SEQ ID NOs: 1 to 6 and/or; a protein comprising or consisting of an amino acid sequence having at least 70%, preferably at least 80%, more preferably at least 90%, still more preferably at least 95% or in particular 100% sequence identity with the sequence of SEQ ID NO:7 or SEQ ID NO:8; and/or which contains a DNA sequence having at least 70%, preferably at least 80%, more preferably at least 90%, still more preferably at least 95% or in particular 100% sequence identity with the sequence of any one of SEQ ID NO: 9 to 14 and/or; a DNA sequence having at least 70%, preferably at least 80%, more preferably at least 90%, still more preferably at least 95% or in particular 100% sequence identity with the sequence of SEQ ID NO:15 or SEQ ID NO:16.

The transfer vector within the context of the invention is preferably a "baculovirus transfer vector".

The term "transfer vector" is art-recognized and refers to a first nucleic acid molecule to which a second nucleic acid has been linked, and includes for example plasmids, cosmids or phages.

In certain embodiments, a transfer vector may be an "expression vector," which refers to a replicable DNA construct used to express DNA which encodes the desired protein and which includes a transcriptional unit comprising an assembly of (i) genetic element(s) having a regulatory role in gene expression, for example, promoters, operators, or enhancers, operatively linked to (ii) a DNA sequence encoding a desired protein which is transcribed into mRNA and translated into protein, and (iii) appropriate transcription and translation initiation and termination sequences. The choice of promoter and other regulatory elements generally varies according to the intended host cell. In general, expression vectors of utility in recombinant DNA techniques are often in the form of "plasmids," which refer to circular double stranded DNA loops which, in their vector form are not bound to the chromosome. The invention is intended to include such other forms of expression vectors which serve equivalent functions and which become known in the art subsequently hereto.

Certain transfer vectors may contain regulatory elements for controlling transcription or translation, which may be generally derived from mammalian, microbial, viral or insect genes. The ability to replicate in a host, usually conferred by an origin of replication, and a selection gene to facilitate recognition of transformants, may additionally be incorporated.

Transfer vectors derived from viruses, which may be referred to as "viral vectors," may be employed in certain embodiments of the present invention. Some examples include baculoviruses, retroviruses, adenoviruses and the like. Viral vectors, in particular baculovirus vectors, e.g., a baculovirus transfer vector, are in particular preferred according to the present invention. As for expression vectors, viral vectors may include regulatory elements.

The design of any transfer vector may depend on such factors as the choice of the host cell to be transformed and/or the type of protein desired to be expressed. Moreover, the vector's copy number, the ability to control that copy number and the expression of any other proteins encoded by the vector, such as antibiotic markers (e.g., ampicillin), may also be considered.

In still a further aspect the present invention provides an immunogenic composition, which is also termed "the immunogenic composition of the present invention" hereinafter, wherein said composition comprises a recombinant protein produced by a baculovirus expression system in cultured insect cells; and one or more antigens from the RNA virus according to the present invention, wherein said virus preferably has been inactivated; and wherein said recombinant protein is preferably selected from the group consisting of a PCV2 ORF2 protein preferably comprising or consisting of a sequence having at least 90%, preferably at least 91%, more preferably at least 92%, still more preferably at least 93% or in particular at least 94% or at least 95% sequence identity with the sequence of SEQ ID NO:23; and influenza hemagglutinin, in particular avian influenza hemagglutinin, preferably H5 protein of H5N1 virus, more preferably a protein comprising or consisting of an amino acid sequence having at least 70%, preferably at least 80%, more preferably at least 90%, still more preferably at least 95% or in particular 100% sequence identity with the sequence of SEQ ID NO:24; and a protein comprising or consisting of an amino acid sequence having at least 70%, preferably at least 80%, more preferably at least 90%, still more preferably at least 95% or in particular 100% sequence identity with the sequence of any one of SEQ ID NOs:1 to 8.

The term "inactivated", as used herein, means that the antigen does not cause disease, when administered to a mammalian host or does not replicate in a host cell.

Various physical and chemical methods of inactivation are known in the art. The term "inactivated" refers to a previously virulent or non-virulent virus has been irradiated (ultraviolet (UV), X-ray, electron beam or gamma radiation), heated, or chemically treated to inactivate, kill, while retaining its immunogenicity. In one embodiment, the inactivated virus disclosed herein is inactivated by treatment with an inactivating agent. Suitable inactivating agents include beta-propiolactone, binary or beta- or acetyl-ethyleneimine, glutaraldehyde, ozone, and Formalin (formaldehyde).

For inactivation by formalin or formaldehyde, formaldehyde is typically mixed with water and methyl alcohol to create formalin. The addition of methyl alcohol prevents degradation or cross reaction during the in activation process.

More particular, the term "inactivated" means that the virus is incapable of replication in vivo or in vitro. For example, the term "inactivated" may refer to a virus that has been propagated in vitro, e.g. and has then been deactivated using chemical or physical means so that it is no longer capable of replicating.

Preferably the virus according to the present invention which has been inactivated is a virus inactivated with binary ethyleneimine (BEI).

The present invention further provides a method of producing the immunogenic composition of the present invention, comprising the steps of introducing a recombinant baculovirus encoding said recombinant protein into an insect cell, wherein said insect cell is infected with said RNA virus capable of infecting insect cells, culturing said insect cell harboring said recombinant baculovirus and said RNA virus; and recovering said recombinant protein and said virus, preferably in the supernate; and preferably further comprises the initial step of inserting a DNA sequence encoding said recombinant protein into a transfer vector capable of introducing said sequence into the genome of baculovirus, thereby producing recombinant baculovirus.

According to still another aspect, the present invention provides a kit, in particular a test kit, for determining whether an individual has received an immunogenic composition comprising a recombinant protein produced by a baculovirus expression system in cultured insect cells, wherein said kit contains one or more capture reagents immobilized to a solid support, wherein the one or more immobilized capture reagents are capable of binding of one or more markers selected from the group consisting of antibodies specific for one or more antigens according to the present invention; one or more antigens from an RNA virus according to the present invention; and one or more nucleic acid molecules according to the present invention; and wherein said one or more capture reagents are preferably selected from the group consisting of a protein comprising or consisting of an amino acid sequence having at least 70%, preferably at least 80%, more preferably at least 90%, still more preferably at least 95% or in particular 100% sequence identity with the sequence of any one of SEQ ID NOs: 1 to 6; a protein comprising or consisting of an amino acid sequence having at least 70%, preferably at least 80%, more preferably at least 90%, still more preferably at least 95% or in particular 100% sequence identity with the sequence of SEQ ID NO:7 or SEQ ID NO:8; an RNA virus capable of infecting insect cells, wherein said virus has been optionally inactivated, an oligonucleotide that is capable of specific hybridization with sequences characteristic of the sequence SEQ ID NO:9; and an oligonucleotide that is capable of specific hybridization with sequences characteristic of the sequence SEQ ID NO:15.

Furthermore, the present invention provides a primer or a pair of primers, respectively, selected from the group consisting of the sequences having at least 90% or preferably at least 95% sequence identity with the sequence of any one of SEQ ID NOs: 17 to 22.

According to another aspect, the capture reagent of the present invention comprises or consists of viral particles and/or virus like particles of an RNA virus capable of infecting insect cells, wherein said RNA virus capable of infecting insect cells is preferably the RNA virus according to the present invention, and wherein said capture reagent is obtainable by a method comprising the steps of i) obtaining supernatant from a culture of insect cells infected with an RNA virus, preferably with the RNA virus of the present invention, wherein said supernatant comprises viral particles and/or virus like particles of the RNA virus, and wherein said insect cells are preferably not infected with a baculovirus and/or are preferably not transfected with a plasmid,
ii) separating cell debris from said viral particles and/or virus like particles via a separation step including a micro filtration through at least one filter, preferably two filters, wherein the at least one filter preferably having a pore size larger than said viral particles and/or virus like particles, in particular having a pore size of about 0.1 μm to about 4 μm, preferably of about 0.2 μm to about 2 μm, and collecting the filtrate,
iii) and optionally subjecting the filtrate of ii) which contains said viral particles and/or virus like particles to size exclusion chromatography, wherein preferably the presence of protein in the eluent is measured by measuring the absorbance of light of the eluent at 260 nm or 280 nm ($A_{260}$ or $A_{280}$), and wherein the eluent exhibiting the first $A_{260}$ or $A_{280}$ peak is collected.

Also, the invention provides a composition comprising said capture reagent, wherein said composition is obtainable by said method.

In the size-exclusion chromatography (SEC) step described herein, molecules are separated according to size in a bed packed with an inert porous medium, especially an inert gel medium, which is preferably a composite of cross-linked polysaccharides, e.g., cross-linked agarose and dextran in the form of spherical beads. Molecules larger than the largest pores in the swollen gel beads do not enter the gel beads and therefore move through the chromatographic bed fastest. Smaller molecules, which enter the gel beads to varying extent depending on their size and shape, are retarded in their passage through the bed. Molecules are thus generally eluted in the order of decreasing molecular size. A SEC column comprising a medium appropriate for the size-exclusion chromatography described herein is in preferably the HiPrep 26/60 Sephacryl S300HR column (GE Healthcare Bio-Sciences).

It is in particular understood that the eluent exhibiting the first $A_{260}$ or $A_{280}$ peak is the fraction of the filtrate of ii) comprising the largest protein structures included in the filtrate of ii). Thus, the eluent exhibiting the first $A_{260}$ or $A_{280}$ peak is the eluent, or a portion thereof, containing the majority of the viral particles and/or virus like particles included in the filtrate of ii).

EXAMPLES

The following examples are only intended to illustrate the present invention. They shall not limit the scope of the claims in any way.

Example 1

Infection of Sf Cells with a Rhabdovirus, Production of Semi-Purified Rhabdovirus, and Cloning and Expression of Rhabodovirus Antigens In order to confirm the infection of SF+ and Sf9 cells with a rhabdovirus, also termed SfRV or SFRV (Sf cell rhabdovirus) hereinafter, primers were designed so as to amplify SFRV G and N genes with the goal of inserting unique 5' and 3' restriction sites. In addition, the 3' end primer was designed to add a tobacco etch virus (TEV) protease cleavage site followed by a 6× histidine tag. This was done to enable purification of the expressed protein on a nickel column using the His tag and then cleave off the His tag using the TEV protease to generate native G or N protein.

The sequences of the primers used for the G gene constructs (comprising the sequence of SEQ ID NO:1) are the sequences set forth in SEQ ID NOs: 17 and 18, the sequence of the nucleic acid for the G gene construct is provided in SEQ ID NO:12, and the amino acid sequence for the G gene construct is the sequence of SEQ ID NO:4.

The sequences of the primers used for the N gene constructs (comprising the sequence of SEQ ID NO:7) are the sequence set forth in SEQ ID NOs: 21 and 22, the sequence of the nucleic acid for the N gene construct is provided in SEQ ID NO:16, and the amino acid sequence for the N gene construct is the sequence of SEQ ID NO:8.

Further, transmembrane and intracellular domains of SFRV G glycoprotein were predicted using TMpred (www.ch.embnet.org) described in K. Hofmann & W. Stoffel (1993) TMbase—A database of membrane spanning proteins segments, Biol. Chem. Hoppe-Seyler 374,166, TMHMM (www.cbs.dtu.dk) which uses the hidden Markov model described in Möller S1, Croning Md., Apweiler R., Evaluation of methods for the prediction of membrane spanning regions, Bioinformatics (2001) 17 (7): 646-653 and SOSUI (harrier.nagahama-i-bio.ac.jp). Based on results from TMpred and TMHMM, the SFRV G sequence was terminated at amino acid 550 and the TEV cleavage site, 6× His tag and Pst I sites were added. The sequences of the primers usable for such G gene constructs (comprising the sequence of SEQ ID NO:2) are the sequences set forth in SEQ ID NOs: 17 and 19, the sequence of the nucleic acid for the G gene construct is provided in SEQ ID NO:13, and the amino acid sequence for the G gene construct is the sequence of SEQ ID NO:5.

Furthermore, the sequence of honey bee melittin secretory signal was fused to the sequence of a truncated SFRV G sequence (Chouljenko et al. J Virol, 84:8596-8606 (2010); Tessier et al. Gene. 98:177-83 (1991)), wherein the melittin sequence was added to full length SFRV G with TEV cleavage and 6× his by replacing its N terminus. The sequences of the primers usable for such G gene constructs (comprising the sequence of SEQ ID NO:3) are the sequences set forth in SEQ ID NOs: 20 and 18, the sequence of the nucleic acid for the G gene construct is provided in SEQ ID NO:14, and the amino acid sequence for the G gene construct is the sequence of SEQ ID NO:6.

The whole genome sequence of the SFRV according to M A et al. (J Virol. 88: 6576-6585 (2014)) deposited in GenBank (accession number KF947078) (SEQ ID NO: 29) was used as the basis for primer design. Similarly, for TEV cleavage site the sequence ENLYFQG was used based on available published information.

SFRV was purified from the spent media used in the growth of Sf9 (adherent cells) and Sf+ (suspension cells): Spent media was collected from SFRV infected and conventionally propagated Sf9 and Sf+ cells and filtered through a 0.2 micron filter to eliminate cell debris. The filtrate was then loaded on to 30% sucrose cushions in NaCl-Tris HCl-EDTA (NTE) buffer pH 7.4 and subject to ultracentrifugation at 32,000 rpm at 4° C. for 3 hours. The supernatant was carefully aspirated out and the pellet was rehydrated and re-suspended in NTE buffer. The total protein content was measured on a nanodrop machine and aliquots were assigned lot numbers and frozen at ≤−70° C. till further use. This antigen preparation contained the semi-purified virus for coating ELISA plates, as described below.

The spent SF9 media was used as the source for SFRV viral RNA extraction. QIAamp viral RNA extraction kit (Qiagen) was used ad per manufacturer's instructions.

To amplify G and N genes, One-Step Superscript III kit was used as per manufacturer's instructions. A gradient RT-PCR was used with the following conditions: 1 cycle at 60° C. for 30 minutes (RT step) followed by one cycle at 94° C. for 2 minutes. This was followed by 40 cycles at 94° C. for 15 seconds, annealing gradient 75° C.-50° C. for 60 seconds, followed by extension at 68° C. for 2 minutes. Finally the reaction was subject to a single cycle at 68° C. for 5 minutes and an infinite hold at 4° C.

Amplified products were run on a gel to verify size. Gel bands of expected size were cut out from gel and purified using Qiaquick gel extraction kit using manufacturer's instructions (FIG. 1).

In the following, only the further work using the G gene (comprising the sequence of SEQ ID NO:1) is described.

Figure 2:
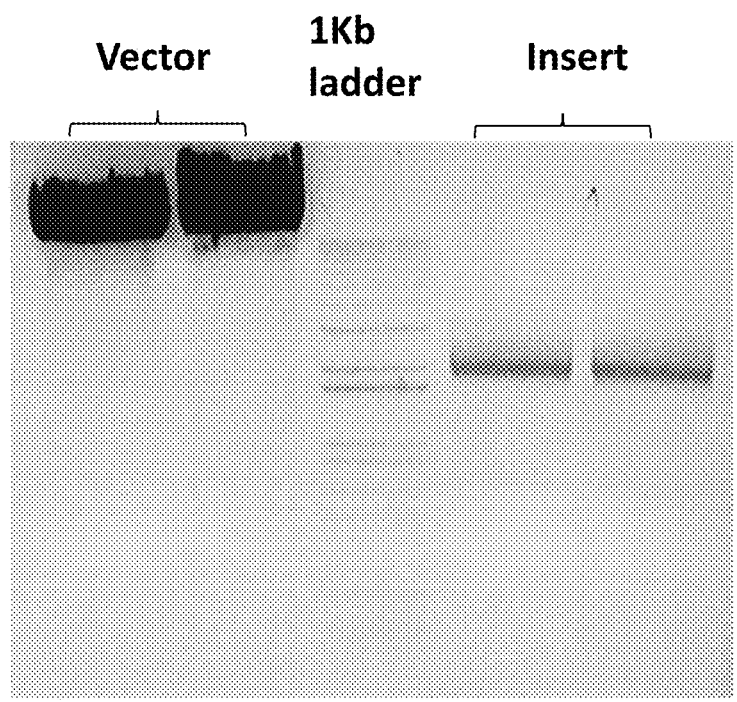

Amplified G gene (upper band in FIG. 1.) with expected size of ~1.6Kb were cut out and gel extracted. as described earlier. This was then cut with Eco RI and Pst I restriction enzymes. The cut product is the insert. Similarly baculovirus transfer vector plasmid pVL1393 (Pharmingen) (SEQ ID NO:30) was cut with Eco RI and Pst I restriction enzymes to generate the vector. Cut insert and vector were run on a gel (see FIG. 2) to check for linearization of vector. The bands were cut out and gel extracted and the vector was dephosphorylated. Cloning the insert (Eco RI-PstI cut SFRV-G construct) into the vector (Eco RI-PstI cut pVL1393, dephosphorylated) and ligated using standard procedures.

Ligated product was used to transform E. coli cells (One Shot Max efficiency DH5α chemically competent cells from Invitrogen) and cells plated on LB Agar with Ampicillin Colonies were picked up the next day and screened for uptake of plasmid using colony PCR and assigned clone numbers.

Reaction conditions for colony PCR were as follows: once cycle at 98° C. for 3 minutes followed by 34 cycles of denaturation at 98° C. for 30 seconds, Annealing at 58° C. for 30 seconds and extension at 72° C. for 2 minutes. This step was followed by a final extension step at 72° C. for 10 minutes and a final hold at 4° C.

Figure 3:
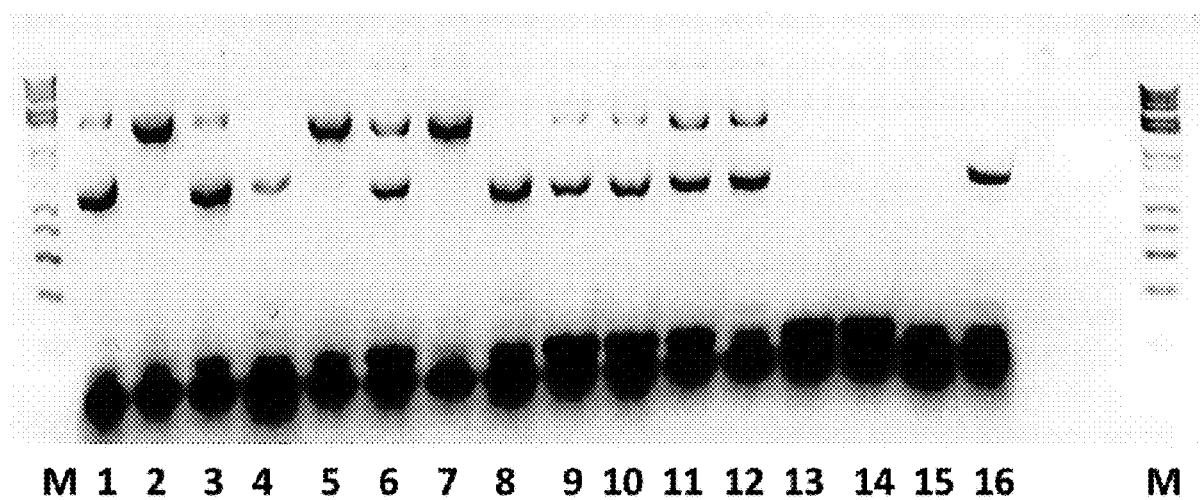

PCR products were run on an agarose gel to identify clones that contained the plasmid (see FIG. 3).

Positive clones were then grown on LB-Ampicillin broth and plasmid was purified from the cultures using Qiaprep miniprep plasmid purification kit (Qiagen) using manufacturer's instructions. The transfer vector thus generated contained the SFRV G gene construct and was aliquoted, assigned a lot number.

To generate recombinant baculoviruses expressing the SFRV G gene construct, the transfer plasmid was co-transfected along with linearized flashBAC ULTRAbaculovirus backbone DNA (Genway biotech) into Sf9 cells using ESCORT transfection reagent (SAFC). After a week, supernatants from the transfection (p0) were inoculated on to fresh Sf9 cells to amplify any recombinant baculoviruses that may have been generated.

Figure 4:
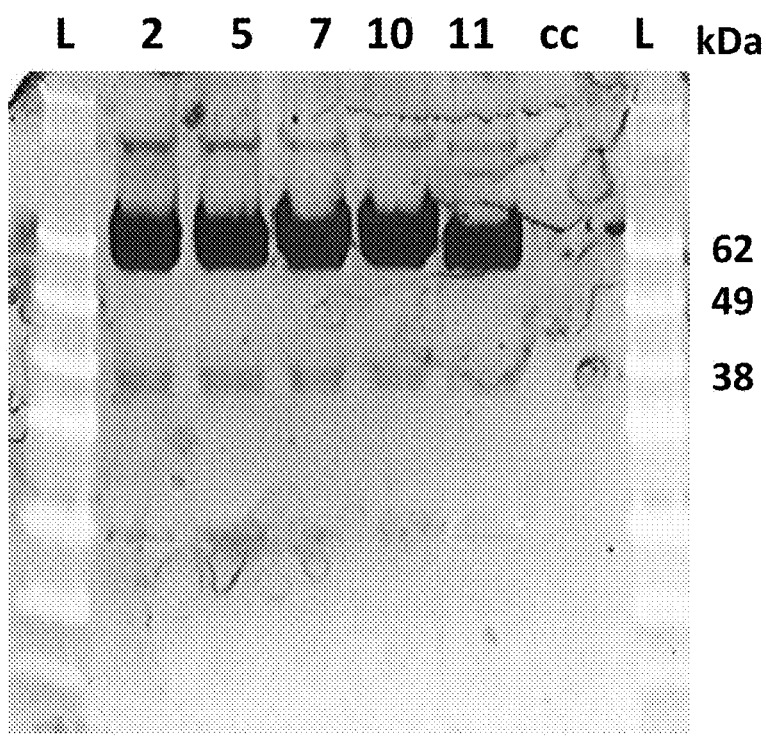

The cell pellet from the transfection was collected and run on an SDS gel and transferred onto a nitrocellulose membrane for a Western blot. The protein was probed with anti His antibody (Invitrogen). The predicted protein size is ~71.5 KDa (SEQ ID NOs. 1-6). The gel shows (FIG. 4) two close bands at and above 62 KDa marker for all five clones tested (2, 5, 7, 10 and 11) but no bands in cell control lane (cc).

Figure 5:
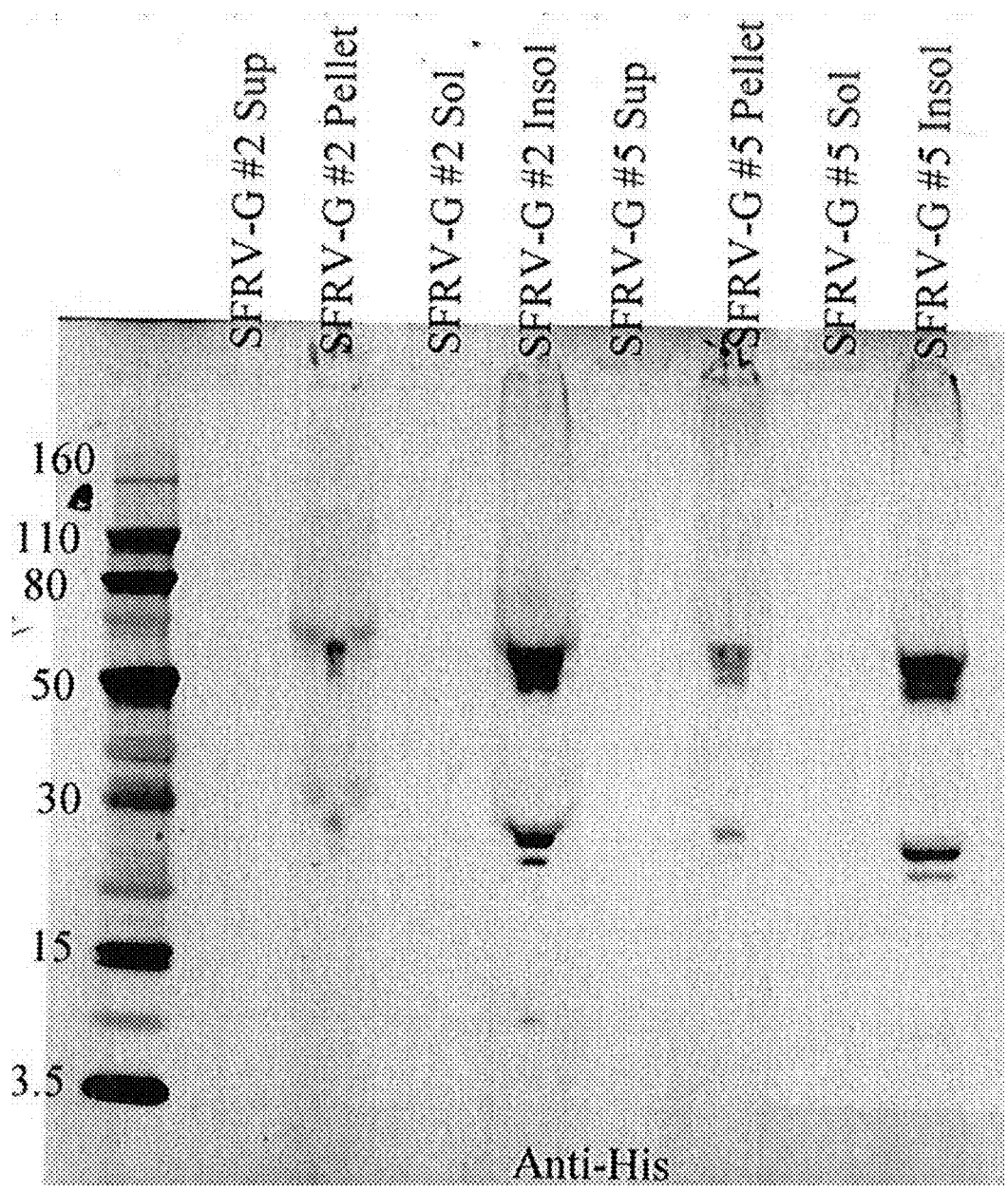

Clones 2 and 5 of the recombinant virus was passed further and grown in spinner flasks to mass produce the protein in Sf+ suspension culture. The supernatant, soluble and insoluble cell fractions were probed for the protein. At this time protein was only present in the insoluble portion (FIG. 5). As a result, C-terminal truncations of SFRV G glycoproteins are being generated as a next step for use in an ELISA assay.

Example 2

ELISA Development

An ELISA was developed to evaluate the presence of an antibody response against SFRV in animals vaccinated with PCV2 or other subunit vaccines baculovirus expressed in SFRV infected Sf cells. Briefly, ELISA plates were coated with 250 ng/well of semi-purified SFRV antigen (as described above) (SEQ ID NOs. 1-6) from either Sf9 or Sf+ cell supernatant.

Coating was done by diluting the antigen in carbonate-bicarbonate buffer pH 9.0 so as to yield a final concentration of 250 ng/well. Coating was done at 4° C. overnight.

Plates were washed the next day with PBS-Tween (PBST) and blocked with 10% milk for 1 hour at room temperature.

Plates were then probed with 1:100 diluted serum (in blocking buffer) from animals vaccinated with PCV2 subunit antigen, baculovirus expressed in SFRV infected Sf cells, or unvaccinated controls (see data section).

The plates were incubated at 37° C. for 1 hour and then washed 5× times with PBST to eliminate unbound antibodies.

Plates were then probed with 1:10,000 diluted secondary antibody (goat ant-pig IgG H+L-HRP conjugate—Bethyl laboratories), incubated 37° C. for 1 hour and then washed 5× times with PBST to eliminate unbound antibodies.

Finally, SureBlue TMB substrate (KPL) was added and plates were incubated for 5 minutes at room temperature and then stopped with TMB stop solution (KPL). Plates were then read at 450 nm.

The ELISA Plate Set Up was:

Row a, wells 1-10 were coated with Sf9 derived SFRV
Row b, wells 1-10 were coated with Sf+ derived SFRV Swine sera were evaluated in duplicates and animals vaccinated with PCV2 (A, B) subunit antigen are shown in bold. These should show a positive readout if the animals had encountered SFRV through vaccination and generated antibodies to SFRV.

Negative controls are shown in italics (C and D)

Columns 9 and 10 are buffer controls (no primary antibody)

The results of the ELISA are shown in Table 1.

TABLE 1

|  | A | | B | | C | | D | | | |
|---|---|---|---|---|---|---|---|---|---|---|
|  | 1 | 2 | 3 | 4 | *5* | *6* | *7* | *8* | 9 | 10 |
| Row a | 0.774 | 0.626 | 0.217 | 0.215 | *0.058* | *0.098* | *0.095* | *0.091* | 0.044 | 0.039 |
| Row b | 1.857 | 0.909 | 1.556 | 1.028 | *0.993* | *0.554* | *0.104* | *0.103* | 0.041 | 0.033 |

Table 1 shows data evaluating SfRV antigen derived from Sf9 cells (Row A) and Sf+ cells (Row B). Four sera samples were evaluated in duplicates. Columns A and B contained day 28 serum from animals vaccinated with experimental vaccine while columns C and D contained serum from negative control animals. The results indicate that both Sf9 and Sf+ cells contained SfRV and could be used as the virus antigen. Furthermore, the specific recognition of the antigen in vaccinated but not control animals point to the usefulness of SfRV as an inherent compliance marker.

Data Interpretation:

Based on the ELISA read out, animals vaccinated with PCV2 subunit antigen (Groups A and B) show a good response against semi-purified SFRV.

The negative control animals (Groups C and D) do not show a reaction to the semi-purified SFRV.

The results indicate the usefulness of SFRV for inherent compliance marking and for a DIVA approach.

Example 3

ELISA Using the SFRV Antigen (Wherein the Antigen is a Protein Comprising the Sequence of any One of SEQ ID NOs: 1 to 6, or Wherein the Antigen is Purified or Semi-purified Virus According to the Present Invention) Described Above SCOPE: Test serum (or oral fluids) samples for the presence of antibodies to SFRV antigens Materials and Methods A. Equipment ELISA washer
ELISA reader
WFI for cell culture, USP (Gibco, catalog# A12873-02)
Carbonate-Bicarbonate buffer (pH9.6) tablets (Sigma, catalog# C3041-100CAP)
96 well immuno plates (round or flat bottom plates, Nunc Maxisorb)
12-channel pipettors, miscellaneous pipettors with range of 1 μL to 1 mL.
pipette tips
37° C. incubator
4° C. refrigerator
Vortexer
plate lids (Thermo, catalog# AB-0752)
S-block 2 mL dilution blocks (Phenix catalog# M-1810S, or equivalent)
reagent reservoirs
timer B. Reagents
1. Coating Buffer: Carbonate-Bicarbonate Buffer
   100 mL of WFI
   1 capsule of Carbonate-Bicarbonate Buffer
   Open capsule, dispense powder into WFI, mix until dissolved
   filter sterilize solution using a 0.2 μm filter
   store at 4° C.
   Expiry: 1 week
   Needed per assay (4 plates): 50 mL
2. 10×PBS:
   1 package PBS concentrate, Fisher BP665-1
   qs to 1 L with GenPur $H_2O$ (or equivalent)
   store at room temperature
   Expiry: 1 year
3. Wash Buffer Solution: 0.05% Tween 20 in Dulbeccos PBS.
   0.5 mL of Tween 20, Fisher BP337, or equivalent
   100 mL of 10×D-PBS, pH 7.2-7.4
   q.s. to 1 L with GenPur $H_2O$ (or equivalent)
   pH to 7.2±0.1
   store at room temperature
   Expiry: 6 months
   Needed per assay (4 plates): 2 Liters
4. PBST:
   500 mL 1×PBS pH 7.4 (Gibco, catalog#10010-023)
   0.3 mL of tween 20, Fisher BP337, or equivalent
   Store at room temperature
   Expiry: 6 months
   Needed per assay (4 plates): 100 mL
5. Block Solution: 10% Non-fat dry milk in PBST solution.
   20 g blotting grade block, Bio-Rad 170-6404, or equivalent
   200 mL of PBST
   Store at 4° C.
   Expiry: 0 days
   Needed per assay (4 plates): 200 mL
6. SFRV Antigen:
   Uninfected SF or SF+ cell culture supernatant is filtered through a 0.2 micron filter (Thermo cat 456-0020). In this context, "uninfected SF or SF+ cell culture supernatant" means supernatant of SF or SF+ cells in culture, wherein said cells are not infected with baculovirus, but are infected with SFRV.
   Furthermore, in the context of the cells described in the present disclosure, the term "SF" is equivalent to the term "Sf", the term "SF+" is equivalent to the the term "Sf+", and the term "SF9" is equivalent to the term "Sf9", respectively.
   The filtrate is loaded on a 30% sucrose cushion and centrifuged at 28,000-34,000 rpm at 4° C. for 2-4 hours
   - After centrifugation, the supernatant is carefully aspirated out and the pellet is suspended in NaCl-Tris-EDTA buffer pH 7.4
   - This is the semi-purified antigen.
   - The protein concentration is estimated spectrophotometrically and the protein is aliquoted and frozen at −70° C. until use
7. 2° Antibody: Goat anti-Pig IgG h+l HRP Conjugated. Bethyl Labs Cat. No. A100-105P, stored at 4° C.±3.0° C.
8. Substrate: SureBlue TMB 1-Component Microwell Peroxidase Substrate. Kirkgaard and Perry Laboratories Cat No. 52-00-01 or equivalent. Substrate will be stored at 4° C.±3.0° C., pre-incubated at 25° C.±2.0° C., and used at 25° C.±3.0° C.
9. Stop Solution: TMB Stop Solution. Kirkgaard and Perry Laboratories Cat No. 50-85-04 or equivalent. Stored at room temperature.

C. Procedure

1. Prepare Coating Buffer using recipe listed in B1 above.
2. Dilute SFRV antigen (SEQ ID Nos. 1-6) in coating butter to 250 ng/well. Mix by inverting 10 times antigen. Coat with 250 ng/100 μl (i.e. 2.5 μg/ml=250 ng/well).
3. Add 100 μL of diluted SFRV antigen to all wells,
4. Seal the test plate(s) with plate lids and incubate overnight at 4° C., place on the bottom of the refrigerator to minimize disturbance.

Next Day

5. Prepare enough blocking solution for current assay only. Recommend 200 mL Block for 4 plates. Store at 4° C. temperature until needed.
6. Wash test plate(s) 5 times with wash buffer using the ultrawash plus microtiter plate washer, or equivalent.
7. A 100 μL of blocking solution to all the wells of test plate(s). Cover the test plate(s) and incubate for 1.0 hour at 37° C.±2.0° C.
8. During blocking incubation, dilute test serum samples 1:100 in block in s-block. For oral fluids, dilute the samples 1:2 in block. Each sample tested individually. Dilute positive and negative controls in the same fashion.
9. Wash test plate(s) 1× times. After last wash gently tap plates onto a paper towel.
10. Add 100 μL per well of the pre-diluted test samples to respective plate(s). Avoid well contact with the tip of the pipette. Changing tips between each test sample. Cover test plate(s) and incubate for 1.0 hour at 37° C.±2.0° C. for serum samples. For oral fluids samples incubate for 16.0 hours at 4° C.±2.0° C.
11. Just prior to washing the test plate(s), remove secondary antibody vial from refrigerator and dilute to 1:10,000 in block. Recommended to make serial dilutions to achieve a 1:10,000 dilution (4 dilutions). Mix diluted antibody by inversion 10 times.
12. Wash test plate(s) 5 times.
13. Add 100 μL of diluted detection antibody to all wells of the test plate(s). Cover test plate(s) and incubate for 1.0 hour at 37° C.±2.0° C.
14 Immediately remove SureBlue TMB 1-Component Microwell Peroxidase Substrate from the refrigerator (4° C.±3° C.) and transfer appropriate volume to a brown, or opaque, High Density Polyethylene (HDPE) container, and incubate for 1 hour+15 minutes at 25° C.±2.0° C. (bench top).
15. Wash test plate(s) 5 times. After last wash gently tap plates onto a paper towel. Recommend to turn on plate reader while plate(s) are washing.
16. Add 100 μL of substrate to all wells of the test plate(s).
17. Incubate at 25° C.±3° C. for 5 minutes.
18. Stop the reaction with the addition of 100 μL of stop solution to all wells
19. Measure absorbance at 450 nm.

D. Acceptance Criteria/Results

Positive control: serum (or oral fluid, respectively) from pigs hyper immunized with SFRV/SRFV G glycoprotein (SEQ ID Nos. 1-6)

Naïve swine sera (or oral fluids, respectively) or sera (or oral fluids, respectively) from unvaccinated swine that shows negligible to no reaction to SFRV antigen

Example 4

Production of Semi-Purified Rhabdovirus, Size Exclusion Chromatography (SEC), Real Time PCR, Electron Microscopy of SEC Fractions, and ELISA Production of Semi-Purified Rhabdovirus:

Prior to loading onto the column, semi-purified rhabdovirus was produced in that cell culture supernatant (40 mL) of SfRV infected Sf+ insect cells that was concentrated from 5 liters down to 800 mL using hollow fiber filtration was filtered through a 1.2 µm syringe filter. The resulting filtrate is the "semi-purified rhabdovirus" according to this example.

Size Exclusion Chromatography (SEC):

Size exclusion chromatography was run using isocratic conditions on an AKTA Explorer with a HiPrep 26/60 Sephacryl S300HR column (GE Healthcare Bio-Sciences) at a flow rate of 1 mL/min. The column was equilibrated with 1.5 column volumes of buffer (1× phosphate buffered saline, pH 7.4, Gibco) followed by injection of the clarified sample (approximately 5% column volume) of the semi-purified rhabdovirus produced according to (i). Separation occurred at a flow rate of 1.0 mL/min over 1.5 column volumes of buffer, and fractions (8 mL) were collected from the time of injection through the entire separation step. Elution of proteins from the column was monitored with UV absorption at 280 nm (FIG. 6) (SEQ ID Nos. 1-6).

Fractions were analyzed by 4-12% SDS-PAGE (Thermo Fisher) following concentration of peak fractions using TCA/acetone precipitation. Briefly, 1 mL of each fraction was precipitated with TCA (200 µL) for 1 hr on ice. The samples were centrifuged for 2 min at 20,000×g, and the supernatant was removed. Fractions were washed with 500 µL of ice cold acetone and mixed by vortexing followed by centrifugation for 2 min at 20,000×g. The centrifugation and acetone steps were repeated for a total of three acetone washes. The pellets were dried for 20 min, suspended in 20 µL of gel loading buffer, and loaded onto the gel. Gels were stained for 1 hr using Imperial protein stain (Thermo Fisher) and destained for at least 3 hr with deionized water. Following gel analysis, protein concentrations of fractions were determined by BCA assay (Thermo Fisher) using bovine serum albumin as a standard.

Real Time PCR

The presence of SfRV RNA in the semi-purified rhabdovirus (filtrate) of (i) and in the fractions collected by the SEC of (ii) was detected/quantified by using the following methods and sequences for Real Time PCR:

Primers/Probes/G-Block Control:

| Name | Sequence | Genomic Position* |
|---|---|---|
| Rhab_qPCR-F | SEQ ID NO: 25 | 5584-5603 |
| Rhab_qPCR-R | SEQ ID NO: 26 | 5654-5672 (RC) |
| Rhab_qPCR-PR (FAM) | SEQ ID NO: 27 | 5624-5646 (RC) |
| Rhab_gBlock | SEQ ID NO: 28 | 5565-5690 |

*Genomic position based upon GenBank Reference strain: KF947078 (SEQ ID NO: 29). All sequences target the region encoding the SfRV glycoprotein.

Cycle Conditions:

1 cycle @ 50° C. for 10 min
1 cycle @ 95° C. for 3 min
40 cycles @ 95° C. for 15 sec.
57° C. for 15 sec**Data collection (FAM)

Brief Description of Steps Performed:

Amplification is performed using BioRad iTaq Universal Probes One-Step Kit (Cat #172-5141) according to suggested manufacturers suggested protocol. Primers are added to a final concentration of 0.4 µM in a 25 µl reaction while probe is added to a final concentration of 0.16 µM. In each run a standard curve composed a synthetic double-stranded g-block (IDT) sequence corresponding to the expected amplicon. The reaction took place using a CFX96 real-time PCR detection system (BioRad) under the following conditions: initial reverse transcription at 50° C. for 10 min, followed by initial denaturation at 95° C. for 3 min, followed by 40 cycles of denaturation at 95° C. for 15 s and annealing and extension at 57° C. for 15 s with data collection in FAM channel. The optical data were analyzed using CFX Manager software (version 2.1,BioRad). Runs were deemed valid based on: consistency of standard curve, r-squared values exceeding 0.99 and calculated efficiencies between 80-120%. For each determination, the threshold lines were automatically calculated using the regression setting for cycle threshold (Ct) determination mode. Baseline subtraction was done automatically using the baseline subtracted mode.

Figure 7:
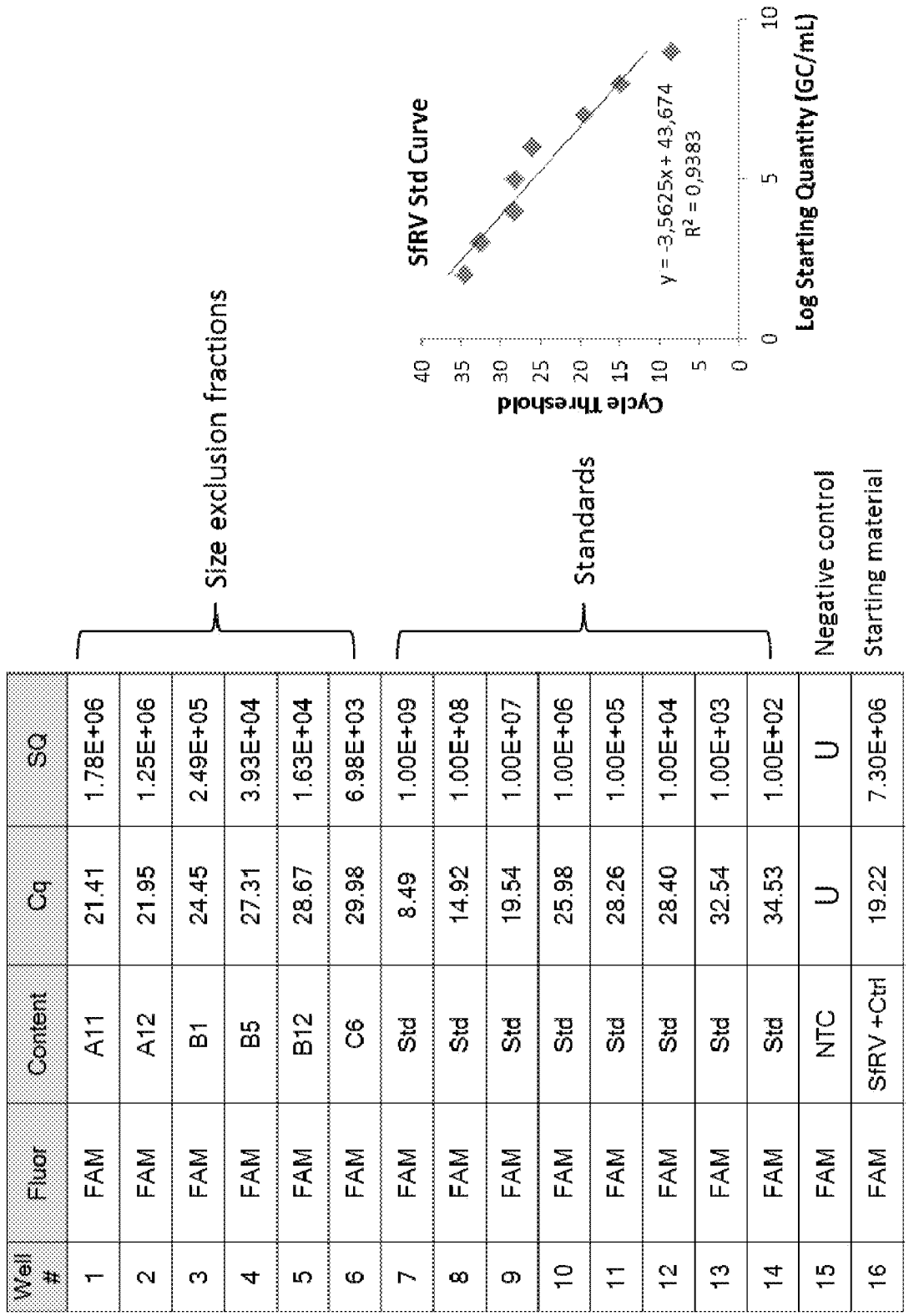

The results of the Real Time PCR are shown in FIG. 7.

In FIG. 7:

Column 1 indicates the well numbers. Column 2 shows the fluorophore_6-carboxyfluorescein (FAM) linked to the specific probe (SEQ ID NO. 27) used in this realtime PCR. Column 3 indicates the fractions of SfRV antigen (SEQ ID NOs. 25-28) derived from size exclusion chromatography (fractions A11, A12, B1, B5, B12 and C6) or the standards with known quantities of SfRV specific nucleic acid used to generate the standard curve (wells 7-14). Well 15 served as the negative control (no template) and well 16 served as the positive control containing concentrated SfRV antigen (SEQ ID NOs. 1-6) prior to fractionation by seize (SEC).

The quantitation cycle (Cq) is the cycle at which fluorescence is detected. Lower Cq values indicate higher copy numbers of the specific target in the sample. This data is shown in column 4. The extrapolated genomic copy numbers are shown in column 5 as sequence quantification (SQ) and shows the number of genomic copies per mL.

The data shows that the starting material had 6 logs of SfRV specific genomic copies/mL (well 16), similarly fractions A11 and A12 had 6 logs of genomic copies/mL. These two fractions along with tail end fraction B1 should contain the majority SfRV viral particles/virions and virus like particles (VLPs). The other fractions B5, B12 and C6 should contain subviral particles in SEC and therefore lower amounts of viral RNA if any.

Figure 6:
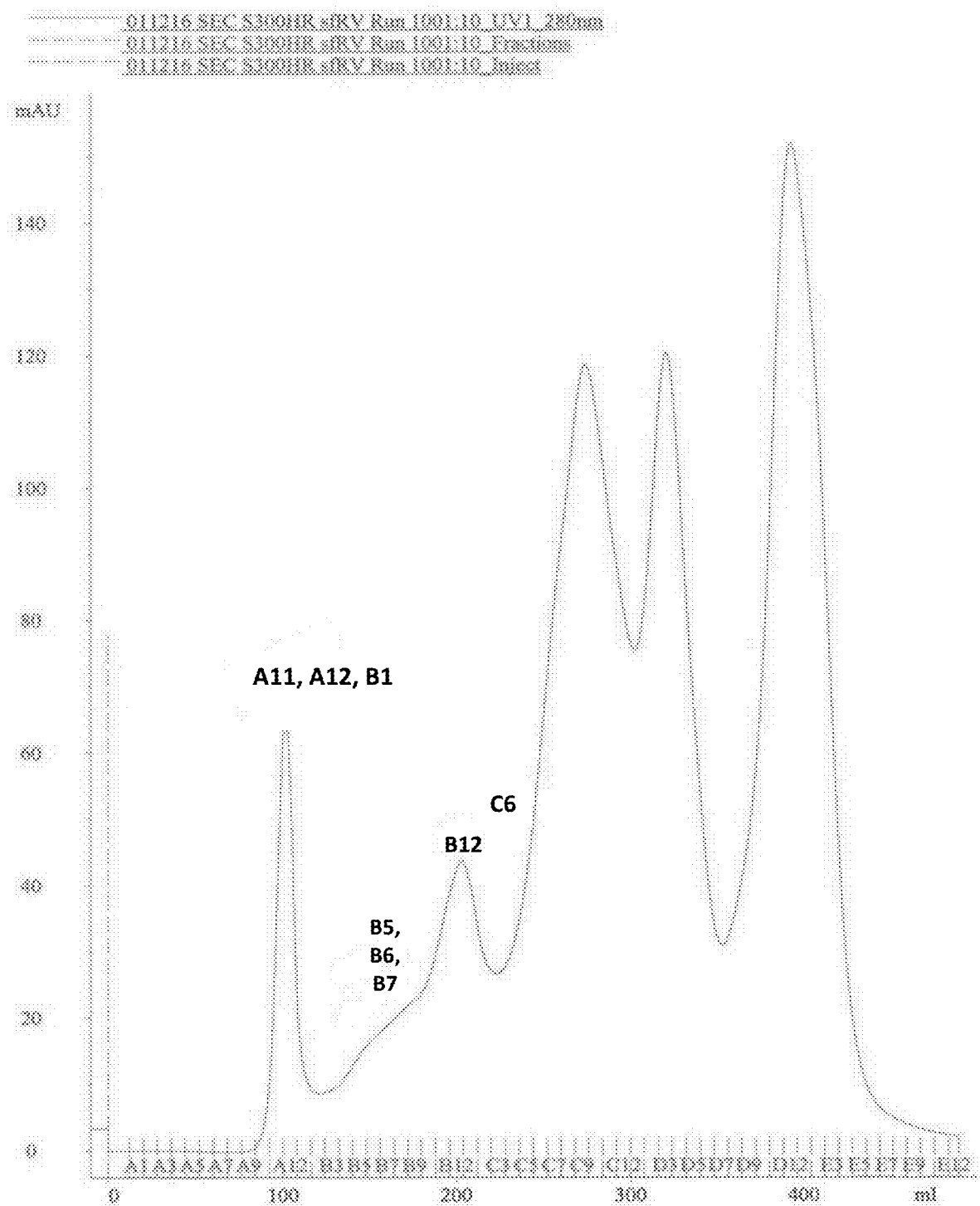

Electron Microscopy:

Fractions collected by the SEC of (ii) were stained with 2.5% phospho tungstic acid (PTA) for 3 minutes (negative staining) for electron microscopy. In the fractions A11 and A12 (c.f. FIG. 6) particles of ~30-35 nm were observed, which were considered to be viral particles of SfRV.

ELISA:

The ELISA was performed as described in Example 2, wherein the materials and methods described under Example 3 were used, with the difference that instead of the "SFRV Antigen" (under point B. 6. of Example 3) the semi-purified rhabdovirus (filtrate) of (i) and the fractions A11, A12, and B1 collected by the SEC of (ii) were used, each diluted in coating buffer to a concentration of 250 ng in 100 and then 100 µl of each of said antigens was coated on a well.

As test serum samples, blood serum from animals immunized with an experimental vaccine was used, said vaccine comprising recombinant protein produced by a baculovirus expression system in cultured SfRV infected insect cells.

The sera were obtained from blood taken from the animals 28 days after the administration of the experimental vaccine.

As negative control, blood serum of corresponding non-immunized animals was used, respectively.

Figure 8:
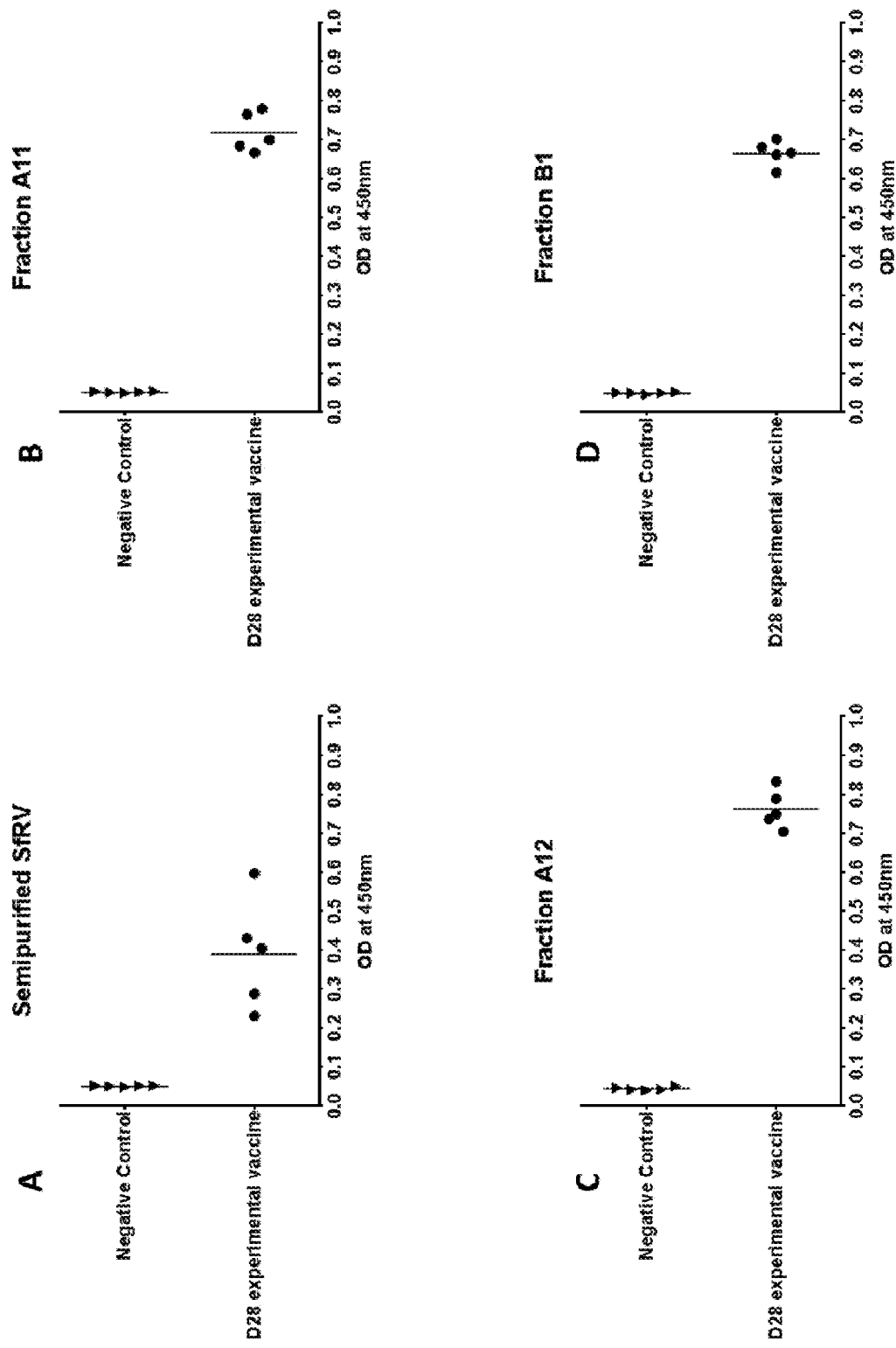

The results of the ELISA are shown in FIG. 8.

ELISA plates were coated with four different antigens including semi-purified SfRV (panel A) (i.e. corresponding to SEQ ID NOs. 1-6) size exclusion fractions A11 (Panel B), A12 (Panel C) and B1 (Panel D). Plates were probed with sera from negative control animals (inverted triangles) or Day 28 sera from animals administered with experimental vaccine containing SfRV (circles).

Results show that sera from vaccinated animal reacted to the coated antigens while the negative control serum had minimal reaction. Furthermore, vaccinated animals reacted strongly to wells coated with fractions A11, A12 and B1 (panels B, C and D) as evidenced by the increased OD values and reactions were more tightly clustered with these fractions as compared to semipurified SfRV (panel A). This indicates a stronger recognition and more specific response to the coated antigen (fractions A11, A12 and B1).

In the Sequence Listing:

SEQ ID NO:1 corresponds to the sequence of a SFRV G protein,

SEQ ID NO:2 corresponds to the sequence of a truncated SFRV G protein,

SEQ ID NO:3 corresponds to the sequence of a truncated SFRV G protein with N-terminal melittin sequence, SEQ ID NO:4 corresponds to SEQ ID NO:1 with modifications (including 6×His tag), SEQ ID NO:5 corresponds to SEQ ID NO:2 with modifications (including 6×His tag), SEQ ID NO:6 corresponds to SEQ ID NO:3 with modifications (including 6×His tag), SEQ ID NO:7 corresponds to the sequence of a SFRV N protein, SEQ ID NO:8 corresponds to SEQ ID NO:7 with modifications (including 6×His tag), SEQ ID NO:9 corresponds to a sequence encoding SEQ ID NO:1, SEQ ID NO:10 corresponds to a sequence encoding SEQ ID NO:2, SEQ ID NO:11 corresponds to a sequence encoding SEQ ID NO:3, SEQ ID NO:12 corresponds to a sequence encoding SEQ ID NO:4, SEQ ID NO:13 corresponds to a sequence encoding SEQ ID NO:5, SEQ ID NO:14 corresponds to a sequence encoding SEQ ID NO:6, SEQ ID NO:15 corresponds to a sequence encoding SEQ ID NO:7, SEQ ID NO:16 corresponds to a sequence encoding SEQ ID NO:8, SEQ ID NO:17 corresponds to a forward primer to construct SEQ ID NO:12 or SEQ ID NO:13, SEQ ID NO:18 corresponds to a reverse primer to construct SEQ ID NO:12 or SEQ ID NO:14, SEQ ID NO:19 corresponds to a reverse primer to construct SEQ ID NO:13, SEQ ID NO:20 corresponds to a forward primer to construct SEQ ID NO:14, SEQ ID NO:21 corresponds to a forward primer to construct SEQ ID NO:16, SEQ ID NO:22 corresponds to a reverse primer to construct SEQ ID NO:16, SEQ ID NO:23 corresponds to a sequence of a PCV2 ORF2 protein, SEQ ID NO:24 corresponds to a sequence of a hemagglutinin H5 protein (influenza virus).

The invention claimed is:

1. A method for determining whether an animal has received a marker vaccine including a recombinant protein produced by an expression system in cultured insect cells, comprising:
   detecting, in a biological sample derived from the animal, for a marker indicating whether the animal has been exposed to an antigen from an RNA virus capable of infecting insect cells.

2. The method of claim 1, wherein the RNA virus is a rhabdovirus.

3. The method of claim 2, wherein the marker is an antibody specific for a rhabdovirus antigen.

4. The method of claim 2, wherein the antigen is a G protein.

5. The method of claim 2, wherein the antigen is an N protein.

6. The method of claim 1, further comprising contacting the marker with a capture reagent under specific hybridization conditions, wherein the capture reagent binds the marker under the specific hybridization conditions to form a marker-capture reagent complex.

7. The method of claim 6, further comprising contacting the marker-capture reagent complex with a detectable agent that specifically binds to the marker-capture reagent complex.

8. The method of claim 7, wherein the detectable agent is a labelled secondary antibody.

9. The method of claim 6, wherein the capture reagent is a rhabdovirus.

10. The method of claim 9, wherein the rhabdovirus is inactivated.

11. The method of claim 6, wherein the capture reagent is a baculovirus-expressed protein.

12. The method of claim 6, wherein the capture reagent is (i) a polypeptide comprising a sequence having at least 95% sequence identity with any one of SEQ ID NOs: 1 to 8, (ii) a synthetic polypeptide consisting of 5 to 11 consecutive amino residues from SEQ ID NO:1, or (iii) a synthetic polypeptide consisting of 5 to 11 consecutive amino residues from SEQ ID NO:7.

13. The method of claim 1, wherein the animal is a pig or a chicken.

14. The method of claim 1, wherein the biological sample comprises whole blood, blood plasma, serum, urine, oral fluids, or any combinations thereof.

15. The method of claim 1, wherein the RNA virus is capable of infecting a *Spodoptera Frugiperda* cell line.

16. The method of claim 1, wherein the marker vaccine further comprises the antigen, and wherein the expression system is a baculovirus expression system.

17. The method of claim 16, wherein the recombinant protein is a PCV2 ORF2 protein having at least 95% sequence identity with SEQ ID NO:23.

18. The method of claim 16, wherein the recombinant protein is a hemagglutinin of an avian influenza H5N1 virus and has at least 95% sequence identity with SEQ ID NO:24.

19. The method of claim 1, wherein the marker is (i) the antigen, (ii) an antibody specific for the antigen, and/or (iii) a nucleic acid of the RNA virus.

20. The method of claim 1, wherein the marker vaccine is a positive marker vaccine, and wherein detecting the marker in the biological sample indicates that the animal has received the marker vaccine.

* * * * *